(12) United States Patent
Mikayama et al.

(10) Patent No.: US 7,193,064 B2
(45) Date of Patent: Mar. 20, 2007

(54) ANTI-CD40 MONOCLONAL ANTIBODY

(75) Inventors: Toshifumi Mikayama, Gunma (JP); Hitoshi Yoshida, San Diego, CA (US); Walker R. Force, San Diego, CA (US); Xingjie Chen, Milpitas, CA (US); Nobuaki Takahashi, Gunma (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 657 days.

(21) Appl. No.: 10/693,629

(22) Filed: Oct. 23, 2003

(65) Prior Publication Data

US 2004/0120948 A1    Jun. 24, 2004

Related U.S. Application Data

(63) Continuation-in-part of application No. PCT/JP02/04292, filed on Apr. 26, 2002, and a continuation-in-part of application No. 10/040,244, filed on Oct. 26, 2001, and a continuation-in-part of application No. 09/844,684, filed on Apr. 27, 2001, now Pat. No. 7,063,845, said application No. 10/040,244 is a continuation-in-part of application No. 09/844,684, filed on Apr. 27, 2001, now Pat. No. 7,063,845.

(30) Foreign Application Priority Data

May 11, 2001  (JP) ............................. 2001-142482
Oct. 5, 2001   (JP) ............................. 2001-310535

(51) Int. Cl.
*C07K 16/28*  (2006.01)
*A61K 39/395*  (2006.01)
*C12N 5/12*   (2006.01)
*C12N 15/13*  (2006.01)

(52) U.S. Cl. ............................. 530/388.73; 530/387.1; 530/387.3; 530/388.1; 530/388.2; 530/388.22; 530/388.7; 435/69.6; 435/326; 435/332; 435/334; 435/343; 435/343.1; 435/346; 536/23.5; 536/23.53; 424/130.1; 424/133.1; 424/141.1; 424/143.1; 424/144.1; 424/153.1; 424/173.1

(58) Field of Classification Search ............ None
See application file for complete search history.

(56) References Cited

U.S. PATENT DOCUMENTS

| | | |
|---|---|---|
| 5,677,165 A | 10/1997 | de Boer et al. |
| 5,786,456 A | 7/1998 | Ledbetter et al. |
| 5,801,227 A | 9/1998 | Fanslow, III et al. |
| 5,874,082 A | 2/1999 | de Boer |
| 6,004,552 A | 12/1999 | de Boer et al. |
| 6,051,228 A | 4/2000 | Aruffo et al. |
| 6,150,584 A | 11/2000 | Kucherlapati et al. |
| 2004/0120948 A1* | 6/2004 | Mikayama et al. ...... 424/144.1 |

FOREIGN PATENT DOCUMENTS

| | | |
|---|---|---|
| EP | 0 945 465 A1 | 9/1999 |
| EP | 0 972 445 A1 | 1/2000 |
| WO | 91/09115 | 6/1991 |
| WO | 96/33735 | 10/1996 |
| WO | 96/34096 | 10/1996 |
| WO | 99/39726 | 8/1999 |
| WO | 99/42075 | 8/1999 |
| WO | 99/55369 A1 | 11/1999 |
| WO | 99/61051 | 12/1999 |
| WO | 00/00156 | 1/2000 |
| WO | 00/75348 A1 | 12/2000 |
| WO | 01/16180 A | 3/2001 |
| WO | 01/24823 A1 | 4/2001 |
| WO | 01/56603 A1 | 8/2001 |
| WO | 01/83755 A2 | 11/2001 |
| WO | 0183755 A3 | 11/2001 |
| WO | 02/12501 A2 | 2/2002 |
| WO | 02/28904 A2 | 4/2002 |
| WO | 03/029296 A1 | 4/2003 |
| WO | 03/040170 A2 | 5/2003 |
| WO | 03/040170 A3 | 5/2003 |

OTHER PUBLICATIONS

Suzuki t al., Transplantation 82 (1 Suppl 2) p. 609, Jul. 15, 2006; Abstract #1624.*
Yamada et al., "Generation of Mature Dendritic Cells from a CD14[+] Cell Line (XS52) by IL-4, TNF-α, IL-1β, and Agonistic Anti-DC40 Monoclonal Antibody", *J. Immunol.*, 1999; 163(10): 5331-5337, XP002302209.
van Kooten et al., "Functions of CD40 on B cells, dendritic cells and other cells", *Curr. Opin. Immunol.*, 1997; 9(3): 330-337, XP004313522.
Stout et al., "The many roles of CD40 in cell-mediated inflammatory responses", *Immunol. Today*, 1996; 17(10): 487-492, XP004034711.
An et al.; Ligation of CD40 Potentiates Fas-Mediated Activation of the Cysteine Protease CPP32, Cleavage of Its Death Substrate PARP, and Apoptosis in Ramos-Burkitt Lymphoma B Cells; Cellular immunology, vol. 181; 1997; pp. 139-152.
Baccam et al.; Membrane-bound CD154, but not CD40-specific antibody, mediates NF-$\kappa$B-independent IL-6 production in B cells; Eur. J. Immunol., vol. 29; 1999; pp. 3855-3866.
Barr et al.; Functional activity of CD40 antibodies correlates tot he position of binding relative to CD154; Immunology, vol. 102; 2001; pp. 39-43.
Boon et al.; Preclinical assessment of anti-CD40 Mab 5D12 in cynomolgus monkeys; Toxicology, vol. 174; 2002; pp. 53-65.
Challa et al.; Epitope-dependent synergism and antagonism between CD40 antibodies and soluble CD40 ligand for the regulation of CD23 expression and lgE synthesis in human B cells; Allergy, vol. 54; 1999; pp. 576-583.
Clark et al.; Activation of human B cells mediated through two distinct cell surfa ce differentiation antigens, Bp35 and Bp50; Proc. Natl. Acad. Sci. USA, vol. 83; Jun. 1986; pp. 4494-4498.

(Continued)

*Primary Examiner*—Phillip Gambel
(74) *Attorney, Agent, or Firm*—Pillsbury Winthrop Shaw Pittman LLP

(57) ABSTRACT

An antibody or a functional fragment thereof, acting agonistically or antagonistically on CD40.

21 Claims, 21 Drawing Sheets

OTHER PUBLICATIONS

Clark et al.; CDw40 and BLCa-specific monoclonal antibodies detect two distinct molecules which transmit progression signals to human B lymphocytes; Eur. j. Immunol., vol. 18; 1988; pp. 451-457.

de Boer et al.; Generation of monoclonal antibodies to human lymphocyte cell surface antigens using insect cells expressing recombinant proteins; Journal of Immunological Methods, vol. 152; 1992; pp. 15-23.

Diehl et al.; CD40 activation *in vivo* overcomes peptide-induced peripheral cytotoxic T-lymphocyte tolerance and augments anti-tumor vaccine efficacy; Nature Medicine, vol. 5, No. 7; Jul. 1999; pp. 774-779.

Dullforce et al; Enhancement of T cell-independent immune responses *in vivo* by CD40 antibodies; Nature Medicine, vol. 4, No. 1; Jan. 1998; pp. 88-91.

Erickson et al.; Short-circuiting long-lived humoral immunity byt the heightened engagement of CD40; The Journal of Clinical Investigation, vol. 109, No. 5; Mar. 2002; pp. 613-620.

Francisco et al.; Construction, Expression, and Characterization of BD1-G28-5 sFv, a Single-chain Anti-CD40 Immunotoxin Containing the Ribosome-inactivating Protein Bryodin 1; The Journal of Biological Chemistry, vol. 272, No. 39; Sep. 1997; pp. 24165-24169.

Francisco et al.; Agonistic Properties and in Vivo Antitumor Activity of the Anti-CD40 Antibody SBN-14; Cancer Research, vol. 60; Jun. 2000; pp. 3225-3231.

Funakoshi et al.; Inhibition of Human B-Cell Lymphoma Growth by CD40 Stimulation; Blood, vol. 83, No. 10, May 1994; pp. 2787-2794.

Funakoshi et al.; Differential In Vitro and In Vivo Antitumor Effects Mediated by Anti-CD40 and Anti-CD20 Monoclonal Antibodies Against Human B-Cell Lymphomas; Journal of Immunotherapy, vol. 19, No. 2; 1996; pp. 93-101.

Hasbold et al.; Properties of mouse CD40: cellular distribution of CD40 and B cell activation by monoclonal anti-mouse CD40 antibodies; Eur. J. Immunol., vol. 24; 1994; pp. 1835-1842.

Hasbold et al.; Cell division number regulates IgG1 and IgE switching of B cells following stimulation by CD40 ligand and IL-4; Eur. J. Immunol., vol. 28; 1998; pp. 1040-1051.

Heath et al.; Monoclonal antibodies to murine CD40 define two distinct funtional epitopes; Eur. J. Immunol., vol. 24; 1994; pp. 1828-1834.

Hirano et al.; Inhibition of Human Breast Carcinoma Growth by a Soluble Recombinant Human CD40 Ligand; Blood, vol. 93, No. 9; May 1999; pp. 2999-3007.

Karlsson et al.; Selection of human single chian antibodies against CD40; Immunology Letters, vol. 73, Nos. 2, 3; Sep. 2000; p. 161, abstract No. 358.

Kedl et al.; CD40 stimulation accelerates deletion of tumor-specific $CD8^+$ T cells in the absence of tumor-antigen vaccination; PNAS, vol. 98, No. 19; Sep. 2001; pp. 10811-10816.

Kwekkeboom et al.; CD40 plays an essential role in the activation of human B cells by murine EL4B5 cells; Immunology, vol. 79; 1993; pp. 439-444.

Kwekkeboom et al.; Helper effector function of human T cells stimulated by anti-CD3 mAb can be enhanced by cd-stimulatory signals and is partially dependent on CD40-CD40 ligand interaction; Eur. J. Immunol., vol. 24; 1994; pp. 508-517.

Lagerkvist et al.; Single, Anitgen-Specific B Cells Used to Generate FAb Fragments Using CD40-Mediated Amplification or Direct PCR Cloning; BioTechniques, vol. 18, No. 5; 1995; pp. 862, 864-869.

Ledbetter et al.; Augmentation of Normal and Malignant B Cell Proliferation by Monoclonal Antibody to the B Cell-Specific Antigen BP50 (CDW40); The Journal of Immunology, vol. 138, No. 3; Feb. 1987; pp. 788-794.

Ledbetter et al.; Agonistic Activity of a CD40-Specific Single-Chain Fv Constructed from the Variable Regions of mAb G28-5; Critical Reviews in Immunoloby, vol. 17; 1997; pp. 427-435.

Malmborg Hager et al.; Affinity and Epitope Profiling of Mouse Anti-CD40 Monoclonal Antibodies; Scandinavian Journal of Immunology, vol. 57; 2003; pp. 517-524.

Maxwell et al.; Contrasting the Roles of Costimulation and the Natural Adjuvant Lipopolysaccharide During the Induction of T Cell Immunity; The Journal of Immunology, vol. 168; 2002; pp. 4372-4381.

Mazzei et al.; Recombinant Soluble Trimeric CD40 Ligand Is Biologically Activvve; The Journal of Biological Chemistry, vol. 270, No. 13; Mar. 1995; pp. 7025-7028.

Murphy et al.; Antibodies to CD40 Prevent Epstein-Barr Virus-Mediated Human B-Cell Lymphomagenesis in Severe Combined Immune Deficient Mice Given Human Peripheral Blood Lymphocytes; Blood, vol. 86, No. 5; Sep. 1995; pp. 1946-1953.

Paulie et al.; A p50 surface antigen restricted to human urinary bladder carcinomas and B lymphocytes; Cancer Immunology Immunotherapy, vol. 20; 1985; pp. 23-28.

Pound et al.; Minimal cross-linking and epitope requirements for Cd40-dependent suppression of apoptosis contrast with those for promotion of the cell cycle and homotypic adhesions in human B cells; International Immunology, vol. 11, No. 1; 1999; pp. 11-20.

Rolink et al.; The SCID but Not the *RAG*-2 Gene Product Is Required for Sμ-Sε Heavy Chain Class Switching; Immunity, vol. 5; Oct. 1996; pp. 319-330.

Romano et al.; Triggering of CD40 Antigen Inhibits Fludarabine-Induced Apoptosis in B Chronic Lymphocytic Leukemia Cells; Blood, vol. 92, No. 3; Aug. 1998; pp. 990-995.

Schoenberger et al.; T-cell help for cytotoxic T lymphocytes is mediated by CD40-CD40L interactions; Nature, vol. 393; Jun. 1998; pp. 480-483.

Schwabe et al.; Modulation of Soluble CD40 Ligand Bioactivity with Anti-CD40 Antibodies; Hybridoma, vol. 16, No. 3; 1997; pp. 217-226.

Sotomayor et al.; Conversion of tumor-specific $Cd4^+$ T-cell tolerance to T-cell priming through *in vivo* ligation of CD40; Nature Medicine, vol. 5, No. 7; Jul. 1999; pp. 780-787.

Stamenkovic et al.; A B-lymphocyte activation molecule related to the nerve growth factor receptor and induced by cytokines in carcinomas; The EMBO Journal, vol. 8, No. 5; 1989; pp. 1403-1410.

Tomizuka et al.; Double trans-chromosomic mice: Maintenance of two individual human chromosome fragments containing lg heavy and *k* loci and expression of fullly human antibodies; PNAS, vol. 97, No. 2; Jan. 2000; pp. 722-727.

van Mierlo et al.; CD40 stimulation leads to effective therapy of CD40 tumors through induction of strong systemic cytotoxic T lymphocyte immunity; PNAS, vol. 99, No. 8; Apr. 2002; pp. 5561-5566.

Weng et al.; Human Anti-CD40 Antagonistic Antibodies Inhibit the Proliferation of Human B Cell Non-Hodgkin's Lymphoma; Program of the 43rd Annual Meeting fo the American Society of Hematology; Dec. 2001; p. 466a, abstract No. 1947.

Zhou et al.; An Agonist Anti-Human CD40 Monoclonal Antibody that Induces Dendritic Cell Formulation and Maturation and Inhibits Proliferation of a Myeloma Cell Line; Hybridoma, vol. 18, No. 6; 1999; pp. 471-478.

* cited by examiner

KM302-1 antibody

G28-5 antibody

KM283-5 antibody

KM281-2-10-1-2 antibody

KM281-2-13 antibody

CD40L only

CD40L+5D12

CD40L+KM281-1-10 antibody

KM281-1-10 antibody

KM281-2-10-1-2 antibody

KM283-5 antibody

KM225-2-56 antibody

KM292-1-24 antibody

5D12 antibody+anti-mouse IgG antibody anti-mouse IgG antibody only

HS-Sulton

Ramos

G28-5 antibody

KM302-1 antibody

Action of anti-CD40 agonistic antibody to increase CD95 expression in Ramos cell anti-tumor effect of anti-CD40 antibody in Ramos cell-transplanted model

ANTI-CD40 MONOCLONAL ANTIBODY

CROSS REFERENCE TO RELATED APPLICATIONS

This application is a continuation-in-part of application Ser. No. 09/844,684 filed Apr. 27, 2001, now U.S. Pat. No. 7,063,845, application Ser. No. 10/040,244 filed Oct. 26, 2001 and PCT/JP02/04292 having an international filing date of Apr. 26, 2002, which designated the United States of America. This application and application Ser. No. 10/040,244 are also each a continuation-in-part of application Ser. No. 09/844,684, now U.S. Pat. No. 7,063,845. This application also claims priority under 35 U.S.C. §119(a) on Japanese Patent Applications Nos. 2001-142482 filed May 11, 2001 and 2001-310535 filed Oct. 5, 2001. The entire contents of all of the above-identified applications are hereby incorporated by reference.

TECHNICAL FIELD

The present invention relates to an antibody or a functional fragment thereof that recognizes a human CD40 antigen present on the surface of human B cells, dendritic cells (DC) and the like. Specifically, the present invention relates to an anti-human CD40 antibody or a functional fragment thereof that is substantially antagonistic to a human CD40 antigen on the dendritic cell (DC) surface, and an agonistic anti-human CD40 antibody or a functional fragment thereof that is expected to have a therapeutic effect higher than those of conventional anti-human CD40 antibodies.

BACKGROUND ART

1. CD40

CD40 is an antigen with a molecular weight of 50 kDa that is present on the cell membrane surface. CD40 is expressed on B cells, dendritic cells (DC), certain types of cancer cells, and thymic epithelial cells. CD40 is known to play a key role in proliferation and differentiation of B cells and DC. CD40 has been identified as an antigen that is expressed on the human B cell surface (E. A. Clark et. al., Proc. Natl. Acad. Sci. USA 83: 4494, 1986, I. Stamenkovic et. al., EMBO J. 8:1403, 1989). Based on the amino acid sequence homology, CD40 is thought to be a member of the TNF receptor family, to which a low affinity NGF receptor, TNF receptor, CD27, OX40, CD30 and the like belong. The gene of a ligand (CD40L) for human and mouse CD40 has been cloned recently, revealing that it is a type II membrane protein, and is expressed on activated CD4+ T cells. It has also been shown that CD40L introduces strong activation signals into human and mouse B cells.

The expression of CD40 has been confirmed more often on dendritic cells than on B cells, so that it has become clear that CD40 plays an important role. The binding of CD40 with CD40L causes the activation of antigen-presenting cells (APC). Specifically, it enhances the expression of co-stimulation molecules such as CD80 (B7-1) and CD86 (B7-2), or the production of IL-12 (Caux, C., et al.: Activation of human dendritic cells through CD40 cross-linking. J. Exp. Med., 180:1263, 1994), (Shu, U., et al: Activated T cells induce interleukin—12 production by monocyte via CD40—CD40 ligand interaction. Eur. J. Immunol. 25: 1125, 1995). Dendritic cells show strong antigen-presenting ability, and have strong helper T (Th) cell-activating ability. Furthermore, it is thought that dendritic cells control the differentiation of naive Th cells into Th1 or Th2 cells. When dendritic cells (DC1) are made to mature by culturing peripheral blood monocytes that are myeloid dendritic cells in the presence of GM-CSF and IL-4 and using CD40L, the DC1 in vitro are capable of producing IL-12, stimulate and activate allo-naive Th cells, and thus induce IFNγ-producing T cells (specifically, promotes differentiation into Th1). Since this action is inhibited by anti-IL-12 antibodies, the reaction may be mediated by IL-12. On the other hand, when lymphocyte-dendritic cells (DC2) are prepared by culturing lymphatic tissue T regions or plasmacytoid T cells present in peripheral blood with IL-3 and CD40 ligands, DC2 are incapable of producing IL-12, stimulate and activate allo-naive Th cells, induce IL-4-producing T cells, and thus promote differentiation into Th2. It is thought that Th1 cells are involved in the activation of cellular immunity, and Th2 cells are involved in enhancement of the ability for humoral immunity as well as the suppression of the ability for cellular immunity. Cytotoxic T cells (CTL) activated with the help of Th1 cells can remove causative factors (many viruses, *Listeria monocytogenes, tubercle bacillus*, toxoplasma protozoa and the like) multiplying in the cytoplasm and tumor cells.

It has been shown that anti-CD40 monoclonal antibodies that recognize CD40 expressed on the membrane surfaces exert a variety of biological activities on B cells. Anti-CD40 monoclonal antibodies are largely classified into agonistic and antagonistic antibodies impacting the interaction between CD40 and CD40L.

2. Agonistic Antibody

The activation of B cells is known as an action of agonistic antibodies. For example, anti-CD40 antibodies have been reported to induce cell adhesion (Barrett et al., J. Immunol. 146: 1722, 1991; Gordon et al., J. Immunol. 140: 1425, 1988), enhance cell size (Gordon et al., J. Immunol. 140: 1425, 1988; Valle et al., Eur. J. Immunol. 19: 1463, 1989), induce the division of B cells that are activated only with anti-IgM antibodies, anti-CD20 antibodies or phorbol ester (Clark and Ledbetter, Proc. Natl. Acad. Sci. USA 83: 4494, 1986; Gordon et al., LEUCOCYTE TYPING III. A. J. McMicheal ed. Oxford University Press. Oxford, p. 426; Paulie et al., J. Immunol. 142: 590, 1989), induce the division of B cells in the presence of IL4 (Valle et al., Eur. J. Immunol. 19: 1463, 1989; Gordon et al., Eur. J. Immunol. 17: 1535, 1987), induce the expression of IgE (Jabara et al., J. Exp. Med. 172: 1861, 1990; Gascan et al., J. Immunol. 147: 8, 1991), IgG and IgM (Gascan et al., J. Immunol. 147: 8, 1991) of cells stimulated with IL-4 and cultured without T cells, enhance the secretion and the on-the-cell expression (Challa A, Allergy, 54: 576, 1999) of soluble CD23/Fcε RII from B cells by IL-4 (Gordon and Guy, Immunol. Today 8: 339, 1987; Cairns et al., Eur. J. Immunol. 18: 349, 1988), and promote IL-6 production (Clark and Shu, J. Immunol. 145: 1400, 1990). Furthermore, it has been reported that B cell clones are established from human primary culture B cells by adding IL-4 and anti-CD40 antibodies in the presence of CDw32+ adhesion cells (Bancherau et al., Science 241:70, 1991), and the inhibition of the apoptosis of germinal center cells is mediated by CD40, regardless of the function of antigen receptors (Liu et al., Nature 342: 929, 1989). As described above, CD40 has been identified as an antigen expressed on the human B cell surface. Thus, most of the isolated antibodies have been evaluated mainly using function to induce the proliferation and differentiation of human B cells and activity to induce cell death in cancer cells as indicators (Katira, A. et. al., LEUKOCYTE TYPING V. S. F. Schlossossman, et al. eds. p. 547. Oxford University Press. Oxford, W. C. Flansow et al., LEUKOCYTE TYPING V. S. F. Schlossossman, et al. eds. p. 555. Oxford University Press. Oxford, J. D. Pound et al., International Immunology, 11: 11, 1999).

Anti-CD40 antibodies were shown to cause the maturation of DC (Z. H. Zhou et. al., Hybridoma, 18: 471 1999). Moreover, the role of CD4T cells in antigen-specific CD8T cell priming has been reported to activate DC via CD40-CD40L signaling. It was shown that the role of CD4 helper T cells in activation of dendritic cells (DC) can be replaced by that of anti-CD40 monoclonal antibodies (mAb) (Shoenberger, S. P., et al.: T-cell help for cytotoxic T lymphocytes is mediated by CD40-CD40L interactions. Nature, 480, 1998). Furthermore, it was shown in mice that the organism can be protected not only from tumor cells expressing CD40 but also from tumor cells not expressing the same by the administration of anti-CD40 antibodies (French, R. R., et. al.: CD40 antibody evokes a cytotoxic T-cell response that eradicates lymphoma and bypasses T-cell help. Nature Medicine, 5, 1999).

Most antibodies reported to date have not been isolated using the effect on DC as an indicator. However, in terms of the modification of DC functions, antibodies selected by their action on B cells are likely to be insufficient as therapeutic agents. It was reported that among monoclonal antibodies against mouse CD40, there are clones that react to DC, but do not react to vascular endothelial cells, and, conversely, clones that do not react to DC, but react to vascular endothelial cells, depending on epitopes that the antibodies recognize (Van Den Berg, T K, et. al., Immunology, 88: 294, 1996). It is also assumed that the binding and action of human CD40 antibodies to DC differ depending on epitopes.

It is known that anti-CD40 antibodies or CD40 ligands can suppress the proliferation of CD40-expressing lymphoma cell lines and thus can induce the cell death (Funakoshi S et al., Blood, 83: 2782, 1994; Funakoshi S et al., Journal of Immunotherapy, 19, 93, 1996; Z. H. Zhou et. al., Hybridoma, 18: 471 1999; and Joseph A et al., Cancer Research, 60: 3225, 2000). What is interesting about agonistic antibodies is that the function of the antibody does not always coincide always with that of CD40L. Action to activate B cells does not also coincide with action to suppress B cell tumor growth. It is desired to develop antibodies having both DC-activating ability and tumor cell proliferation-suppressing action. Moreover, among agonistic antibodies, both antibodies that inhibit and those that do not inhibit the binding of CD40L to CD40 are present (Challa A et al., Allergy, 54: 576, 1999). For example, antibodies produced by G28-5 (ATCC No. HB-9110) compete with CD40L, so that there is no effect resulting from the combined use with CD40L. The degree of activation of CD40-expressing cells differs depending on antibodies. Even when antibodies exhibit independently weak agonistic activity, the combined use of the antibodies with CD40 ligands may more significantly promote the activity in the presence of the antibodies, than the activity resulting from CD40 ligands alone. In contrast, even when antibodies exhibit independently agonistic activity, inhibition of CD40 ligands may lower the activity in the presence of the antibodies to a greater extent than the activity resulting from CD40 ligands alone (Pound et al., International Immunology, 11:11, 1999). It was shown that with antibodies that do not compete with CD40 ligands, stronger suppression of proliferation can be achieved in the presence of CD40 ligands, although the tumor cell proliferation-suppressing action of the antibody itself is weak (Joseph A et al., Cancer Research, 60: 3225, 2000). Accordingly, it is desired to develop antibodies that bind to CD40 to suppress independently cell proliferation, but that do not inhibit the binding of CD40 ligands to CD40. By taking full advantage of such characteristics, there is a possibility of developing a therapeutic agent that is more efficient than a soluble CD40L. For example, the soluble CD40L is activated by binding with CD40, and at the same time, it suppresses the function of CD40L present in vivo. An antibody that does not compete with CD40L, does not cause such suppression, and has better therapeutic effects can be expected by synergistic effect.

3. Antagonistic Antibody

In the meantime, as described above, it is expected that because CD40 plays an important role in immune reaction, therapeutic agents for immune suppression upon organ transplantation and against autoimmune disease can be developed by inhibiting the binding of CD40 with its ligand. Sawada-Hase et al., have reported that the proportion of cells strongly expressing CD40 was increased in the peripheral blood monocytes of Crohn's disease patients. However, antibodies that inhibit the binding of CD40 with its ligand have not been well understood For example, such antibodies that inhibit the binding may be effective for the functional analysis of CD40, and therapy against disease, for which activation of CD40 is required. Moreover, antibodies that inhibit CD40 ligands have been also shown to have the potential of being effective as agents against diseases with which the binding of CD40 with CD40 ligands is involved. However, it has been reported that CD40L is expressed in activated blood platelets (V. Henn et. al., Nature 391: 591, 1998). Thus, it has been reported that there is a risk of causing thrombi, if anti-CD40L antibodies are used as a therapeutic agent (T. Kawai et. al., Nat. Medi. 6: 114, 2000). From such a point of view, antibodies against CD40 can be expected to be safer than anti-CD40L antibodies, as an antibody therapeutic agent that inhibits the binding of CD40 with its ligand. Anti-CD40 antibodies are required to suppress the binding of CD40L to CD40, and not to activate CD40 by the antibody itself.

Although a huge number of studies have been conducted in the past concerning antibodies that bind specifically to human CD40 and suppress the binding of CD40L to CD40 without activating CD40, only a single case, that is a mouse anti-human CD40 antibody, named 5D12, has been reported (J. Kwekkeboom et al., Immunology 79: 439, 1993). In addition, it has not been known whether or not antibodies showing neutralization activity for B cells can also show the same for DC that is, if the antibodies can neutralize the action of CD40 ligands. Furthermore, it has been reported that the action of biotinylated anti-mouse CD40 antibodies is enhanced by cross-linking with avidin (Johnson et al., Eur J Immunol, 24: 1835, 1994). We enhanced the action of soluble CD40 ligands against a B cell line (Ramos cells) using antibodies (M2) against tags (FLAG), which had been previously provided by genetic engineering techniques to the soluble ligands, and measured the neutralization activity. Thus, we confirmed that 5D12 (ATCC No. HB-11339) exhibits only slight neutralization activity.

We have newly found that 5D12, an antagonistic antibody, has agonistic activity on its own, as a result of cross-linking even in the absence of CD40L. Conventionally, it has been reported that the action of mouse CD40 antibodies is enhanced by cross-linking of biotin with avidin (Johnson et al., Eur J Immunol, 24: 1835, 1994). Furthermore, it has been known that solid-phasing of CD40 antibodies using anti-immunoglobulin antibodies solid-phased on a plate leads to an increase in activity to suppress the proliferation of tumor cells. This has been thought to be an effect resulting from solid-phasing. However, it has not been known that when anti-immunoglobulin antibodies are added to a culture solution for cross-linking of anti-CD40 antibodies, it may become possible even for antagonistic antibodies to show agonistic activity. If antibodies to be used for therapy have antigenicity, a completely opposite effect may occur, such that antibodies which bind to CD40 antibodies in a human body are produced, and with which CD40 antibodies are cross-linked, so that activity seemingly the same as that of CD40 ligands is produced. Accordingly, in view of the safety of a therapeutic agent, it is very important to keep the antigenicity of antibodies at a low level. Consider a case wherein a therapeutic agent is developed by humanization technology based on the sequence of a variable region of a mouse antibody. Since humanized antibodies are known to have immunogenicity, anti-humanized anti-CD40 antibodies may be produced after administration. Specifically, there may be a risk that the antibodies would become agonistic antibodies. Even if the antigenicity is low, anti-CD40 antibodies may be cross-linked with antibody receptors (FcR). From these points, a preferred antagonistic antibody is a human antibody, which binds specifically to CD40, suppresses the binding of CD40L, and does not activate CD40 even by cross-linking, and exhibits weak binding to FcR.

SUMMARY OF THE INVENTION

As described above, the functions of DC have been increasingly analyzed recently, so that CD40 has begun to be recognized as a gene important in controlling the functions of DC. Starting from this background, the purpose of the present invention is to provide by employing an evaluation system using DC, an anti-human CD40 antibody or a functional fragment thereof, which is substantially antagonistic also to a human CD40 antigen on the dendritic cell (DC) surface, and an agonistic anti-human CD40 antibody or a functional fragment thereof that is expected to have a therapeutic effect higher than that of the conventional anti-human CD40 antibody.

As a result of intensive studies concerning the preparation of antibodies against human CD40, we have completed the present invention by succeeding in producing a novel agonistic antibody and antagonistic antibody that are thought to have a therapeutic effect against disease higher than that of the conventionally known anti-CD40 antibody. That is, the present invention is as follows.

(1) An antibody against a human CD40, or a functional fragment thereof, having at least one property selected from the following properties (a) to (f) of:
(a) acting on dendritic cells to produce IL-12 in the presence of LPS and IFNγ;
(b) having activity to act on dendritic cells causing the cells to mature, which is higher than that of a G28-5 antibody;
(c) having activity to promote an established B cell line to express CD95, which is higher than that of the G28-5 antibody;
(d) having activity to suppress the proliferation of an established B cell line, which is higher than that of the G28-5 antibody;
(e) inducing cell death of an established B cell line; and
(f) not inhibiting the binding of CD40 ligands to CD40.

(2) The above antibody or the functional fragment thereof of the present invention, wherein the maturation of dendritic cells is performed at a concentration of 20 μg/ml or less. In addition, the antibody or the functional fragment thereof promote the established B cell line to express CD95 at the antibody concentration of 20 μg/ml or less. Examples of the established B cell line include Ramos, HS-Sulton or the like.

(3) Furthermore, the above antibody or the functional fragment thereof of the present invention leads to the production of 100 pg/ml or more IL-12 when the antibodies with a concentration of 0.1 μg/ml or more are added to dendritic cells with a concentration of $1 \times 10^6$ cells/ml, and the production of 1000 pg/ml or more, preferably 10000 pg/ml or more IL-12 when the antibodies with a concentration of 1 μg/ml or more are added.

(4) Furthermore, within the antibody concentration range between 0.01 μg/ml and 10 μg/ml, the above antibody or the functional fragment thereof of the present invention, promoting the established B cell line (Ramos cell) to express CD95 with approximately 2 to 3 times or more greater effectiveness than that expressed by a G28-5 antibody as a control. For example, with an antibody concentration of 0.01 μg/ml, the expression is promoted with approximately 2 to 6 times or more greater effectiveness than that expressed by the G28-5 antibody as a control. With an antibody concentration of 0.1 μg/ml, the expression is promoted with approximately 2 to 7 times or more greater effectiveness than that expressed by the G28-5 antibody as a control. With an antibody concentration of 1 μg/ml, the expression is promoted with approximately 2 to 7 times or more greater effectiveness than that expressed by the G28-5 antibody as a control. With an antibody concentration of 10 μg/ml, the expression is promoted with approximately 2 to 6 times or more greater effectiveness than that expressed by the G28-5 antibody as a control.

(5) An antibody or a functional fragment thereof, having the amino acid sequences of a heavy chain variable region and a light chain variable region of an antibody that is produced by a hybridoma KM302-1 (Accession No: FERM BP-7578), KM341-1-19 (Accession No: FERM BP-7759), 2105 (Accession No: FERM BP-8024) or F1-102 (Accession No: ATCC PTA-3337).

| Name | Accession No. | Deposition date | Deposited with: |
|---|---|---|---|
| KM302-1 | FERM BP-7578 | May 9, 2001 | International Patent Organism Depositary, National Institute of Advanced Industrial Science and Technology (Central 6, 1-1-1, Higashi, Tsukuba, Ibaraki, Japan) |
| KM341-1-19 | FERM BP-7759 | Sep. 27, 2001 | |
| 2105 | FERM BP-8024 | Apr. 17, 2002 | |
| F1-102 | ATCC PTA-3337 | Apr. 24, 2001 | American Type Culture Collection (10801 University Blvd. Manassas, Virginia, 20110-2209, U.S.A.) |

(6) An antibody or a functional fragment thereof, having amino acid sequences of the mature portions of a heavy chain variable region and a light chain variable region of the antibody produced by a hybridoma F2-103, which are respectively encoded by plasmid DNAs with Accession Nos.

ATCC PTA-3302 and ATCC PTA-3303; a heavy chain variable region and a light chain variable region of the antibody produced by a hybridoma F5-77, which are respectively encoded by plasmid DNAs with Accession Nos. ATCC PTA-3304 and ATCC PTA-3305; or a heavy chain variable region and a light chain variable region of the antibody produced by a hybridoma F5-157, which are respectively encoded by plasmid DNAs with Accession Nos. ATCC PTA-3306 and ATCC PTA-3307.

| Name | Accession No. | Deposition date | Deposited with: |
|---|---|---|---|
| F2-103 heavy chain (F2-103-H) | ATCC PTA-3302 | Apr. 19, 2001 | American Type Culture Collection (10801 University Blvd. Manassas, Virginia, 20110-2209, U.S.A.) |
| F2-103 light chain (F2-103-L) | ATCC PTA-3303 | Apr. 19, 2001 | |
| F5-77 heavy chain (F5-77-H) | ATCC PTA-3304 | Apr. 19, 2001 | |
| F5-77 light chain (F5-77-L) | ATCC PTA-3305 | Apr. 19, 2001 | |
| F5-157 heavy chain (F5-157-H) | ATCC PTA-3306 | Apr. 19, 2001 | |
| F5-157 light chain (F5-157-L) | ATCC PTA-3307 | Apr. 19, 2001 | |

(7) An antibody or a functional fragment thereof, having amino acid sequences of the mature portions of a heavy chain variable region and a light chain variable region of the antibody produced by a hybridoma KM341-1-19, which are respectively represented by SEQ ID NOS: 28 and 30; a heavy chain variable region and a light chain variable region of the antibody produced by a hybridoma 2105, which are respectively represented by SEQ ID NOS: 32 and 34; a heavy chain variable region and a light chain variable region of the antibody produced by a hybridoma 110, which are respectively represented by SEQ ID NOS: 36 and 38; a heavy chain variable region and a light chain variable region of the antibody produced by a hybridoma 115, which are respectively represented by SEQ ID NOS: 40 and 42; a heavy chain variable region and a light chain variable region of the antibody produced by a hybridoma KM643-4-11, which are respectively represented by SEQ ID NOS: 52 and 54; a heavy chain variable region and a light chain variable region of the antibody produced by a hybridoma F2-103, which are respectively represented by SEQ ID NOS: 60 and 62; or a heavy chain variable region and a light chain variable region of the antibody produced by a hybridoma F5-77, which are respectively represented by SEQ ID NOS: 64 and 66.

(8) An antibody or a functional fragment thereof, having amino acid sequences of the mature portions of a heavy chain variable region and a light chain variable region that are encoded by nucleic acid sequences isolated from a hybridoma KM341-1-19, which are respectively represented by SEQ ID NOS: 27 and 29; a heavy chain variable region and a light chain variable region that are encoded by nucleic acid sequences isolated from a hybridoma 2105, which are respectively represented by SEQ ID NOS: 31 and 33; a heavy chain variable region and a light chain variable region that are encoded by nucleic acid sequences isolated from a hybridoma 110, which are respectively represented by SEQ ID NOS: 35 and 37; a heavy chain variable region and a light chain variable region that are encoded by nucleic acid sequences isolated from a hybridoma 115, which are respectively represented by SEQ ID NOS: 39 and 41; a heavy chain variable region and a light chain variable region that are encoded by nucleic acid sequences isolated from a hybridoma KM643-4-11, which are respectively represented by SEQ ID NOS: 51 and 53; a heavy chain variable region and a light chain variable region that are encoded by nucleic acid sequences isolated from a hybridoma F2-103, which are respectively represented by SEQ ID NOS: 59 and 61; or a heavy chain variable region and a light chain variable region that are encoded by nucleic acid sequences isolated from a hybridoma F5-77, which are respectively represented by SEQ ID NOS: 63 and 65.

(9) An antibody against a human CD40, or a functional fragment thereof, having at least one property selected from the following properties (g) to (j) of:

(g) neutralizing the action of ligands on CD40;

(h) neutralizing or alleviating one or more effects that ligands, which are for CD40 on an established B cell line, have on CD40-expressing cells, and having agonistic action on CD40 on the above established B cell line weaker than that of 5D12 due to cross-linking by anti-immunoglobulin antibodies;

(i) alleviating or neutralizing the action of CD40 ligands on the established B cell line to increase CD95 expression; and (j) having antagonistic action on CD40 expressed on dendritic cells.

(10) The antibody or the functional fragment of (9) above can suppress the expression of CD95 in Ramos cells to a level approximately 10% or less than that of a control, when antibodies with a concentration of 0.1 μg/ml are added to the Ramos cells with a concentration of $1 \times 10^6$ cells/ml supplemented with a saturated amount of CD40L-expressing cells; can suppress the expression of CD95 in Ramos cells to the same level as that of a negative control, when the antibodies with a concentration of 1 μg/ml are added; and can suppress the expression of CD95 in the Ramos cells to the same level as that of the negative control, when the antibodies with a concentration of 10 μg/ml are added.

(11) The antibody or the functional fragment thereof of (9) above, wherein the proliferation of tonsillar B cells is suppressed in vitro by approximately 80 to 95% or more, when the antibodies with a concentration between 0.001 μg/ml and 10 μg/ml are added to $1 \times 10^5$ tonsillar B cells supplemented with soluble CD40L (1 μg/ml). For example, when the antibodies with a concentration between 0.01 μg/ml and 10 μg/ml are added, the proliferation of tonsillar B cells is suppressed by approximately 95% or more. In particular, when the antibodies with a concentration of 0.001 μg/ml are added, the proliferation of tonsillar B cells is suppressed by approximately 80% or more.

(12) An antibody or a functional fragment thereof, having amino acid sequences of a heavy chain variable region and a light chain variable region of the antibody produced by a hybridoma KM281-1-10 (Accession No: FERM BP-7579), 4D11 (Accession No: FERM BP-7758) or F4-465 (Accession No. ATCC PTA-3338). Deposited biological material covered by the issued claims in the patent granted from this application will be made available to the public in accordance with 37 C.F.R. § 1.808.

| Name | Accession No. | Deposition date | Deposited with: |
|---|---|---|---|
| KM281-1-10 | FERM BP-7579 | May 9, 2001 | International Patent Organism Depositary, |
| 4D11 | FERM BP-7758 | Sep. 27, 2001 | National Institute of Advanced Industrial Science and Technology (Central 6, 1-1-1, Higashi, Tsukuba, Ibaraki, Japan) |
| F4-465 | ATCC PTA-3338 | Apr. 24, 2001 | American Type Culture Collection (10801 University Blvd. Manassas, VA 20110-2209, U.S.A.) |

(13) An antibody or a functional fragment thereof, having amino acid sequences of the mature portions of a heavy chain variable region and a light chain variable region of the antibody produced by a hybridoma KM281-1-10, which are respectively represented by SEQ ID NOS: 44 and 46; a heavy chain variable region and a light chain variable region of the antibody produced by a hybridoma 4D11, which are respectively represented by SEQ ID NOS: 48 and 50; or a heavy chain variable region and a light chain variable region of the antibody produced by a hybridoma F4-465, which are respectively represented by SEQ ID NOS: 56 and 58.

(14) An antibody or a functional fragment thereof, having amino acid sequences of the mature portions of a heavy chain variable region and a light chain variable region that are encoded by nucleic acid sequences isolated from a hybridoma KM281-1-10, which are respectively represented by SEQ ID NOS: 43 and 45; a heavy chain variable region and a light chain variable region of an antibody produced by a hybridoma 4D11, which are respectively represented by SEQ ID NOS: 47 and 49; or a heavy chain variable region and a light chain variable region that are encoded by nucleic acid sequences isolated from a hybridoma F4-465, which are respectively represented by SEQ ID NOS: 55 and 57.

(15) Examples of the antibody or the functional fragment thereof of (1) to (14) above include human antibodies.

(16) A pharmaceutical composition, containing as an active ingredient the antibody or the functional fragment thereof of any one of (1) to (15) above.

(17) An immunopotentiating agent, anti-tumor agent or anti-autoimmune disease agent, containing as an active ingredient the antibody or the functional fragment thereof of any one of (1) to (8) above.

(18) An immunosuppressive agent, anti-autoimmune disease agent, therapeutic agent against allergies or therapeutic agent against blood coagulation factor VIII-inhibiting syndrome, containing as an active ingredient the antibody or the functional fragment thereof of any one of (9) to (14) above.

(19) Here, an epitope of a human CD40 that the monoclonal antibody of the present invention recognizes can be determined by a known method, such as by examining the binding to overlapping synthetic oligopeptides obtained from the primary amino acid sequence of human CD40 (e.g., Ed Harlow and David Lane (eds.), *Antibodies: A Laboratory Manual*, 1988 Cold Spring Harbor Laboratory Press; U.S. Pat. No. 4,708,871). A peptide library kit with the phage display process (New England BioLabs) can also be used for epitope mapping. The present invention also encompasses an antibody or a functional fragment thereof that recognizes a novel epitope of human CD40 that the antibody or the functional fragment thereof produced by each of the above hybridomas recognizes.

(20) The present invention further provides a nucleic acid (RNA or cDNA) encoding at least the variable region of a heavy chain and/or light chain of an antibody isolated from each of the above hybridomas, a vector containing the nucleic acid, and a host cell carrying the nucleic acid.

The present invention will be described in detail. This specification includes part or all of the contents as disclosed in the specification and/or drawings of PCT Application PCT/US01/13672 (filed on Apr. 27, 2001), Japanese Patent Application No. 2001-142482 (filed on May 11, 2001), Japanese Patent Application No. 2001-310535 (filed on Oct. 5, 2001), and U.S. Patent Application U.S. Ser. No. 10/040,244 (filed on Oct. 26, 2001) which are priority documents of the present application.

As described later, we have found that a known monoclonal antibody 5D12 (ATCC No. HB-11339) that is antagonistic to CD40 on B cells is not antagonistic to CD40 on DC. We have further found that many monoclonal antibodies show agonistic activity on their own as a result of cross-linking by anti-immunoglobulin antibodies, even if they are antagonistic antibodies that block the action of CD40L.

1. Definition

The terms used in this specification are defined as follows.

The term "human CD40" in the present invention means a polypeptide having an amino acid sequence shown by Clark et al. (E. A. Clark et al., Proc. Natl. Acad. Sci. USA 83: 4494, 1986) or Stamenkovic et al. (I. Stamenkovic et al., EMBO J. 8: 1403, 1989). Specifically, the human CD40 is an antigen polypeptide that is expressed on the surface of a B cell, DC, macrophage, endothelial cell, epithelial cell or tumor cells of these cells.

The term "anti-CD40 monoclonal antibody" means any monoclonal antibody against CD40 expressed by a cell, full-length CD40 or partial length CD40. A more preferred anti-CD40 monoclonal antibody binds to the extracellular portion of CD40 and provides agonistic or antagonistic action on the cells expressing CD40.

Furthermore, the term "antibody" in the present invention is derived from a gene (generically called an "antibody gene") encoding a heavy chain variable region, a heavy chain constant region, a light chain variable region and a light chain constant region composing an immunoglobulin. The antibody of the present invention encompasses an antibody that is of any immunoglobulin class and has any isotype. The term "functional fragment" of the antibody in the present invention is a part (a partial fragment) of an antibody as defined above, and means a fragment retaining one or more actions of the antibody on an antigen. Specific examples of such functional fragment include F(ab')$_2$, Fab', Fab, Fv, FVs with disulfide bond, single-stranded FV(scFV), and polymers thereof (D. J. King., Applications and Engineering of Monoclonal Antibodies., 1998 T. J. International Ltd).

The term "human antibody" in the present invention means an antibody which is the expression product of a human-derived antibody gene.

The term "agonistic" means an action to promote the binding of CD40 ligands to CD40 expressed on the surfaces of cells such as B cells, tumor cells or dendritic cells, or an action to provide CD40-expressing cells with one or more effects that are provided by CD40 ligands to CD40-expressing cells. The term "agonistic antibody" means an antibody having such an agonistic action.

The term "antagonistic" means an action to inhibit the binding of CD40 ligands to CD40 expressed on the surfaces of cells such as B cells, tumor cells or dendritic cells, or an action to neutralize one or more effects that are provided by CD40 ligands to CD40-expressing cells. The term "antagonistic antibody" means an antibody having such an action.

The term "dendritic cells (DC)" in the present invention indicates a group of cells which are also referred to as dendritic leukocytes having a strong antigen-presenting function. Dendritic cells used herein are induced by culturing CD34 positive precursor cells contained in, for example, bone marrow, umbilical cord blood or peripheral blood. Alternatively, the dendritic cells can be obtained by culturing CD14 positive monocytes in peripheral blood in the presence of GM-CSF and IL-4.

The term "immature DC" means DC that are CD14 negative, CD1a strongly positive, CD83, CD86 positive, and MHC class II positive.

The term "mature DC" means DC that are CD14 negative, CD1a positive, and have become CD83, CD86 and MHC class II strongly positive.

The term "activate DC" in the present invention means a change that DC induce by responding to the stimulation by CD40. For example, it also means to cause the maturation of immature DC, the high expression of CD80, CD86 and HLA-Class II, and the enhancement of IL-12 production. Alternatively, when T cells co-exist, it also means to stimulate T cells to promote their proliferation.

The term "activate B cells and a B cell line" in the present invention means a change that cells induce by responding to the stimulation by CD40. For example, it means to cause DNA synthesis, promote the incorporation of thymidine, and thus to increase the expression amount of CD95.

2. Obtainment of Antibody

To obtain the antibody of the present invention, it is preferred to immunize mice using as an antigen a gene recombinant mouse cell line expressing a human CD40 or a soluble human CD40 that has been produced and purified with recombinants. Mice to be used for immunization are preferred to produce human antibodies (Tomizuka. et al., Proc Natl Acad Sci USA., 2000 Vol 97: 722). By selecting monoclonal antibodies that bind to soluble human CD40 that has been produced and purified with recombinants, antibodies that react also to CD40 expressed on cells other than B cells may be more easily obtained than by a case wherein clones reacting specifically to B cells are selected. Hybridomas can be produced by the method of Kohler and Milstein et al. (Nature, 1975 Vol. 256: 495) generally used in monoclonal antibody production using the lymphnode cells or splenocytes of immunized mice.

Furthermore, the binding of soluble CD40L to CD40 is analyzed using a surface plasmon resonance system such as BIAcore 2000 (Biacore), and then antibodies that do not compete with CD40L are selected. In addition, antibodies that suppress independently the suppression of the cell growth of B lymphoma are selected. Furthermore, antibody selection is performed using the condition of whether or not they act on DC as an indicator. This enables the production and selection of antibodies with advantages of acting on dendritic cells or B cells without competing with CD40L, and suppressing the proliferation of CD40-expressing cancer cells.

The antibody of the present invention is obtained by culturing the thus obtained hybridoma. Further, a gene encoding a human monoclonal antibody or a variable region thereof is cloned from an antibody-producing cell such as a B cell or a hybridoma, the cloned gene is incorporated into an appropriate vector, and then the vector is introduced into a host (e.g., a mammalian cell line, *Escherichia coli*, yeast cell, insect cell or plant cell), so that a recombinant antibody produced by gene recombination technology can be prepared (P. J. Delves., ANTIBODY PRODUCTION ESSENTIAL TECHNIQUES., 1997 WILEY, P. Shepherd and C. Dean., Monoclonal Antibodies., 2000 OXFORD UNIVERSITY PRESS; J. W. Goding., Monoclonal Antibodies: principles and practice., 1993 ACADEMIC PRESS). Moreover, transgenic cattle, goat, sheep or pigs, wherein a target antibody gene is incorporated into the endogenous gene by transgenic animal generation techniques are generated. From the milk of these transgenic animals, monoclonal antibodies derived from the antibody gene can be obtained in large quantities. When hybridomas are cultured in vitro, they are grown, maintained and stored in a way suitable for various conditions such as the properties of cell species to be cultured, purposes of experiments and studies, and culturing methods. Then, hybridomas can be cultured using any nutrient medium that is induced and prepared from a known nutrient medium or known basic medium that is used for the production of monoclonal antibodies in the culture supernatant.

3. Screening

Screening for agonistic antibodies is performed by analysis using human B lymphoma, so that antibodies that promote CD95 expression can be selected. Antibodies are further added to a purified DC culture solution, and then antibodies causing maturation are selected. Alternatively, antibodies showing activity to proliferate T cells in a mixed-lymphocyte reaction using immature DC are selected. Furthermore, antibodies are added to mature DC, and then antibodies having action to promote IL-12 production are selected. Furthermore, antibodies having activity to suppress the growth of tumor cells expressing CD40 or activity to induce cell death of the tumor cells are selected. Competition with CD40L can be distinguished from other cases based on whether or not the antibody inhibits the binding of soluble CD40 with soluble CD40 ligands using, for example, a surface plasmon resonance system (BIOCore). Alternatively, it can also be distinguished from other cases based on whether or not the antibody enhances the action of CD40 ligands on a B cell line.

Screening for antagonistic antibodies is performed by analysis using human B lymphoma. Further addition of soluble CD40L having FLAG as a tag in the presence of anti-FLAG antibody enables screening for antibodies that inhibit more strongly the binding of soluble CD40L to CD40 on the human B lymphoma cell. By the introduction of a gene encoding CD40L instead of soluble CD40L, it is also possible to use recombinant cells expressing many CD40 ligands on the cell surface. Subsequently, human antibodies are cross-linked with anti-human IgG antibodies, so that clones that activate B lymphoma by cross-linking are removed. Furthermore, antibodies showing activity to suppress the T cell proliferation in a mixed-lymphocyte reaction using purified and matured DC, or antibodies having action to suppress IL-12 production when CD40 ligands are added to mature DC are selected.

Antibodies that are obtained as described above have at least any of the following properties that are thought to be therapeutically effective.

(1) In the Case of Agonistic Antibody (a) The antibody acts on dendritic cells to cause IL-12 production in the presence of LPS (lipopolysaccharide) and IFNγ. The LPS concentration in this case ranges from 10 pg/ml to 10 ng/ml and the IFNγ concentration ranges from $10^{-4}$ M to $10^{-2}$ M. With an antibody concentration of 1 μg/ml or more, or preferably 0.1 μg/ml or more, the production amount of IL-12 is greater than that in a test using a G28-5 antibody as a control, the known agonistic anti-CD40 antibody. When the antibodies with a concentration of 0.1 μg/ml or more are added to dendritic cells with a concentration of $1\times10^6$ cells/ml, 100 pg/ml or more IL-12 is produced, or when the same with a concentration of 1 μg/ml or more are added, 1,000 pg/ml or more, or preferably, 10,000 pg/ml or more IL-12 is produced (see Examples 9 and 13).

(b) The antibody has action of binding to dendritic cells and thus to cause the maturation of the dendritic cells. Moreover, when the antibodies with a concentration of 20 μg/ml or less, preferably 0.1 to 15 μg/ml; further preferably 5 to 15 μg/ml were cultured with dendritic cells, the activity to cause maturation is higher than that of the G28-5 antibody (see Example 9).

(c) The antibody has activity to promote CD95 expression of an established B cell line, which is greater than that of the G28-5 antibody. In this case, with an antibody concentration of 10 μg/ml or more, preferably 1 μg/ml or more, further preferably 0.1 μg/ml or more, still further preferably 0.01 μg/ml or more, and most preferably 0.001 μg/ml or more, the activity to promote CD95 expression is higher than that of the G28-5 antibody that is used as a control in a test. The ratios of the activity of the G28-5 antibody, which was used in a test as a control, to promote CD95 expression to the same of the antibody with concentrations of 10 μg/ml, 1 μg/ml, 0.1 μg/ml and 0.01 μg/ml are as shown below (Table 1).

TABLE 1

| Antibody concentration | Ratio |
| --- | --- |
| 10 μg/ml | Approximately 2-fold, preferably approximately 3-fold, more preferably 4.5-fold, and further preferably 6-fold |
| 1 μg/ml | Approximately 2-fold, preferably approximately 5-fold, more preferably approximately 6-fold, and further more preferably 7-fold |
| 0.1 μg/ml | 2-fold, preferably 6-fold, more preferably approximately 7-fold |
| 0.01 μg/ml | 2-fold, preferably 4-fold, more preferably 5-fold, further preferably approximately 6-fold |

The promoted expression of CD95 means that the antibody activates the established B cell line. Here, examples of the established B cell line include Ramos cells and HS-Sulton cells. In addition, Ramos cells are of Burkitt's lymphoma, which are model cells of human centroblastic B cells. HS-Sulton cells are of Burkitt's lymphoma (see Examples 6 and 12).

(d) The antibody has activity to suppress the DNA synthesis, thymidine incorporation, and proliferation of the established B cell line (Ramos cells or HS-Sulton cells), which is higher than that of G28-5 antibody. The antibody concentration in this case is at least 0.05 μg/ml, or preferably 0.1 to 15 μg/ml (see Example 8).

(e) The antibody induces cell death of the established B cell line (see Example 16).

(f) The antibody does not inhibit the binding of CD40 ligands to CD40. The term "does not inhibit" means that CD40L can bind to CD40 to the same degree as that when the antibody is absent, even when the antibody previously binds to CD40 (that is, in the presence of the antibody). Either one of or both CD40 ligands and CD40 may be a type of a protein that is expressed on the membrane or a soluble protein (see Example 11).

Antibodies having the above properties are produced, for example, by a hybridoma KM302-1 (FERM BP-7578) and a hybridoma KM341-1-19 (FERM BP-7759).

The nucleotide sequences and amino acid sequences of the heavy chain (H chain) and light chain (L chain) variable regions of a monoclonal antibody produced by the hybridoma KM341-1-19 were determined (Example 17). The present invention provides DNA encoding at least the heavy chain variable region, or the full-length heavy chain, and DNA encoding the light chain variable region of the monoclonal antibody produced by the hybridoma KM341-1-19. The DNAs also include other DNAs encoding the same amino acid sequences due to codon degeneration in addition to those described in Example 17. Moreover, the present invention provides monoclonal antibodies or functional fragments thereof as specified by the amino acid sequences of at least the heavy chain variable regions or the amino acid sequences of the full-length heavy chains, and the amino acid sequences of the light chain variable regions, as disclosed in Example 17.

(2) In the Case of Antagonistic Antibody (g) The antibody neutralizes the action of ligands for CD40. Here, the term "the action of ligands" means both the action of ligands expressed on T cells or other cells, and the action of free ligands for CD40 (see Examples 7 and 14).

(h) The antibody neutralizes one or more effects that ligands for CD40 on the established B cell line have on CD40-expressing cells, and do not show agonistic action to CD40 on the above established B cell line by cross-linking by anti-immunoglobulin antibodies. This action is weaker than that of 5D12. The "effects that ligands have on CD40-expressing cells" mean the activation of the CD40-expressing cells. Specifically in B cells, the effect means the activation of thymidine incorporation and B cell proliferation, and the activation of the enhanced expression of CD95 in the established B cell line. Furthermore, in DC, the effect means the activation of DC maturation, the activation of the enhanced expression of CD86 and HLA-DR, the activation of thymidine incorporation by the co-existing T cells, the promotion of the proliferation, the activation of IL-12 and IL-10 production, and the like. Cross-linking by anti-immunoglobulin antibodies is performed by causing the presence of 0.1 μg/ml or more of anti-immunoglobulin antibodies in a culture solution (see Example 7).

(i) The antibody alleviates or neutralizes the activity of cross-linked CD40L or CD40L expressed by cells to enhance the expression of CD95 in the established B cell line. The antibody also alleviates or neutralizes the activity of CD40L, the action of which is enhanced by cross-linking by antibodies and the like against tags. The binding of ligands (including both free ligands and ligands expressed by specific cells) for CD40 to CD40-expressing cells causes intracellular signal transduction, and finally causes the cells to express CD95 (Fas) on the cell surfaces. Accordingly, the antagonistic antibody of the present invention inhibits the above signal transduction by binding to CD40, thereby neutralizing the expression of CD95. The antibody concentration in this case is 1 μg/ml or more, or preferably 0.1 μg/ml or more (see Examples 7 and 14).

(j) The antibody is antagonistic to CD40 on DC. Specifically, the antibody alleviates or neutralizes the activity of CD40L to activate DC. When DC are stimulated by ligands on T cells co-existing with the DC, T cells are activated, so that thymidine incorporation and the like are promoted. In the mixed-lymphocyte reaction, wherein DC and T cells that are both derived from different individuals are allowed to co-exist, DC interact with T cells, thereby causing T-cell activation. The antagonistic antibody of the present invention inhibits the above interaction by binding to CD40, resulting in suppressed incorporation of thymidine. The antibody concentration in this case is at least 0.001 µg/ml, or preferably 0.1 to 10 µg/ml (see Example 10).

The above antagonistic antibody is produced by, for example, hybridomas KM281-1-10 (FERM BP-7579) and KM281-2-10-1-2 (FERM BP-7580) (May 9, 2001, the International Patent Organism Depositary (IPOD) at the National Institute of Advanced Industrial Science and Technology (Central 6, 1-1-1, Higashi, Tsukuba, Ibaraki) and 4D11 (FERM BP-7758).

(3) The antibody of the present invention can be altered to an antibody of a different subclass (for example, see EP314161 publication), by modification by genetic engineering techniques known by a person skilled in the art, specifically by substituting a region that defines the subclass of an antibody heavy chain with a region that defines another subclass. A heavy chain variable region and the constant region of another subclass can be directly linked. For example, an alteration of the subclass of the antibody of the present invention to IgG2 or IgG4 makes it possible to lower the binding degree of the antibody to a Fc receptor. Specifically, NheI site (GCTAGC) is introduced into a human antibody heavy chain, EU index 118 (Ala), 119 (Ser) site according to Kabat et al (Sequence of Proteins of Immunological Interest, 5$^{th}$ Ed. Public Health Service, National Institute of Health, Bethesda, Md. (1991)). By digestion using the restriction enzyme, switching to another subclass, IgG, can be performed without altering the amino acid. Moreover, artificial alteration of the amino acid sequence of a constant region, or the binding of a constant region sequence having such an altered sequence with the variable region of the antibody of the present invention can lower the binding degree to a Fc receptor (Lund J., et al., J. Immunol. 1991 vol 147: 2657-2662), or can also increase or decrease CDC activity (Tao M., et al., J. Exp. Med. 1991 vol 1025–1028, Idusogie E E., et al., J. Immunol. 2001 vol 166: 2571–5). Furthermore, to avoid the action of ADCC, CDC or the like, only IgG2 or IgG4 subclass antibodies can be previously selected. In addition, the binding of a radionuclide, bacterial toxin, chemotherapeutant, prodrug or the like with the antibody of the present invention can further enhance the therapeutic effect against disease such as cancer.

4. Pharmaceutical Composition

A pharmaceutical composition containing a pharmaceutical preparation that is the purified antibody of the present invention is also encompassed by the scope of the present invention. Such a pharmaceutical composition preferably contains a physiologically acceptable diluent or carrier in addition to the antibody, or may be a mixture with other antibodies or other drugs, such as antibiotics. Examples of the appropriate carrier include, but are not limited to, a physiological saline solution, a phosphate buffered saline solution, a phosphate buffered saline glucose solution and a buffered physiological saline. Alternatively, the antibody is freeze-dried, and then used when necessary by adding the above buffered aqueous solution for reconstruction. Examples of the route of administration include an oral route and a parenteral route including intravenous, intramuscular, hypodermic and intraperitoneal injections or drug delivery.

In this case, the effective dose to be administered as a combination of the effective dose of the antibody of the present invention, an appropriate diluent, and a pharmacologically acceptable carrier ranges from 0.1 mg to 100 mg per kg of body weight per administration. Administration is performed at intervals of 2 days to 8 weeks.

When a pharmaceutical composition containing the antibody of the present invention is used, and particularly, when the agonistic antibody is used, the composition is used as an immunopotentiating drug (anti-viral agent and anti-infective drug), anti-tumor agent or anti-autoimmune disease agent. Multiple examples of these diseases may occur together. Alternatively, the antibody can also be used as an adjuvant in combination with a vaccine such as a cancer-specific peptide. When the composition contains the antagonistic antibody, it is useful as an immunosuppressive agent (prophylactic or therapeutic agent against immunological rejection or GVHD upon transplantation of islets of Langerhans, kidneys or the like) upon organ transplantation, or an anti-autoimmune disease agent (e.g., against rheumatism, or as a therapeutic agent against arterial sclerosis, disseminated sclerosis, systemic erythematodes, idiopathic thrombocythemia or Crohn's disease), therapeutic agent against allergies such as asthma, or therapeutic agent against blood coagulation factor VIII-inhibiting syndrome. Multiple examples of these diseases may occur together.

When the anti-CD40 antibody is used as a therapeutic means against a disease in which CD40 is involved, it can be expected that antibodies providing a better therapeutic effect can be obtained by selecting the antibodies using the function of DC as an indicator.

In the case of the agonistic antibody, it can be expected that antibodies having strong immunopotentiation action can be obtained by selecting antibodies that can activate DC more effectively. Furthermore, by using the promotion of IL-12 production by mature DC as an indicator, antibodies having strong CTL-inducing action can be obtained. By the CTL induction, antibodies that are highly effective for removing cells infected with viruses or tumor cells can be obtained. Moreover, since synergistic effects can be expected, preferred antibodies bind to CD40 without inhibiting the binding of CD40 ligands to CD40. When cancer treatment is considered, if antibodies that directly induce cell death of CD40-expressing cancer cells or suppress their proliferation, and effectively activate DC are present, synergistic effects are expected therefrom, and such antibodies can be a therapeutic agent that can be used against tumors that do not express CD40. These antibodies are considered to be useful as a therapeutic agents against viral diseases or anti-tumor agents.

In the meantime, antibodies that specifically bind to CD40 and suppress the binding of CD40L without activating CD40 are also expected to be able to suppress not only the action of ligands for B cells, but also the action on DC. However, antibodies have been so far obtained using as an indicator their effect on B cells. Thus, it is highly significant to obtain antibodies that have strong suppressive action also on dendritic cells and to develop them as a pharmaceutical product. Further, it is a concern that the anti-CD40 antibody can have a totally opposite action by cross-linking as described above. Thus, antibodies that do not activate CD40 even by cross-linking are required. It is also a concern that monoclonal antibodies derived from a non-human mammal such as a mouse, chimeric antibodies consisting of the variable region of a mouse monoclonal antibody and a constant region of a human immunoglobulin and humanized antibodies resulting from CDR grafting, which have been so far reported as antibodies against human CD40, have antigenicity. Therefore, a human antibody is desirable as an antibody to inhibit the binding with CD40 ligands.

BEST MODE FOR CARRYING OUT THE INVENTION

Figure 1:
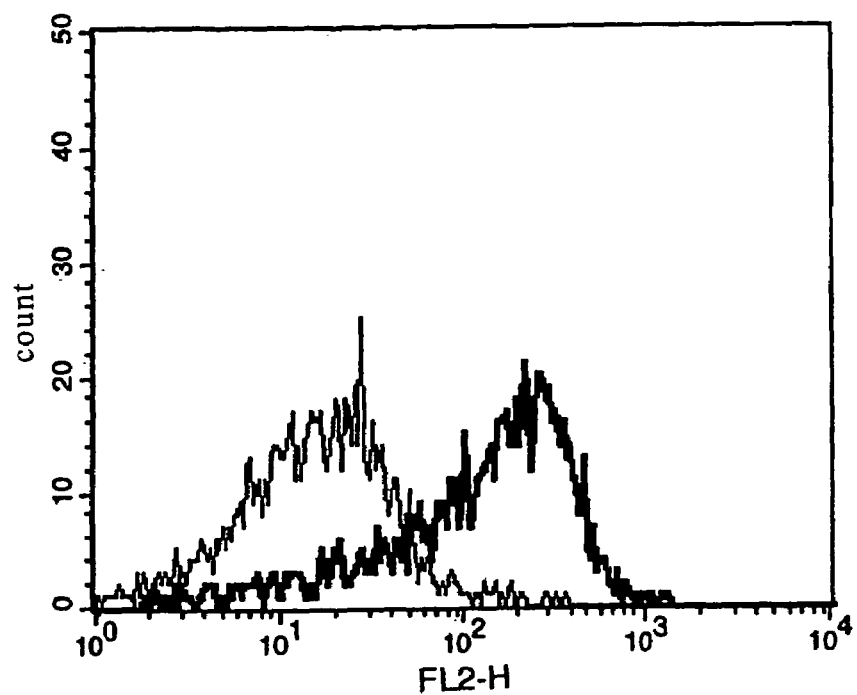
FIG. 1 shows that KM302-1 antibodies promoted CD95 expression.
Figure 1:
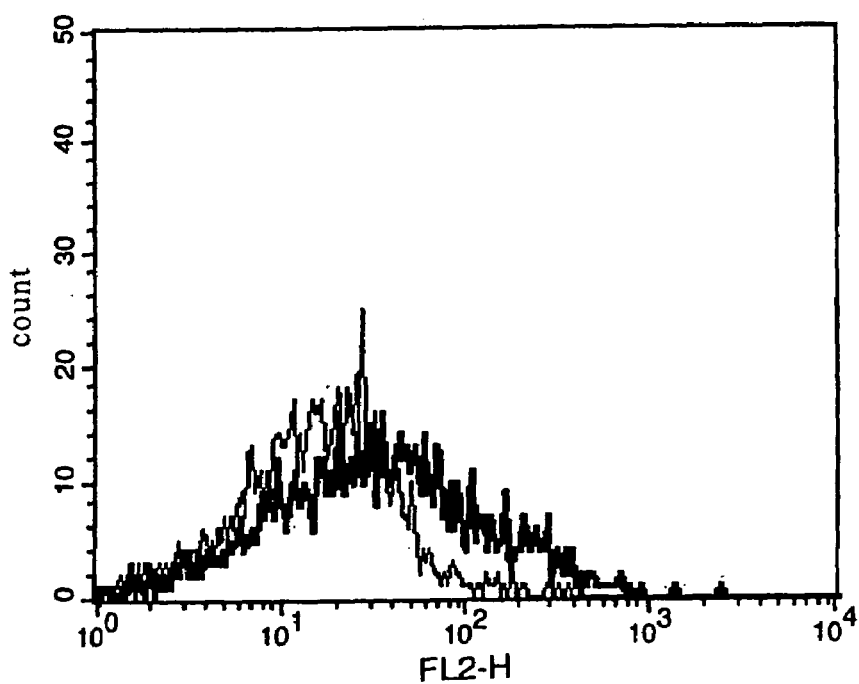

The present invention will be further described in detail by referring to the examples. However, the technical scope of the invention is not limited by these examples.

EXAMPLE 1

Preparation of Antigen (1) Cell

EL-4 cells are of a mouse-derived established T cell line, and can be easily obtained (ATCC No.: TIB-39). Ramos B cells (ATCC No.: CRL-1596) and mouse anti-CD40 antibody-producing hybridoma G28-5 (HB-9110) and 5D12 (HB-11339) were purchased from ATCC.

(2) Expression and Purification of Antigen

Extracellular regions were amplified by PCR using human CD40 cDNA (Genbank Accession Number: NM_001250) as a template and the following primers under conditions of 20 cycles of 95° C. for 5 seconds, 55° C. for 30 seconds and 72° C. for 30 seconds.

```
Primer 1: 5'-CCCAGATCTGTCCATCCAGAACCACCCACTGCATGCAGAG-3'  (SEQ ID NO: 1)
Primer 2: 5'-ACAAGATCTGGGCTCTACGTATCTCAGCCGATCCTGGGGAC-3'  (SEQ ID NO: 2)
```

The amplified cDNA was inserted following the melittin signal sequence and before the human IgG1-derived FC or mouse IgG2a-derived FC region of a pFastBac vector (Gibco BRL). To produce CD40, recombinant baculoviruses were prepared according to the instruction. Th5 cells were infected with the recombinant viruses, and then cultured for 4 days. The supernatant was treated with a 0.22 nm filter, ProteinG sepharose (Amersham Pharmacia) was added thereto, and then the mixture was gently shaken at 4° C. After one night, sepharose was transferred to a column and then washed with a 20× volume of PBS. A human CD40 FC protein was eluted with a 20 mM glycine buffer (pH 3.0). The vector to express CD40 on cell surfaces was obtained from Randolph J. Noelle (Inui, S et al., EJI, 20, 1747–1753, 1990). The full-length cDNA was cleaved with the XbaI enzyme, and then inserted into pcDNA3 (INVITROGEN). The vector was introduced into EL-4 cells, and then the cells were cultured in the presence of 0.5 mg/ml G418 (Gibco BRL), thereby obtaining a stable expression strain. The expression of CD40 was confirmed by FACS analysis using FITC-conjugated anti-human CD40 antibodies (Pharmingen).

EXAMPLE 2

Generation of Mice for Immunization

The mice used for immunization had a genetic background whereby they were homozygotes for both disrupted endogenous Ig heavy chain and κ light chain, and the mice harbored at the same time chromosome 14 fragment (SC20) containing human Ig heavy chain gene locus, and human Igκ chain transgene (KCo5). These mice were generated by crossing mice of a line A having a human Ig heavy chain gene locus with mice of a line B having a human Igκ chain transgene. The mice of line A are homozygous for both disrupted endogenous Ig heavy chain and κ light chain, and harbor chromosome 14 fragment (SC20), which is transmittable to progeny, as is described, for example, in the report of Tomizuka et al. (Tomizuka. et al., Proc Natl Acad Sci USA., 2000 Vol 97: 722). The mice of the line A were immunized, so that the following hybridomas F2-103 and F5-77 were obtained. Furthermore, the mice of line B (transgenic mice) are homozygotes for both disrupted endogenous Ig heavy chain and κ light chain, and harbor a human Igκ chain transgene (KCo5), as described, for example, in the report of Fishwild et al. (Nat Biotechnol., 1996 Vol 14:845).

Individuals obtained by crossing male mice of the line A with female mice of the line B, or female mice of the line A with male mice of the line B, and having human Ig heavy chain and κ light chain detected simultaneously in the sera (Ishida & Lonberg, IBC's 11th Antibody Engineering, Abstract 2000) were used for the following immunization experiment. In addition, the above human antibody-producing mice are available from Kirin Brewery Co., Ltd via contract. By immunizing the above mice, the following hybridomas KM302-1, KM341-1-19, KM643-4-11, 2053, 2105, 3821, 3822, 285, 110, 115, KM281-1-10, KM281-2-10-1-2, KM283-5, KM292-1-24, KM225-2-56, KM341-6-9, 4D11, 5H10, 11E1, 5G3, 3811, 3411 and 3417 were obtained. Moreover, chimeric mice (Kuroiwa et al., Nat Biotechnol., 2000 vol 18:1086) harboring human antibody Lambda chain reported by Kuroiwa et al. were also used for the following immunization experiment. A hybridoma F4-465 was obtained from the mouse.

EXAMPLE 3

Preparation of Human Monoclonal Antibody Against Human CD40

Monoclonal antibodies in this example were prepared according to a general method described in the Introduction of Experimental Procedures for Monoclonal Antibodies (written by Tamie ANDO et al., KODANSHA, 1991). The human CD40 used as an immunogen herein were the human CD40 human FC and CD40-expressing EL-4 cells prepared in Example 1. Animals used herein for immunization were human antibody-producing mice that produce the human immunoglobulin prepared in Example 2.

The human antibody-producing mice were immunized with 2 to 100 μg/immunization of CD40: hFc per mouse. Excluding the first immunization, an antigen solution was mixed with an equivalent volume of Freund's incomplete adjuvant (Sigma), and then injected subcutaneously into several separate positions. Immunization was performed 3 to 4 times approximately every 10 days to 3 weeks. For the first immunization, Freund's incomplete adjuvant (Sigma) was used. Blood was collected from the mouse tail, and then human antibody γ and κ against CD40 in the serum were measured using ELISA. 3 to 4 days before excision of the spleen, final immunization was performed by injecting 20 μg of CD40: Fc dissolved in PBS via the caudal vein.

The human antibody-producing mice were immunized with human CD40-expressing mouse EL-4 cells. EL-4 cells ($10^8$ cells/ml) were suspended in PBS, and then gently mixed with an equivalent volume of RIBI adjuvant previously emulsified with PBS. Immunization was performed with the cells 3 to 5 times approximately every 10 days to 3 weeks. When the adjuvant was not used, the cells were irradiated with X-rays with 8000 rad for use.

The spleen was surgically obtained from the immunized mice. The collected splenocytes were mixed with mouse myeloma SP2/0 (ATCC No.: CRL1581) at a ratio of 5 to 1. The cells were fused using polyethylene glycol 1500 (Boehringer Mannheim) as an agent for cell fusion, thereby preparing a large number of hybridomas. The selection of hybridomas was performed by culturing in HAT-containing DMEM media (Gibco BRL) supplemented with 10% fetal calf serum (FCS), hypoxanthine (H), aminopterin (A) and thymidine (T). Furthermore, single clones were obtained by the limiting dilution method using HT-containing DMEM media. Culturing was performed in a 96-well microtiter plate (Beckton Dickinson). Screening for hybridoma clones producing anti-human CD40 human monoclonal antibodies was performed by measurement using enzyme-linked immuno adsorbent assay (ELISA) and fluorescence activated cell sorter (FACS), as described later in Example 4.

Screening for the human monoclonal antibody-producing hybridoma by ELISA was performed by 3 types of ELISA and FACS analyses as described below. Thus, a large number of hybridomas producing human monoclonal antibodies that had human immunoglobulin γ chain (hIgγ) and human immunoglobulin light chain κ, and had reactivity specific to human CD40 were obtained. In any of the following examples including this example, and tables and figures showing the test results of the examples, each hybridoma clone producing the human anti-human CD40 monoclonal antibody of the present invention was denoted using symbols. A clone represented by the symbols followed by "antibody" means an antibody that is produced by each of the hybridomas, or a recombinant antibody that is produced by a host cell carrying an antibody gene (full-length or a variable region) isolated from the hybridoma. In addition, within a contextually clear range, the name of a hybridoma clone may express the name of an antibody.

The following hybridoma clones represent single clones.

Agonistic Antibody:

KM302-1, KM341-1-19, KM643-4-11, 2053, 2105, 3821, 3822, 285, 110, 115, F1-102, F2-103, F5-77 and F5-157

Antagonistic Antibody:

KM281-1-10, KM281-2-10-1-2, KM283-5, KM292-1-24, KM225-2-56, -KM341-6-9, 4D11, 5H10, 11E1, 5G3, 3811, 3411, 3417 and F4-465

3 hybridoma clones KM 302-1, KM 281-1-10 and KM 281-2-10-1-2 among them were deposited on May 9, 2001, clones KM341-1-19 and 4D11 were deposited on Sep. 27, 2001, and clone 2105 was deposited on Apr. 17, 2002, with the International Patent Organism Depositary at the National Institute of Advanced Industrial Science and Technology (Central 6, 1-1-1, Higashi, Tsukuba, Ibaraki, Japan) under the Budapest Treaty. Plasmids having the heavy chain and light chain variable regions of F2-103, F5-77 and F5-157, were deposited on Apr. 19, 2001, and hybridoma clones F1-102 and F4-465 were deposited on Apr. 24, 2001, with ATCC (American Type Culture Collection, 10801 University Blvd., Manassas, Va., U.S.A.) under the Budapest Treaty (Table 2).

TABLE 2

| Name | Accession No. |
| --- | --- |
| KM302-1 | FERM BP-7578 |
| KM281-1-10 | FERM BP-7579 |
| KM281-2-10-1-2 | FERM BP-7580 |
| KM341-1-19 | FERM BP-7759 |
| 4D11 | FERM BP-7758 |
| 2105 | FERM BP-8024 |
| F1-102 | ATCC PTA-3337 |
| F4-465 | ATCC PTA-3338 |
| F2-103 heavy chain (F2-103-H) | ATCC PTA-3302 |
| F2-103 light chain (F2-103-L) | ATCC PTA-3303 |

TABLE 2-continued

| Name | Accession No. |
|---|---|
| F5-77 heavy chain (F5-77-H) | ATCC PTA-3304 |
| F5-77 light chain (F5-77-L) | ATCC PTA-3305 |
| F5-157 heavy chain (F5-157-H) | ATCC PTA-3306 |
| F5-157 light chain (F5-157-L) | ATCC PTA-3307 |

EXAMPLE 4

Screening for Hybridoma

Detection of monoclonal antibody having human immunoglobulin γ chain

The human CD40 mouse FC (1 µg/ml) prepared in Example 1 was added at 50 µl/well to each well of a 96-well microplate for ELISA (Maxisorp, Nunc) and incubated at 4° C. for the human CD40 mouse FC to be adsorbed to the microplate. Next, the supernatant was discarded, and then a blocking reagent (Block Ace, DAINIPPON PHARMACEUTICAL) was added to each well, followed by incubation at room temperature for blocking. The culture supernatant (50 µl) of each hybridoma was added to each well for reaction, and then each well was washed with a 0.1% Tween20-containing phosphate buffer (PBS-T). Goat anti-human IgG (γ) antibody (Sigma, A0170) labeled with peroxydase was then diluted 5,000-fold with 1% FBS-containing PBS-T. The solution was added (50 µl/well) to each well, and then incubation was performed. The microplate was washed 3 times with PBS-T, and then a chromogenic substrate solution (TMB, 50 µl/well, SUMITOMO BAKELITE) was added to each well, followed by incubation at room temperature for 30 minutes. A stop solution was added (50 µl/well) to each well to stop reaction. Absorbance at a wavelength of 450 nm was measured with a microplate reader. The culture supernatant of positive wells was analyzed by FACS, an then the wells wherein Ramos cells were stained were selected. The cells in the wells were cloned by the limiting dilution method, and then the cells of 1 clone were obtained per well. hκ-positive status was confirmed by ELISA using the human CD40 mouse FC. As a result, anti-human CD40 antibodies of 173 clones were obtained from 20 mice. Some of these antibodies were shown in Table 3 (agonistic antibodies) and Table 4 (antagonistic antibodies). Among the agonistic antibodies, at least KM341-1-19 and 2105 did not significantly compete with ligands in a competitive test using CD40L-expressing cells, CD40-expressing cells and the antibodies.

TABLE 3

Agonistic antibody

| Hybridoma | Antigen | Subclass | DC | Tumor cell |
|---|---|---|---|---|
| KM302-1 | CD40 mouse FC | IgG4 | activated | suppressed proliferation |
| KM341-1-19 | human CD40-expressing EL-4 | IgG2 | activated | suppressed proliferation |
| KM643-4-11 | CD40 mouse FC | IgG1 | not implemented | not implemented |

TABLE 3-continued

Agonistic antibody

| Hybridoma | Antigen | Subclass | DC | Tumor cell |
|---|---|---|---|---|
| 2053 | CD40 mouse FC | IgG2 | not implemented | not implemented |
| 2105 | CD40 mouse FC | IgG2 | not implemented | not implemented |
| 3821 | human CD40-expressing EL-4 | IgG3 | not implemented | not implemented |
| 3822 | human CD40-expressing EL-4 | IgG3 | not implemented | not implemented |
| 285 | CD40 mouse FC | IgG1 | not implemented | not implemented |
| 110 | CD40 mouse FC | IgG4 | not implemented | not implemented |
| 115 | CD40 mouse FC | IgG4 | not implemented | not implemented |
| F2-103 | CD40 mouse FC | IgG1 | not implemented | not implemented |
| F5-77 | CD40 mouse FC | IgG1 | not implemented | not implemented |

TABLE 4

Antagonistic antibody

| Hybridoma | Antigen | Subclass | Effect of cross-linking | DC-MLR |
|---|---|---|---|---|
| KM281-1-10 | CD40 mouse FC | IgG1 | low | suppressed |
| KM281-2-10-1-2 | CD40 mouse FC | IgG1 | low | not implemented |
| KM283-5 | CD40 mouse FC | IgG4 | significant | not suppressed |
| KM225-2-56 | CD40 mouse FC | IgG4 | significant | not implemented |
| KM292-1-24 | CD40 mouse FC | IgG2 | significant | not implemented |
| KM341-6-9 | human CD4-expressing EL-4 | IgG1 | significant | not implemented |
| 4D11 | CD40 mouse FC | IgG1 | low | not implemented |
| 5H10 | CD40 mouse FC | IgG1 | low | not implemented |
| 11E1 | CD40 mouse FC | IgG1 | low | not implemented |
| 5G3 | CD40 mouse FC | IgG2 | significant | not implemented |
| 3811 | human CD40-expressing EL-4 | IgG1 | significant | not implemented |
| 3411 | human CD40-expressing EL-4 | IgG2 | significant | not implemented |
| 3417 | human CD40-expressing EL-4 | IgG2 | significant | not implemented |
| F4-465 | human CD40-expressing EL-4 | IgG1 | not implemented | not implemented |

Monoclonal antibodies having human immunoglobulin light chain κ (Igκ) were detected in a manner similar to the above described ELISA method for human immunoglobulin γ chain except that goat anti-human Igκ antibodies (diluted 1,000-fold, 50 µl/well, Southern Biotechnology) labeled with peroxydase were used.

The subclass of each monoclonal antibody was identified in a manner similar to the above ELISA method for human immunoglobulin γ chain, except that a sheep anti-human IgG1 antibody, sheep anti-human IgG2 antibody, sheep anti-human IgG3 antibody or sheep anti-human IgG4 antibody (each diluted 2,000-fold, 50 μl/well, The Binding Site) labeled with peroxydase, was used.

Reaction Test of Each Monoclonal Antibody Against Human CD40-Expressing Cells

The reactivity of each monoclonal antibody against a Ramos cell line reported to express CD40 was studied by FACS analysis.

The Ramos cell line was suspended at a concentration of $2 \times 10^6$/ml in a staining buffer (SB) of 0.1% $NaN_3$ and 2% FCS-containing PBS. The cell suspension (100 μl/well) was apportioned to a 96-well round bottom plate (Beckton Dickinson). The culture supernatant (50 μl) of each hybridoma was added, and then incubation was performed at ice temperature for 30 minutes. Human IgG1 antibodies against human serum albumin were used as a negative control, and prepared at a concentration of 2 μg/ml with a hybridoma culture medium. 50 μl of the solution was added, and then incubation was performed at ice temperature for 15 minutes. After washing with SB, 50 μl of R-PE fluorescence-labeled anti-human antibody (Southern Biotechnology) diluted 250-fold was added, and then incubation was performed at ice temperature for 15 minutes. After washing twice with SB, the product was suspended in 300 to 500 μl of a FACS buffer, and then the fluorescence intensity of each cell was measured by FACS (FACSort and FACScan, Beckton Dickinson). As a result, antibodies having binding activity for the Ramos cell line were selected.

EXAMPLE 5

Preparation of Each Antibody

The culture supernatant containing monoclonal antibodies was prepared by the following method.

A G28-5 antibody-producing hybridoma was obtained from ATCC (ATCC No. HB-9110). Anti-CD40 antibody-producing hybridomas were acclimatized in eRDF media (Kyokutoseiyaku) containing bovine insulin (5 μg/ml, Gibco BRL), human transferrin (5 μg/ml, Gibco BRL), ethanolamine (0.01 mM, Sigma) and sodium selenite ($2.5 \times 10^{-5}$ nM, Sigma). The hybridomas were cultured in a spinner flask. When the viable cell rate of the hybridomas reached 90%, the culture supernatant was collected. The collected supernatant was applied to a 10 μm and 0.2 μm filters (German Science) so as to eliminate miscellaneous debris such as hybridomas.

Anti-CD40 antibodies were purified from the above culture supernatant by the following method. The culture supernatant containing the anti-CD40 antibodies was subjected to affinity purification using a Hyper D Protein A column (NGK INSULATORS, LTD) or a Protein G column (for purifying mouse IgG1, Amersham Pharmacia Biotech) according to the attached instruction using PBS (−) as an adsorption buffer and 0.1 M sodium citrate buffer (pH 3) as an elution buffer. 1 M Tris-HCl (pH 8.0) or $Na_2HPO_4$ solution was added to adjust the elution fraction to have a pH of around 7.2. The prepared antibody solution was substituted with PBS (−) using a dialysis membrane (10000 cut, Spectrum Laboratories) or SP column (Amersham Pharmacia Biotech), and then sterilization by filtration was performed using a membrane filter MILLEX-GV (MILLIPORE) with a pore size of 0.22 μm. The concentration of the purified antibody was found by measuring absorbance at 280 nm and then calculating with 1 mg/ml at 1.45 OD.

EXAMPLE 6

Promotion of CD95 Expression in Ramos Cells by Anti-CD40 Agonistic Antibody

A $5.0 \times 10^5$ cells/ml Ramos cell suspension was inoculated at 100 μl/well ($5 \times 10^4$ cells per well) to a 96-well plate. The hybridoma culture supernatant or the purified antibody was diluted to 20 μg/ml with a medium, and then the solution was added at a concentration of 100 μl/well to a 96-well plate. After overnight culture, the cells were collected and then analyzed by FACSCan or FACSsort (Beckton Dickinson) using R-PE-labeled anti-CD95 antibodies (Pharmingen N.J.). FIG. 1 shows the result. The horizontal axes in FIG. 1 indicate the expression intensity of CD95. Addition of antibodies is indicated with a thick line, and non addition of antibodies is indicated with a thin line. It was shown that the KM302-1 antibodies promoted CD95 expression better than G28-5 antibodies, which were the known antibodies. That is, the KM302-1 antibody was shown to be more effectively agonistic.

EXAMPLE 7

Suppression of CD95 Expression in Ramos Cell by Anti-CD40 Antagonistic Antibody

Figure 2A:
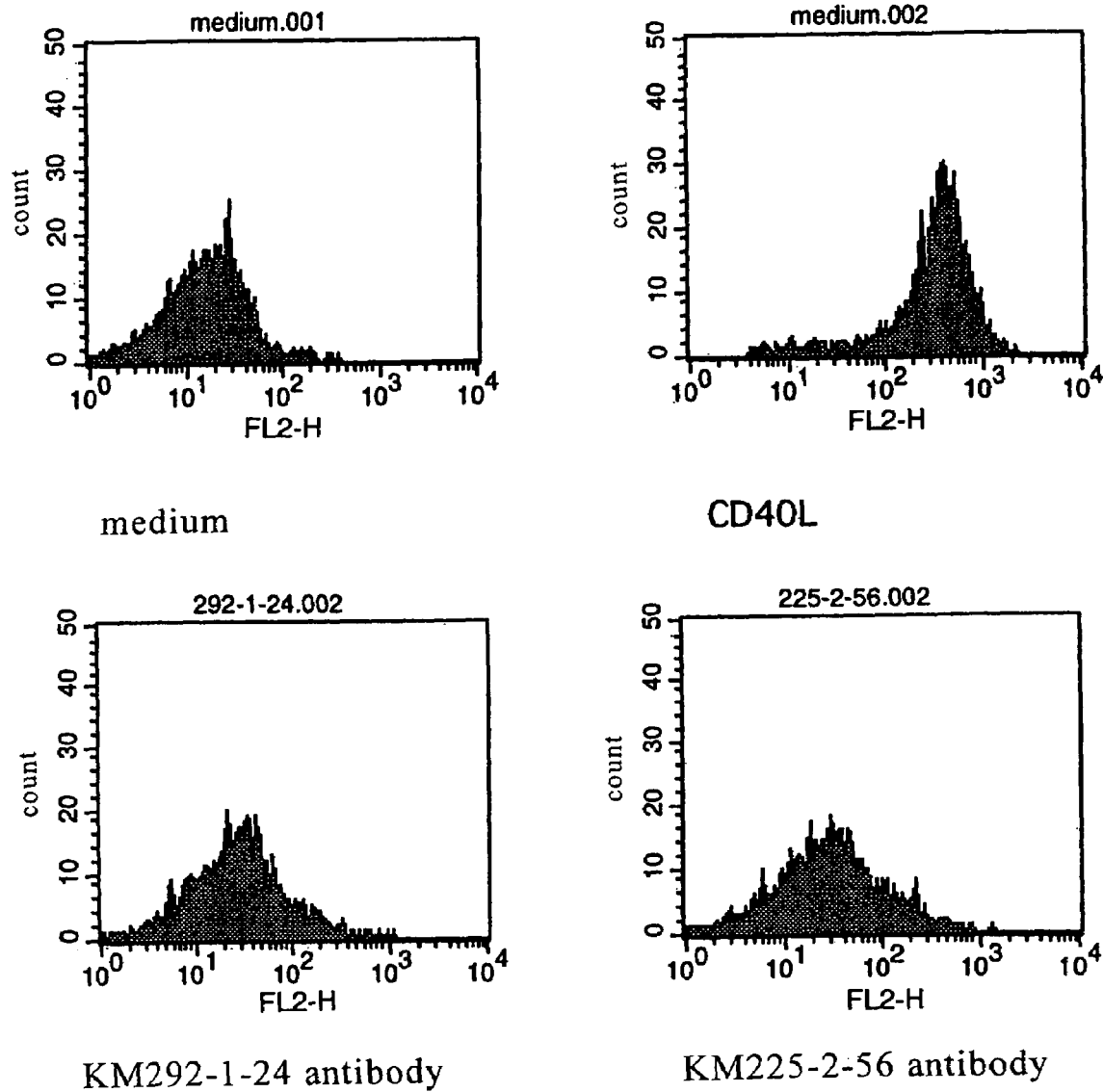
FIG. 2A shows that the antagonistic antibodies neutralized the action of CD40 ligands on Ramos cells.
Figure 2B:
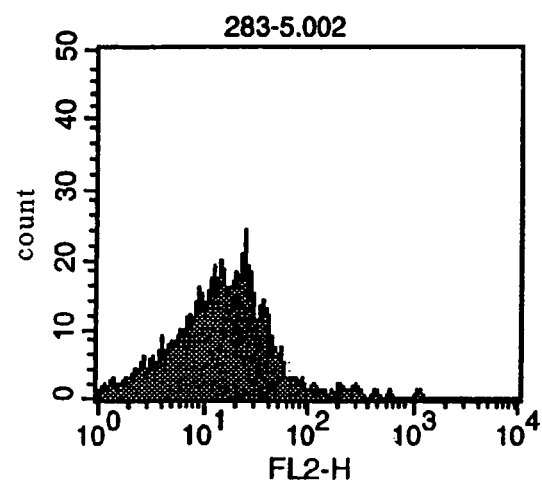
FIG. 2B shows that the antagonistic antibodies neutralized the action of CD40 ligands on Ramos cells.
Figure 2B:
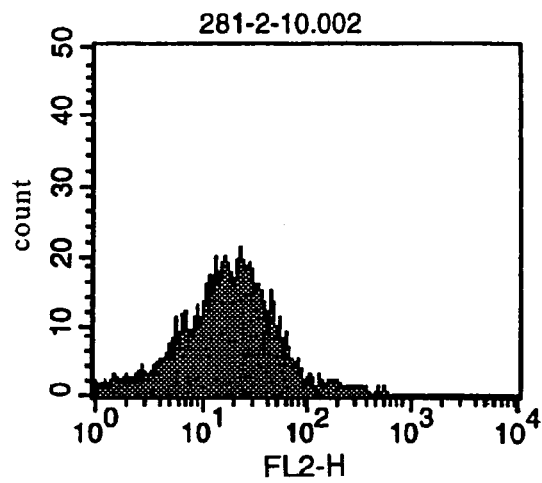
Figure 2B:
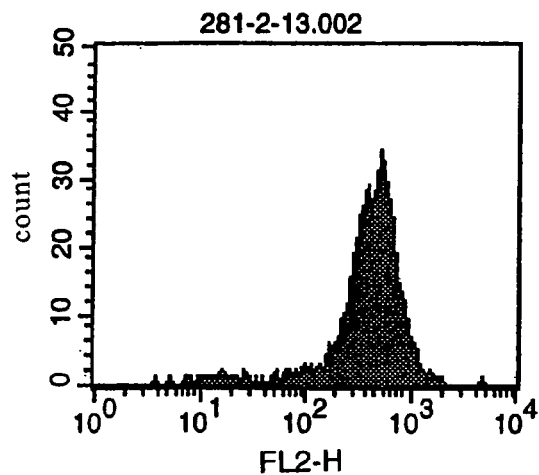
Figure 3:
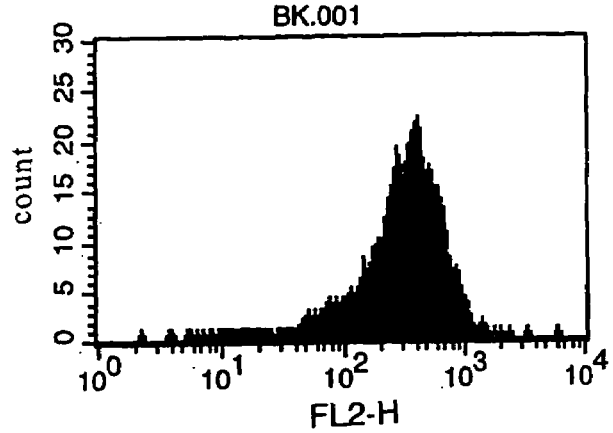
FIG. 3 shows that KM281-1-10 antibodies neutralized the action of CD40 ligands on Ramos cells.
Figure 3:
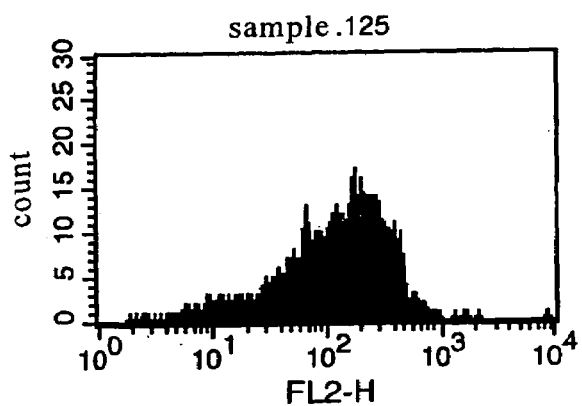
Figure 3:
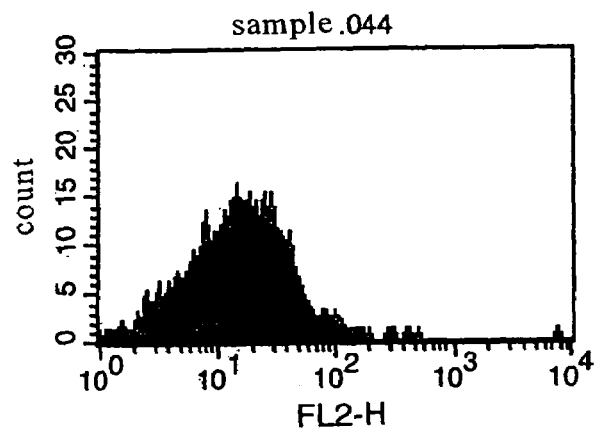

A $1.0 \times 10^6$ cells/ml Ramos cell suspension was inoculated at 50 μl/well to a 96-well plate. The hybridoma culture supernatant or the purified antibody was adjusted at 2 μg/ml with a medium, and then added at 100 μl/well to a 96-well plate. Soluble CD40 ligands (4 μg/ml, ALEXIS CORPORATION) and anti-FLAG antibodies (4 μg/ml, M2, Sigma) were added to media, and then the media were added at 50 μl/well to the 96-well plate. After overnight culture, the cells were collected and then analyzed by FACS using R-PE-labeled anti-CD95 antibodies (Pharmingen N.J.). FIGS. 2A and 2B, and 3 show the results. The horizontal axes in the figures indicate the expression intensity of CD95. CD95 expression was suppressed to the same degree as that of a negative control by the antibodies produced by each of the following hybridomas: KM281-1-10, KM281-2-10-1-2, KM283-5, KM292-1-24 and KM225-2-56.

In FIG. 3, KM281-1-10 antibodies (lower panel) suppressed CD95 expression more effectively than that the 5D12 antibodies (central panel), the known antibody, only slightly suppressed CD95 expression. Specifically, the KM281-1-10 antibody was shown to be more effectively antagonistic. Thus, the human monoclonal antibody was shown to be an antagonistic antibody.

Effect of Cross-Linking by Anti-Immunoglobulin Antibody

Figure 4:
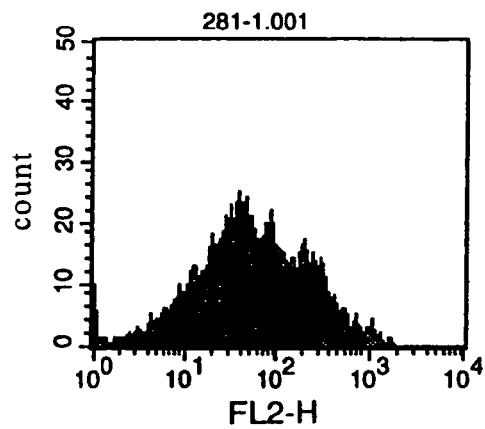
FIG. 4 shows that cross-linked KM281-1-10 antibodies did not promote CD95 expression.
Figure 4:
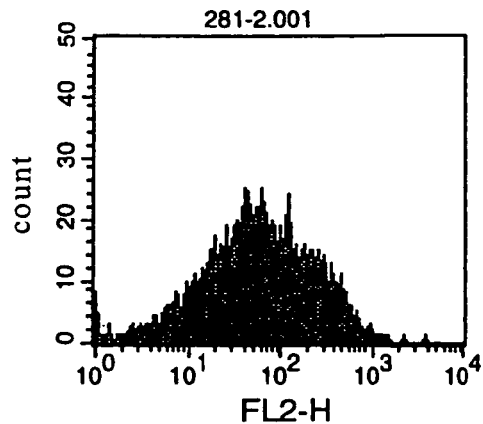
Figure 4:
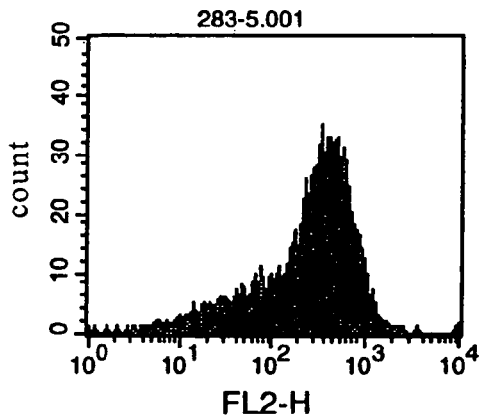
Figure 4:
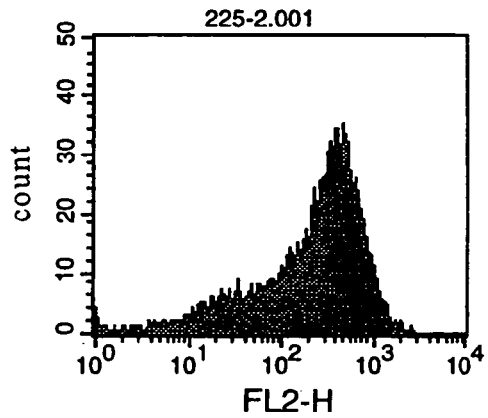
Figure 4:
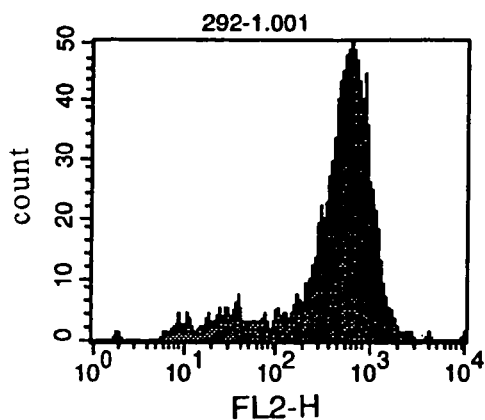
Figure 5:
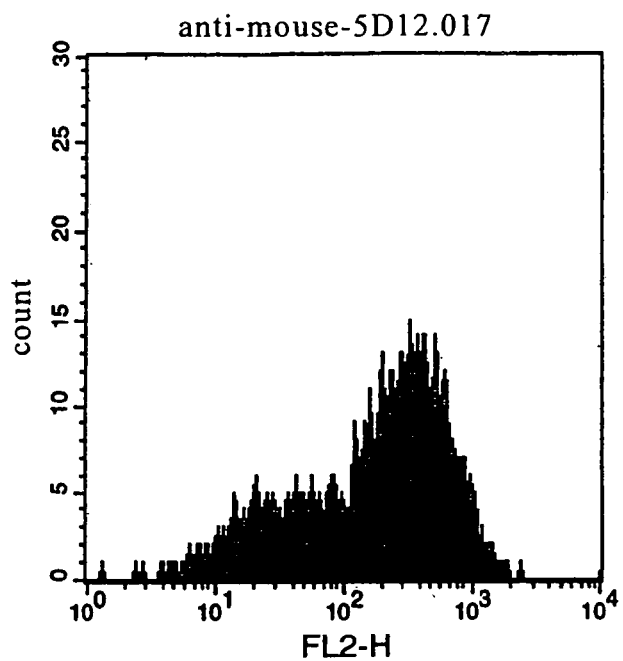
FIG. 5 shows that cross-linked 5D12 antibodies promoted CD95 expression.
Figure 5:
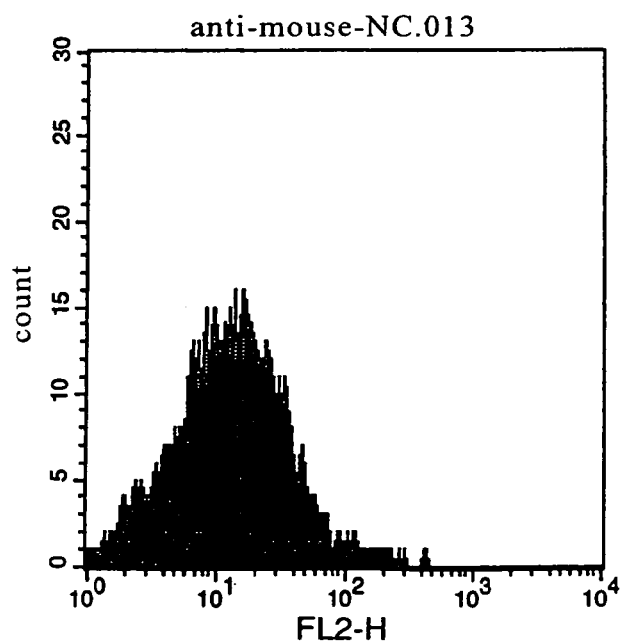

A $1.0 \times 10^6$ cells/ml Ramos cell suspension was inoculated at 50 μl/well to a 96-well plate. The hybridoma culture supernatant or the purified antibody was adjusted to 2 μg/ml with a medium, and then added at 100 μl/well to a 96-well plate. Anti-human IgG antibodies (Sigma, I3382) or anti-mouse IgG antibodies (Biosource, AMI3401) were added at 4 μg/ml to media, and then the media were added at 50 μl/well to a 96-well plate. After overnight culture, the cells were collected, and then analyzed by FACS using R-PE-labeled anti-CD95 antibodies (Pharmingen N.J.). FIGS. 4 and 5 show the results. The horizontal axes in the figures indicate the expression intensity of CD95. CD95 expression was suppressed by the antibodies produced by each of the hybridomas KM281-1-10 and KM281-2-10-1-2. Conversely, CD95 expression was enhanced by the antibodies produced by each of the following hybridomas, 5D12, KM283-5, KM292-1-24 and KM225-2-56.

EXAMPLE 8

Proliferation Suppression in Ramos Cells by Anti-CD40 Agonistic Antibody

Figure 6:
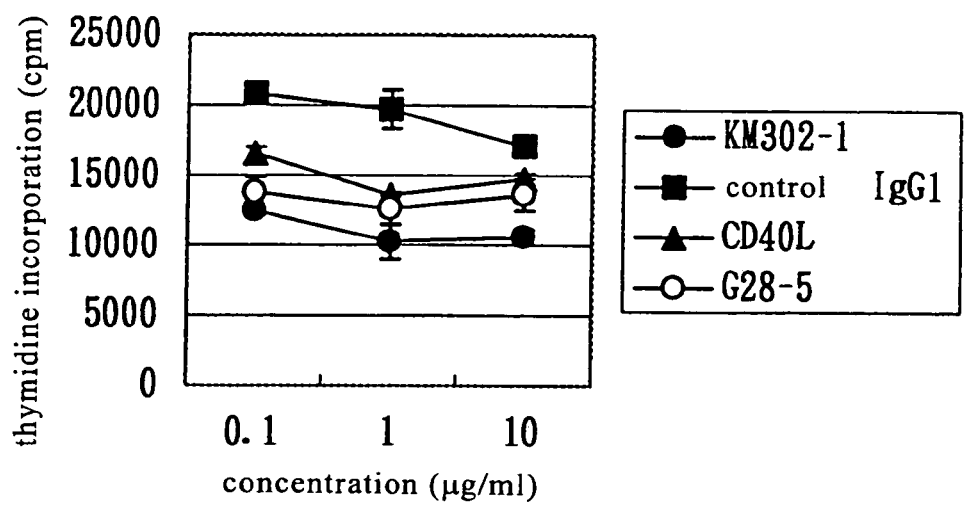
FIG. 6 shows the proliferation suppressive effect of KM302-1 antibodies on tumor cells.
Figure 6:
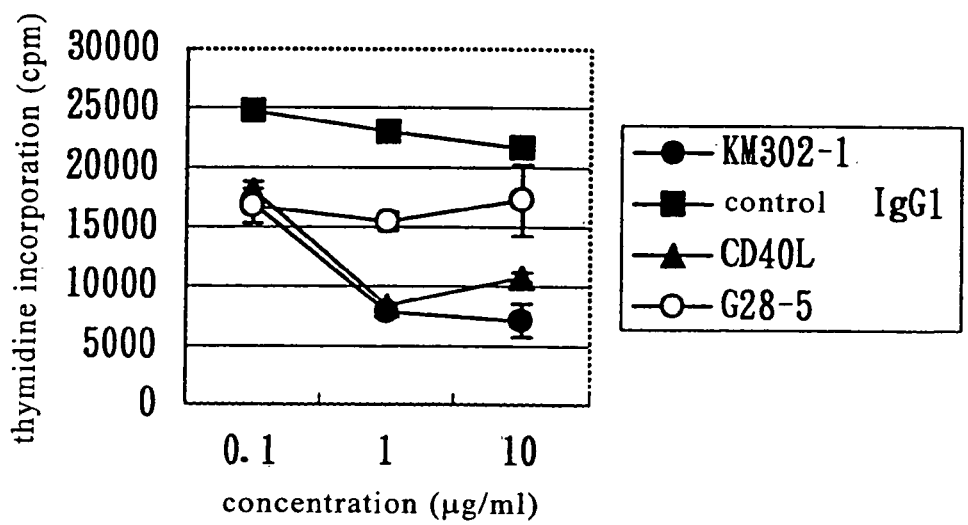

A $1.0 \times 10^5$ cells/ml Ramos and HS-Sulton cell suspension was inoculated at 100 μl/well to a 96-well plate. A mixture of equivalent amount of the purified antibodies or soluble CD40 ligands, and anti-FLAG antibodies (M2) was added to media. After 2 days of culturing, 10 μl of 100 μCi/ml $^3$H-Thymidine (Amersham Pharmacia) was added. After 18 hours, the culture product was harvested in a Printed Filtermat A (Wallac) using a Macro 96 Harvester (SKATRON), dried, and then immersed well in Betap;Scint (Wallac). After packaging, activity was measured using a 1205 BETA-PLATE liquid scintillation counter. FIG. 6 shows the results. In the figure, the longitudinal axes indicate the amount of $^3$H thymidine incorporated by cells, and the horizontal axes indicate the concentration of the antibody or CD40L in the culture solution. When the KM302-1 antibodies were added to Ramos cells and HS-Sulton cells, the amount of thymidine incorporated was lower than the conventional G28-5 antibodies and CD40L. Thus, it was shown that the KM302-1 antibody is an agonistic antibody that can effectively suppress the proliferation of tumor cells.

EXAMPLE 9

Activation of Dendritic Cell by CD40 Agonistic Antibody (1) Materials and Methods Recombinant human IL-4 was purchased from Genzyme techne. Anti-human CD14 MACS beads were purchased from Miltenyi Biotech GmbH. Lymphoprep was purchased from Nycomed Pharma AS. The medium used for culturing was RPMI1640 (Gibco BRL) supplemented with 10% heat inactivated FCS (Cell Culture Technologies), 10 mM HEPES (Sigma), 55 μM 2-mercaptoethanol (Gibco BRL) and streptomycin sulfate (MEIJI SEIKA KAISHA, LTD.), when DC were induced. The cells in a staining process were washed with PBS (Sigma) supplemented with 2% FCS (Cell Culture Technologies) and 0.02% Azaid. When the cells were frozen, Cell banker (Nippon Zenyaku Kogyo) was used.

(2) Induction of Monocyte-Derived DC

Mononuclear cells were prepared (PBMC) from peripheral blood by density gradient centrifugation using Lymphoprep. The cells were subjected to positive selection using anti-human CD14 MACS beads, so as to separate the cells into a CD14 positive fraction and negative fraction. Recombinant human GM-CSF (50 ng/ml) and recombinant human IL-4 (100 ng/ml) were added to the positive fraction, followed by culturing in RPMI1640 media supplemented with 10% FCS in a 6-well plate. At the start of culturing, the cells were cultured at a concentration of $1 \times 10^6$/ml (3 ml per well). During culturing, the media were exchanged once every 2 days. Medium exchange was performed by sampling 10% of the culture solution in a centrifugation tube, centrifuging the solution, removing the supernatant, suspending with a new culture solution (containing cytokine and the like at the above concentration) in a volume 2-fold greater than the sampled culture solution, and then returning the suspension to each well. On day 6 of culturing, the cells were collected, the cell number was calculated, and then the cells were suspended at a concentration of $1 \times 10^6$/ml in the above media. Anti-CD40 antibodies or the isotype controls thereof were added to the media, and then cultured for further 4 days in a 24-well plate. During this period, no culture exchange was performed (cell number per well of $1 \times 10^6$ cells, and cell concentration of $1 \times 10^6$/ml).

(3) Cell Staining and Analysis by Flow Cytometer

For staining, anti-HLA-DR antibodies (isotype control: rat IgG2a), anti-CD86 antibodies (isotype control: rat IgG1) and anti-CD83 antibodies (isotype control: rat IgG2b) were used. First, the antibodies were added, and then incubation was performed at 4° C. for 30 minutes. After 3 washings, analysis was performed using the FACS Calibur (Beckton Dickinson).

(4) Increase in IL-12 Secretion Ability of Mature DC

After immature DC were obtained as described above, LPS (400 pg/ml) and IFNγ ($10^{-3}$M) were added, and then culturing was performed for 2 days, thereby obtaining mature DC. To the mature DC, 10 μg/ml anti-CD40 antibodies or the isotype control was added. For the supernatant after 24 hours, IL-12 production was measured using ELISA (Pharmingen).

(5) Results and Discussion

Figure 7:
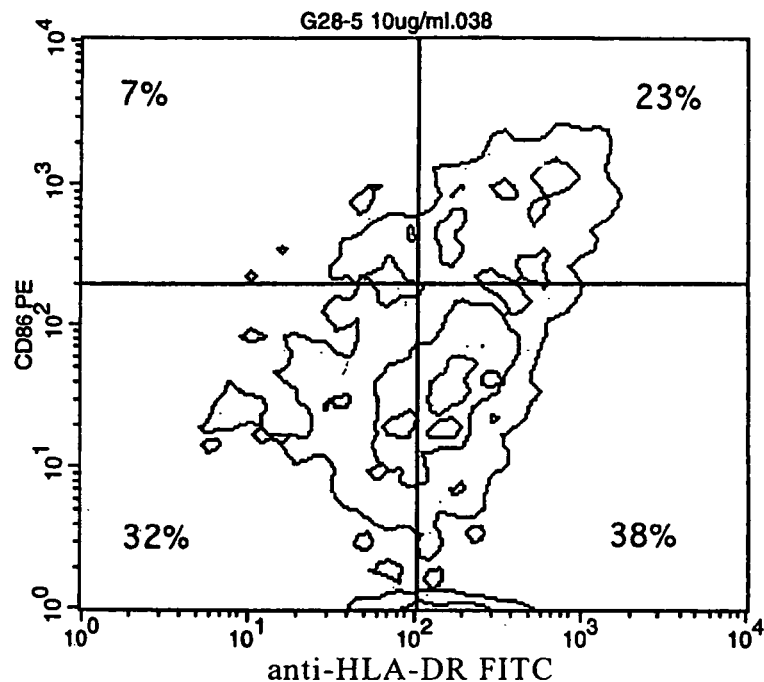
FIG. 7 shows that KM302-1 antibodies promoted the maturation of DC.
Figure 7:
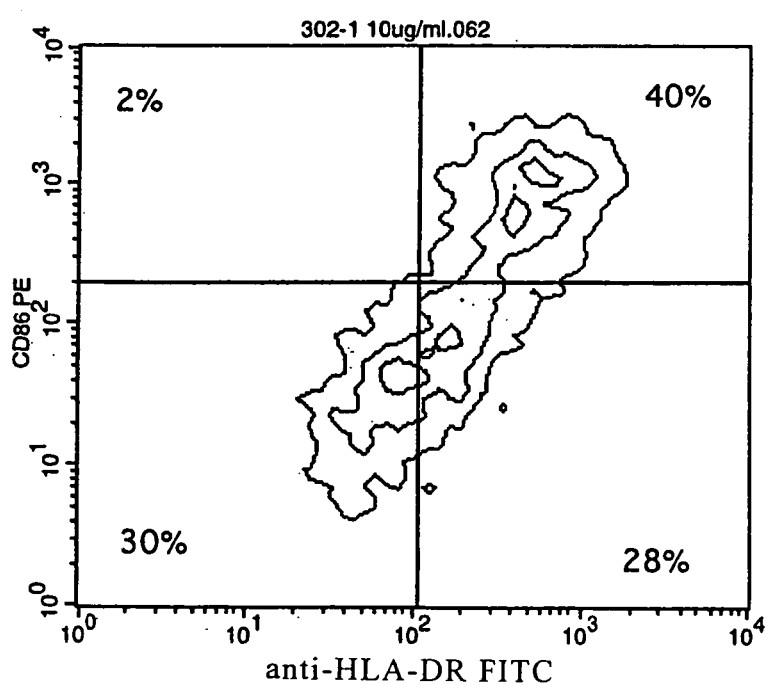
Figure 8:
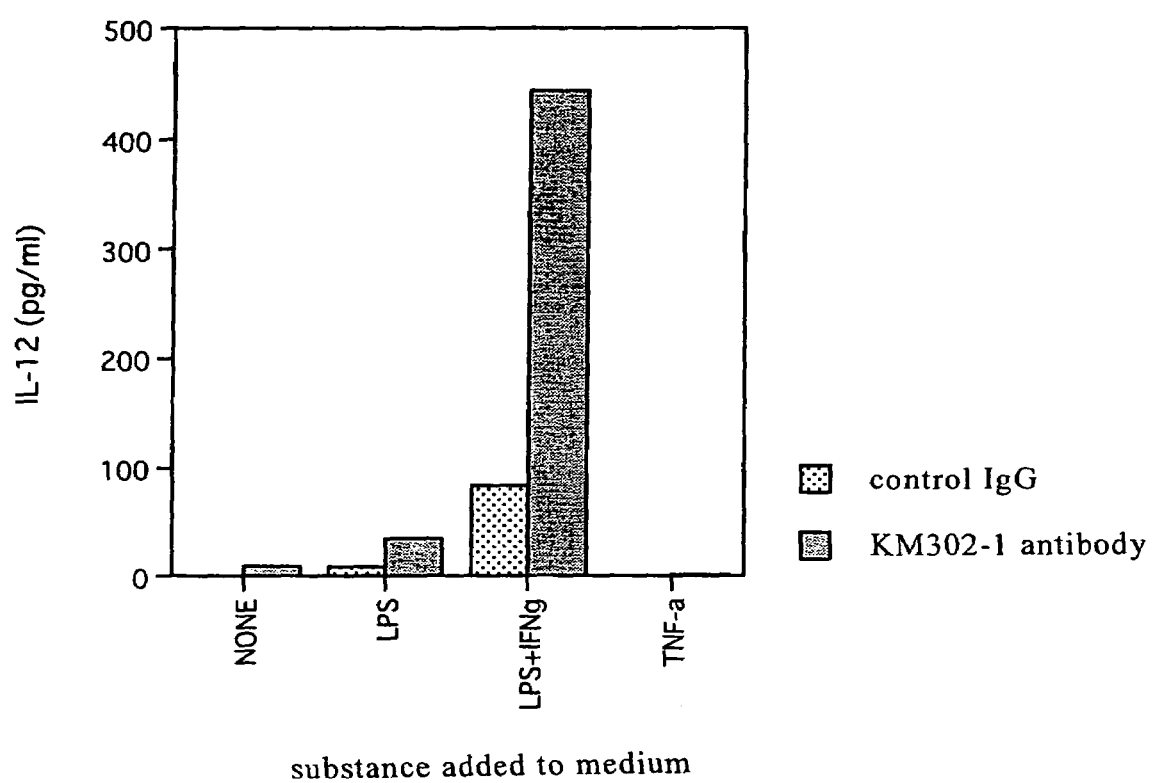
FIG. 8 shows that KM302-1 antibodies promoted the IL-12 production of DC.

FIG. 7 shows the effect of KM302-1 antibodies, the agonistic antibodies, on DC maturation, and FIG. 8 shows the effect of KM302-1 antibodies on IL-12 production of mature DC. The degree of maturation was compared with G28-5 antibodies as a control. When the expression of CD86 and that of HLA-DR were examined, the expression was further elevated, that is, the degree of maturation was increased in the case of KM302-1 antibodies compared with the case of G28-5 antibodies. It was also shown that IL-12 secretion was increased by the treatment of mature DC with KM302-1 antibodies. Accordingly, it was shown that the KM302-1 antibodies acted as agonistic antibodies on DC.

EXAMPLE 10

DC-MLR

Blood (peripheral blood) collected from a normal human was centrifuged at 2000 rpm for 10 minutes, and then the serum was absorbed. The blood cell fraction was re-suspended with PBS, and then gently placed on Ficoll (Amersham Pharmacia). Centrifugation was performed at 2000 rpm for 30 minutes, so that a PBMC portion in the intermediate layer was collected, washed twice with PBS, and then used for a certain cell separation process using MACS.

Monocyte separation for culturing DC was performed according to the attached instruction using MACS (Miltenyi Biotec GmbH). This is briefly explained as follows. 800 μl of MACS Buffer and 200 μl of MACS CD14 (Miltenyi Biotec GmbH, 502-01) were added to PBMC ($1 \times 10^8$), and then treated at 4° C. for 15 minutes. The cells were adsorbed to a MACS LS column, and then washed. The cells adsorbed to the column were collected as monocytes. MACS HLA-DR (Miltenyi Biotec GmbH, 461-01) was added to the cells that were not adsorbed to the column. HLR-DR positive cells were removed with a BS column, thereby preparing a T cell fraction. The proportion of CD3 positive cells was measured by FACS, and then substantial number of T cells was calculated from the total cell number in the T cell fraction. The obtained monocytes were cultured in R0 media (PPMI medium supplemented with β-mercapto ethanol (Gibco) and HEPES (SIGMA)) containing 100 ng/ml IL-4 (R&D system), 50 ng/ml G-CSF (KIRIN) and 10% FCS (SIGMA) at a concentration of $1 \times 10^6$ cells/ml in a 6-well culture plate. On day 5 after culturing, 10 ng/ml LPS (DIFCO) was added for the cells to differentiate into mature DC.

Figure 9:
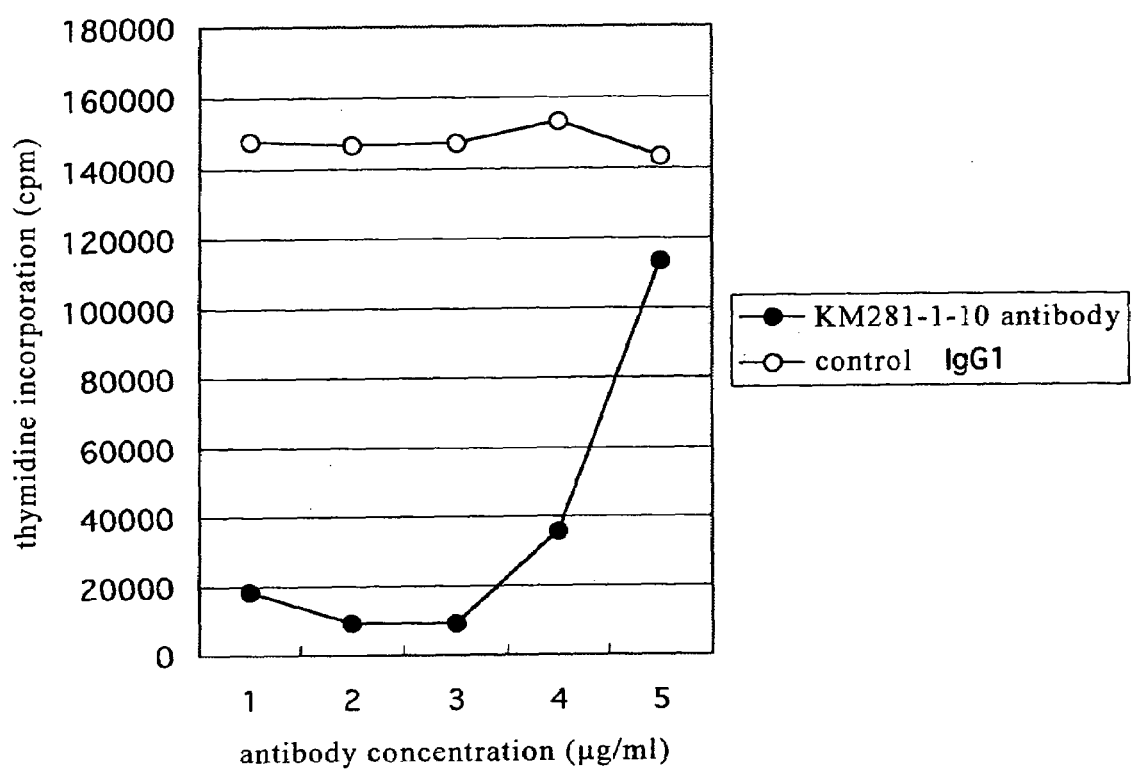
FIG. 9 shows that KM281-1-10 antibodies neutralized the action of CD40 ligands on DC.
Figure 10:
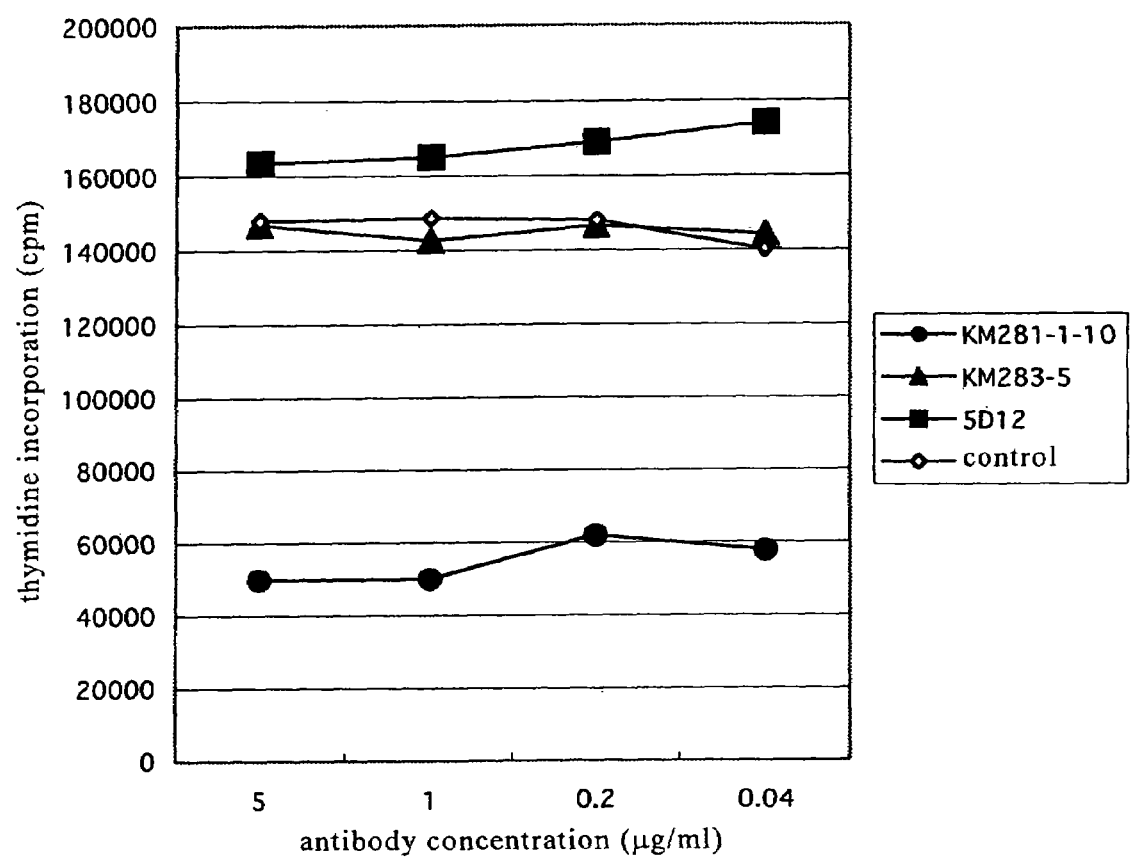
FIG. 10 shows that KM281-1-10 antibodies neutralized the action of CD40 ligands on DC.
Figure 11:
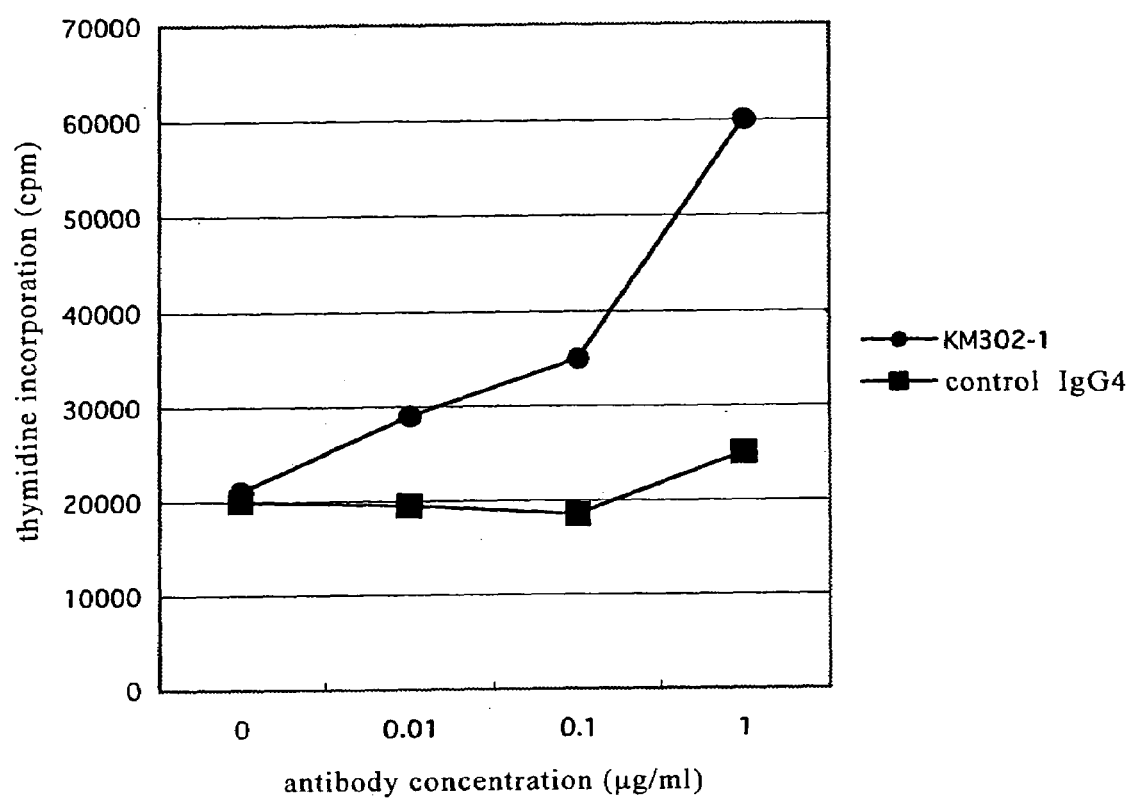
FIG. 11 shows that KM302-1 antibodies activated immature DC-MLR.

MLR was performed by mixing T cells and mature DC, which had been isolated from different humans. The cell ratio of T cells to DC was determined as 1:80, and number of T cells was determined as $2\times10^5$ cells/well. First, antibodies were added to DC for reaction to proceed for 30 minutes. Subsequently, T cells were added, culturing was performed for 4 days, and then 10 µl of 100 µCi/ml $^3$H-Thymidine (Amersham Pharmacia) was added. 14 hours later, the cells were harvested in Printed Filtermat A (Wallac) using a Macro 96 Harvester (SKATRON), dried, and then immersed well in Betap;Scint (Wallac). After packaging, activity was measured using a 1205 BETAPLATE liquid scintillation counter. MLR using immature DC was performed by mixing T cells with mature DC, which had been isolated from different humans. With a cell ratio of T cells to DC of 1:40, MLR was performed similarly. FIGS. 9 and 10 show the results. It was shown that the addition of KM281-1-10 antibodies lowered thymidine incorporation, and thus MLR could be suppressed. Furthermore, it was shown in FIG. 10 that KM283-5 and 5D12 antibodies could not suppress DC-MLR. That is, only the KM281-1-10 antibody is an antagonistic antibody that neutralizes the action of CD40 ligands on DC. Moreover, FIG. 11 shows the results of examining the effect of KM302-1 antibodies, which are agonistic antibodies, on MLR using immature DC. Activation of DC promoted interaction with T cells, and caused an increase in thymidine incorporation. These results indicated that KM302-1 is an agonistic antibody that acts on immature DC.

EXAMPLE 11

Effect of CD40 Antibody on the Binding of CD40L to CD40

Anti-CD40 antibodies were caused to bind to immobilized CD40 human FC using BIAcore 2000 (Biacore), and then changes in the binding amount of soluble CD40L to CD40 were measured. According to the instruction attached to the system, soluble CD40 human FC was immobilized on a CM chip (CM5, Biacore). Next, 25 µg/ml anti-CD40 antibodies were added to bind to CD40. Further, 10 µg/ml soluble CD40L was added for binding. A difference between the binding amounts before and after addition of CD40L was measured. When control IgG was added, the binding amount of CD40L was 100 RU. After addition of KM302-1 antibodies, the binding amount of CD40L was 110 RU, and after addition of KM283-5 antibodies the binding amount of CD40L was 18RU. Thus, it was shown that the KM302-1 antibody does not inhibit the binding of CD40L to CD40.

EXAMPLE 12

Promotion of CD95 Expression in Ramos Cells by Anti-CD40 Agonistic Antibody

Figure 12:
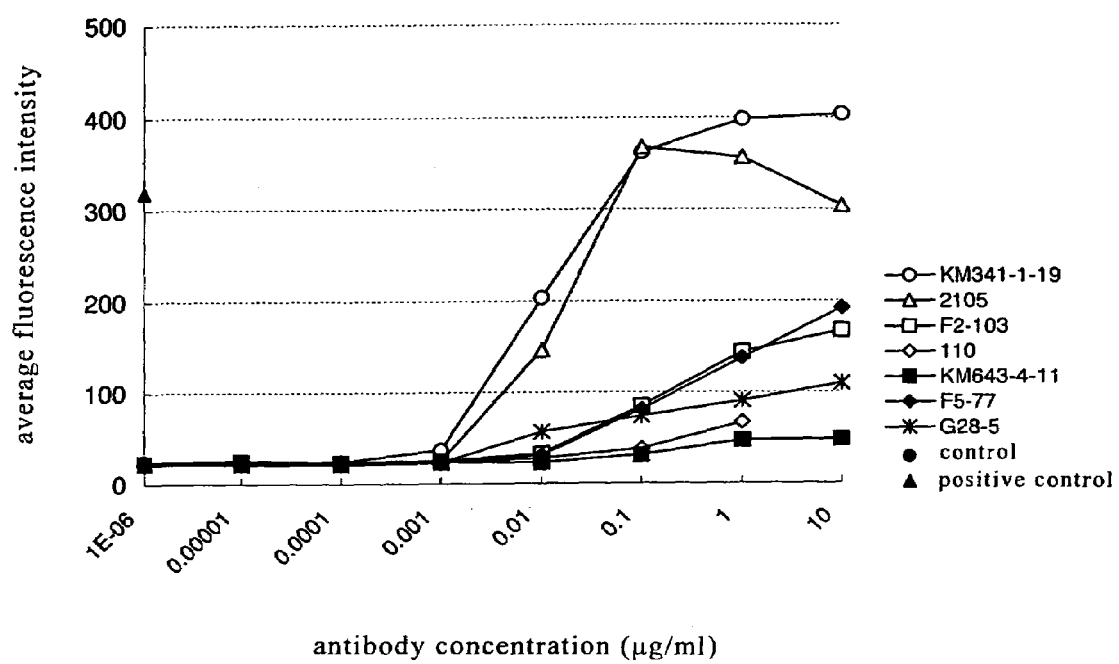
FIG. 12 shows that KM341-1-19 antibodies and the like promoted CD95 expression of Ramos cells.

Purified antibodies of the hybridomas obtained in Example 4 were analyzed according to the method of Example 6, and then clones producing agonistic antibodies were selected (number of cells per well: $5\times10^4$; cell concentration: $2.5\times10^5$/ml). FIG. 12 shows the results. In the figure, the horizontal axis indicates the antibody concentration in culture solutions, and the longitudinal axis indicates average fluorescence intensities, that is, CD95 expression intensities. At a concentration of 0.01 µg/ml or more, KM341-1-19 and 2105 antibodies were shown to promote CD95 expression of Ramos cells more effectively than G28-5 antibodies, which are known mouse antibodies. Specifically, KM341-1-19 and 2105 antibodies were shown to be more effective agonistic antibodies. Further, the agonistic activity (to increase CD95 expression of Ramos cells) of KM341-1-19 and 2105 antibodies (0.01 µg/ml) was higher than that of G28-5 antibodies (10 µg/ml) (FIG. 12). Table 5 summarizes that at each antibody concentration, CD95 expression level is how many times greater or less than that expressed by the addition of G28-5 antibodies.

TABLE 5

| Antibody concentration (µg/ml) | KM341-1-19 | 2105 | F5-77 | F2-103 |
|---|---|---|---|---|
| 0.01 | 5.7 | 3.9 | | |
| 0.1 | 7.0 | 7.1 | 1.2 | 1.2 |
| 1 | 5.7 | 5.1 | 1.7 | 1.8 |
| 10 | 4.5 | 3.3 | 2.0 | 1.7 |

EXAMPLE 13

Activation of Dendritic Cell by CD40 Agonistic Antibody

Figure 13:
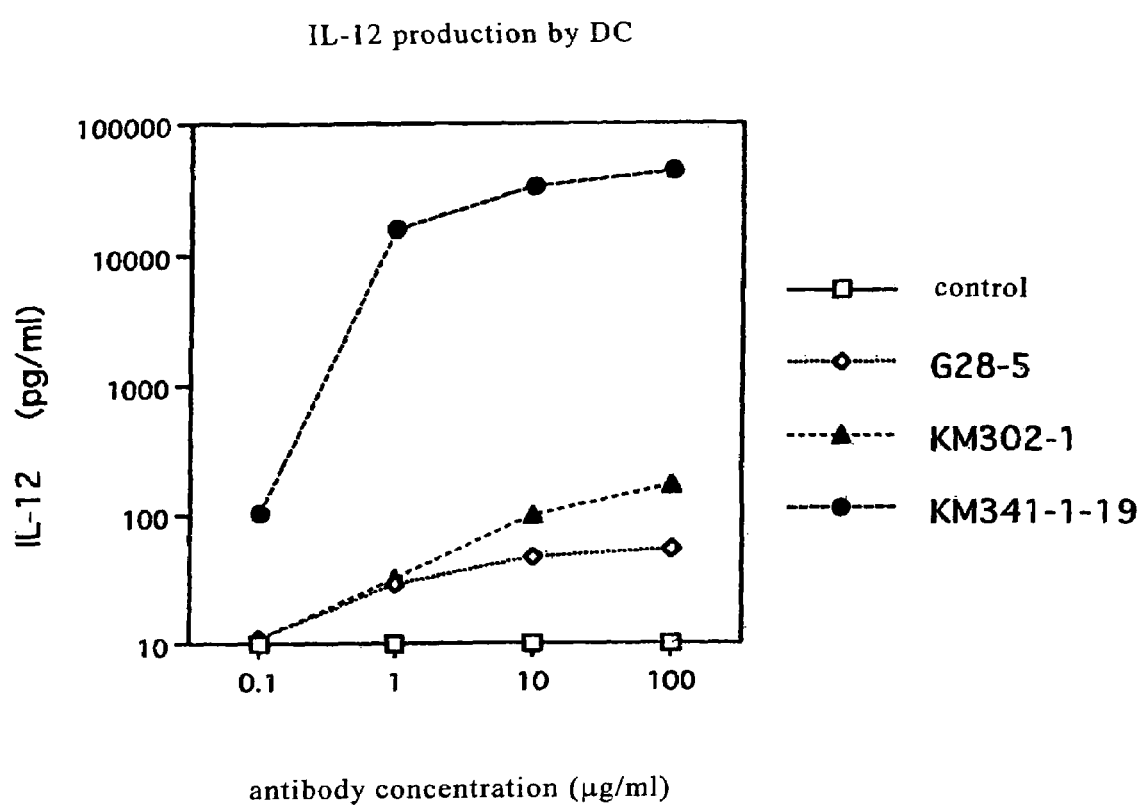
FIG. 13 shows that KM341-1-19 antibodies promoted IL-12 production of mature DC.
Figure 14:
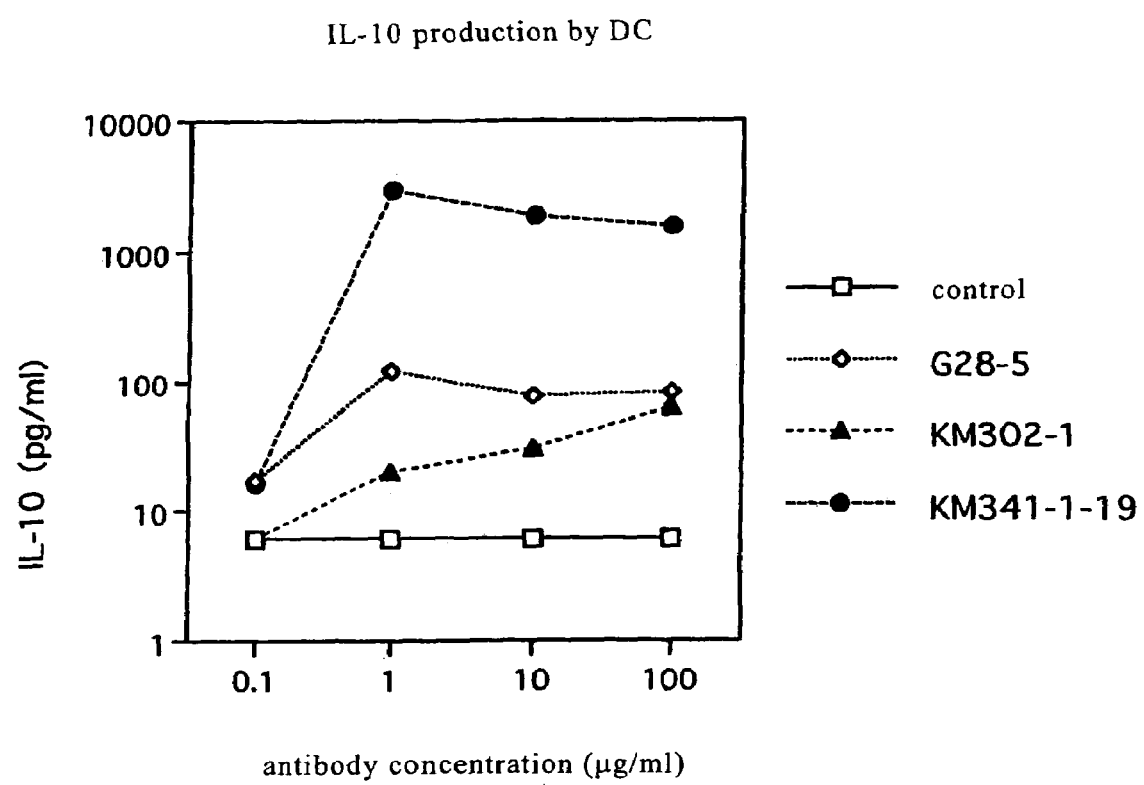
FIG. 14 shows that KM341-1-19 antibodies promoted IL-10 production of mature DC.

According to the method of Example 9, the effect of CD40 agonistic antibodies on IL-12 production and IL-10 production by mature DC was examined. IL-10 was measured by the ELISA (Pharmingen) method. FIGS. 13 and 14 show the results. It was shown that IL-12 secretion was increased by treatment with KM341-1-19 antibodies. In contrast, even when CD40 ligand-expressing recombinant L cells ($2\times10^5$ cells/ml) that had been irradiated with X-rays (5000 rad) were allowed to co-exist, the concentrations of IL-12 and IL-10 in culture solutions were 254 and 51 pg/ml, respectively. They were lower than that when 1 µg/ml KM341-1-19 antibodies were added.

As described above, it was shown that KM341-1-19 antibodies act on DC as effective agonistic antibodies. The agonistic activity of KM341-1-19 antibodies (0.1 µg/ml) to cause mature DC to secrete IL-12 was higher than that of G28-5 antibodies (100 µg/ml). The agonistic activity of KM341-1-19 antibodies (1 µg/ml) to cause mature DC to secrete IL-12 was 100 times or more greater than that by G28-5 antibodies (100 µg/ml) (FIG. 13). Furthermore, the agonistic activity of KM341-1-19 antibodies (1 µg/ml) to cause mature DC to secrete IL-10 was 10 times or more greater than that by G28-5 antibodies (100 µg/ml) (FIG. 14). Moreover, since the subclass of KM341-1-19 antibody was IgG2, the antibody has lower binding ability to the Fc receptor than that of IgG1 or IgG3. Its ability to sensitize the killer activity of NK cells and ability to activate the complement system are also weak. Accordingly, there may be a low risk that the function of CD40-expressing cells or the number of the cells themselves decreases due to the antibody. Furthermore, the antibody is not easily cross-linked by an Fc receptor, so that it can be expected that the drug effect is easily controlled without any large fluctuation in in vivo agonistic activity due to cross-linking.

EXAMPLE 14

Figure 15:
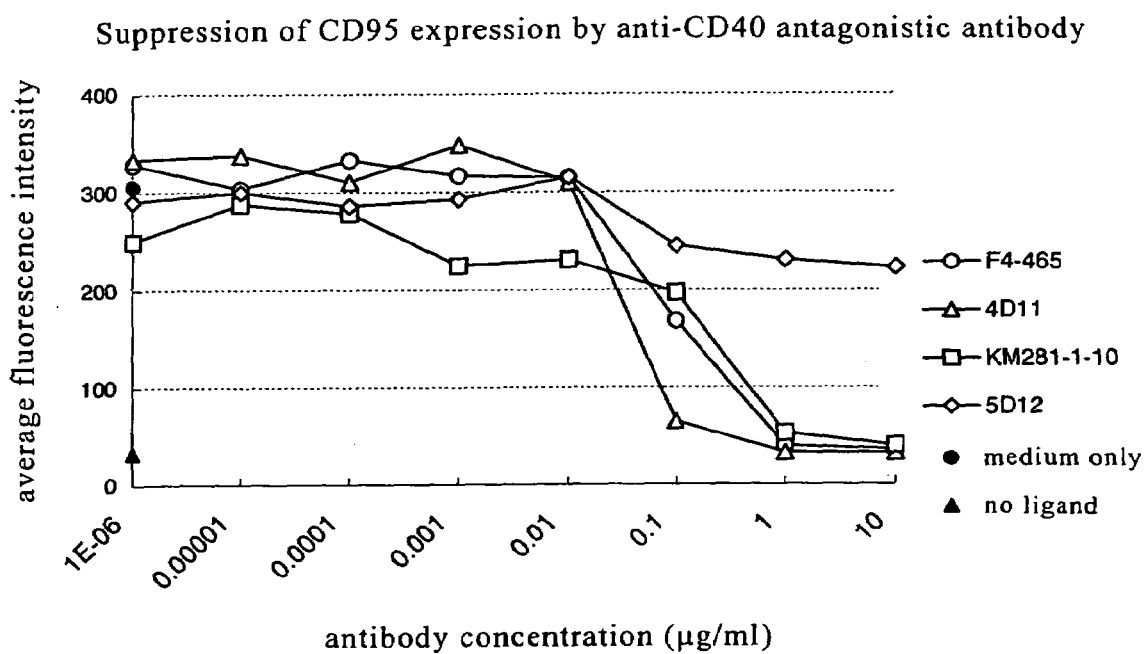
FIG. 15 shows that 4D11 antibodies and the like neutralized the action of CD 40 ligands on Ramos cells.

Suppression of CD95 Expression in Ramos Cells by Anti-CD40 Antagonistic Antibody $1.0\times10^6$ cells/ml Ramos cell suspension was inoculated at 50 µl/well to a flat bottom 96-well plate (number of cells per well: $5\times10^4$). Purified antibodies diluted with media were added at 100 µl/well to a 96-well plate. Human CD40 ligand-expressing recombinant mouse L cells (see Spriggs, M. K. et. al., J. Exp. Med., 176: 1543, 1992; Garrone, P. et. al., J. Exp. Med., 182: 1265, 1995 and the like) were prepared at $1.0\times10^5$ cells/ml. The prepared cells were added at 50 µl/well (the number of Ramos cells per well: $5\times10^4$; Ramos cell concentration: $2.5\times10^4$ cells/ml; the number of mouse L cells per well: 5×10³; mouse cell concentration: 2.5×10⁴ cells/ml). After overnight culture, the cells were collected, and then analyzed by FACS using R-PE-labeled anti-CD95 antibodies. FIG. 15 shows the results. In the figure, the longitudinal axis indicates the average fluorescence intensity, that is, CD95 expression intensity. Whereas the known 5D12 antibodies suppressed the expression slightly, 4D11 antibodies suppressed, even at a concentration of 0.1 μg/ml, CD95 expression to the same degree as that of a case of a negative control wherein no CD40L-expressing cells had been added. Moreover, at a concentration of 1 μg/ml, 4D11, F4-465 and KM281-1-10 suppressed CD95 expression to the same degree as that of the case of the negative control wherein no CD40L-expressing cells had been added. These results showed that 4D11, F4-465 and KM281-1-10 antibodies are more effective antagonistic antibodies. Table 6 shows relative values of the average fluorescence intensity corresponding to each antibody concentration, when the value of the control case wherein no antagonistic antibodies were added is determined as 100.

TABLE 6

| Antibody concentration (μg/ml) | 5D12 | 4D11 | F4-465 | KM281-1-10 |
|---|---|---|---|---|
| 0.1 | 77.6 | 11.8 | 49.6 | 60.1 |
| 1 | 72.3 | 0.01 | 2.5 | 7.3 |
| 10 | 69.5 | 0 | 1.1 | 2.6 |

EXAMPLE 15

Figure 16:
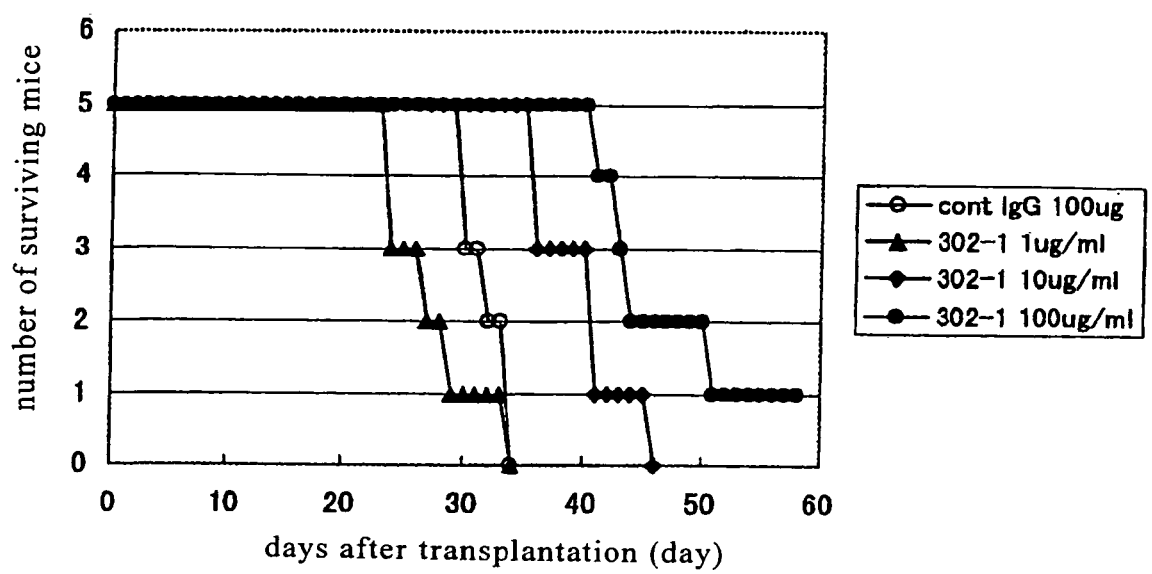
FIG. 16 shows that KM302-1 antibodies showed antitumor effect on the human tumor cell-transplanted mouse model.

Anti-Tumor Effect in Ramos Cell Transplantation Model by Anti-CD40 Agonistic Antibody Anti-asialo GM1 antibodies were intravenously injected to 5-week-old C.B.17/Icr-scidJc1 mice (CLEA JAPAN). 1 day later, 5×10⁶ Ramos cells per mouse were intravenously injected as tumor cells. 1 day later, KM302-1 antibodies or anti-human albumin human IgG antibodies as a negative control were intravenously injected. The doses per mouse of KM302-1 antibodies were 1, 10 and 100 μg, and the same of the negative control antibodies was 100 μg. Each of these antibodies was administered once to 5 mice. FIG. 16 shows the results. By day 34 after transplantation, all the mice of the negative control-administered group had died, whereas all the 5 mice each of the groups administered with 10 μg and 100 μg of KM302-1 antibodies had been administered to which survived. Thus, the anti-tumor effect of KM302-1 antibodies was confirmed. The KM302-1 antibody is of the IgG4 subclass, so that the Fc receptor-mediated antibody dependent cellular cytotoxicity (ADCC) and activation of the complement system are weak. Despite these characteristics, it was observed that single administration of 10 μg of KM302-1 antibodies prolonged the survival time of tumor-bearing mice.

EXAMPLE 16

Ramos Cell Proliferation Suppression by Anti-CD40 Agonistic Antibody

Figure 17A:
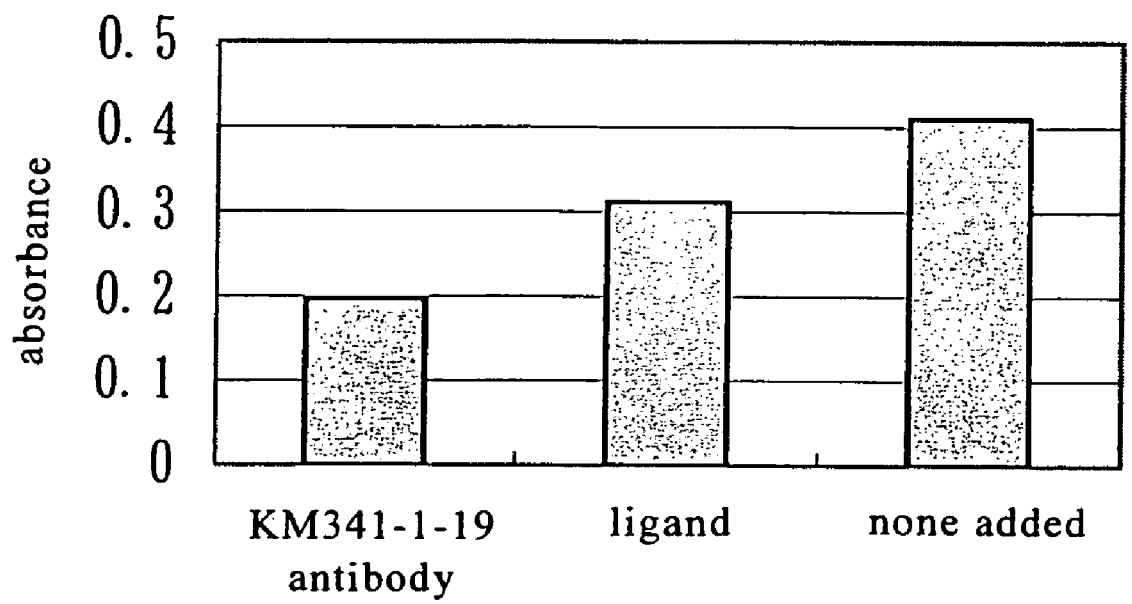
FIG. 17 shows that KM341-1-19 antibodies showed a proliferation suppressive effect against tumor cells.
Figure 17B:
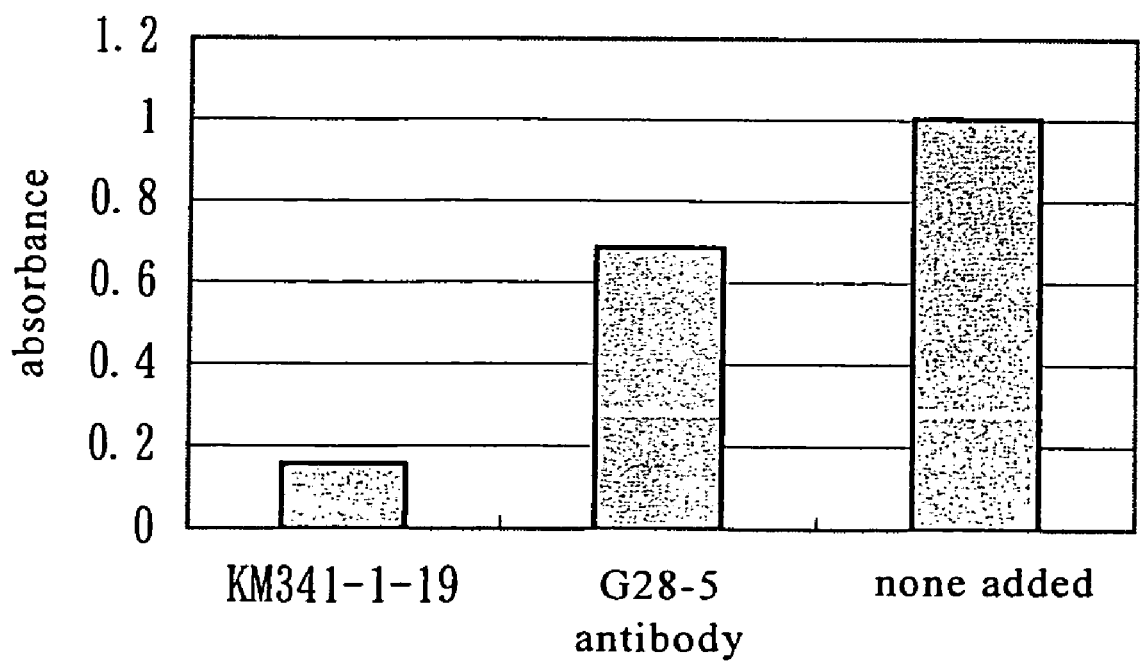

A Ramos cell suspension was prepared at 1×10⁴ cells/ml in an RPMI1640 medium supplemented with 10% FBS, and then 100 μl of the suspension was apportioned to a 96-well plate. A KM341-1-19 antibody or soluble ligand solution prepared at 20 μg/ml using media was added. Anti-FLAG antibodies (M2) with the same concentration as that of the ligands were allowed to co-exist with the soluble ligands (the concentration in the reaction solution was 10 μg/ml), thereby enhancing the activity. After 5 days of culturing, 20 μl of MTS reagent (Promega) was added to each well, and then allowed to react for 2 to 3 hours. Differences in absorbance between the cell-free and antibody-free wells and the cell- and antibody-containing wells were measured at a wavelength of 490 nm, thereby measuring viable cell count. Furthermore, the proliferation-suppressing action was compared with that of G28-5 antibodies using a 96-well U-bottomed plate similarly. KM341-1-19 antibodies or G28-5 antibodies prepared at 2 μg/ml using media were added. FIG. 17 shows the results. In wells to which KM341-1-19 antibodies had been added, dead cells were observed, the cell number was significantly lower than those of wells to which G28-5 antibodies or the ligands had been added, and the absorbance was also low. These results indicate that the proliferation of tumor cells was suppressed, and cell death was induced.

EXAMPLE 17 cDNA Cloning of Antibody Gene

Hybridomas producing KM341-1-19, 2105, 110, 115, KM281-1-10, 4D11, KM643-4-11, F4-465, F2-103 and F5-77 antibodies were cultured, and then the cells were collected by centrifugation. TRIZOL (Gibco BRL) was added to the cells, and then Total RNA was extracted according to the attached instructions. Cloning of the variable regions of the antibody cDNA was performed according to the attached instructions using a SMART RACE cDNA amplification Kit (CLONTECH). Using 5 μg of total RNA as a template, 1st Strand cDNA was constructed. To amplify the heavy chains (H chain) of KM341-1-19, 2105, 110, 115, KM281-1-10, 4D11, KM643-4-11, F2-103 and F5-77, Z-Taq (Takara) and UMP and hh6 primers were used, and a cycle of 98° C. for 1 second and 68° C. for 30 seconds was repeated 30 times. Furthermore, using 1 μl of the reaction solution as a template and NUMP and hh3 primers, a cycle of 98° C. for 1 second and 68° C. for 30 seconds was repeated 20 times. To amplify a F4-465 heavy chain, UMP and hh2 primers and an Advantage 2 PCR kit (Clonthech, cat#1910) were used, and 5 cycles of 94° C. for 5 seconds and 72° C. for 3 minutes, 5 cycles of 94° C. for 5 seconds, 70° C. for 0 seconds and 72° C. for 3 minutes, and 25 cycles of 94° C. for 5 seconds, 68° C. for 10 seconds and 72° C. for 3 minutes were performed.

hh6 primer: 5'-GGT CCG GGA GAT CAT GAG GGT GTC CTT-3' (SEQ ID NO: 3)

hh3 primer: 5'-GTG CAC GCC GCT GGT CAG GGC GCC TG-3' (SEQ ID NO: 4)

hh2 primer: 5'-GCT GGA GGG CAC GGT CAC CAC GCT G-3' (SEQ ID NO: 5)

Subsequently, the amplified PCR product was purified using a PCR purification kit (QIAGEN), and then the nucleotide sequence was determined using hh4 as a primer. Alternatively, the product was subcloned to PCR-Script (Stratagene, Lajolla, Calif.) or PCR-Blunt (Invitrogen, Carlsbad, Calif.), and then sequencing was performed. Based on the sequence information, antibody heavy-chain-specific primers were synthesized. A 341H primer was synthesized in the case of KM341-1-19, a 2105Hsal primer in the case of 2105, a 110Hsal primer in the case of 110 and 115, a 281Hsal primer in the case of KM281-1-10, a 4D11Sal primer in the case of 4D11, a 643Hsal primer in the case of KM643-4-11, H11-9 5' primer in the case of F4-465, a F2-103H primer in the case of F2-103 and F5-77H primer in the case of F5-77. Using the antibody heavy chain specific primers and hh4, cDNA was amplified from the 1st Strand cDNA, and then the sequence from the opposite direction was determined using the amplified product as a template and the antibody-specific primers.

The light chains (L chains) of KM341-1-19, 2105, 110, 115, KM281-1-10, 4D11, KM643-4-11, F2-103 and F5-77 were amplified using UMP and hk2 primers and by repeating 30 times a cycle of 98° C. for 1 second and 68° C. for 30 seconds. The light chain of F4-465 was amplified using UMP and hL2 primers and by repeating 30 times a cycle of 98° C. for 1 second and 68° C. for 30 seconds. The amplified PCR product was purified using a PCR purification kit, and then the nucleotide sequence was determined using hk6 or hL2 primers. Based on the sequences, light chain specific primers were synthesized. A 341K primer was synthesized in the case of KM341-1-19, 2053 KBgl primer in the case of 2105, 110 KBgl primer in the case of 110 and 115, 281 KBgl primer in the case of KM281-1-10, 4D11KBgl in the case of 4D11, 643 KBgl primer in the case of KM643-4-11, Lamda 5' primer in the case of F4-465, and F2-103K primer in the case of F-103 and F5-77.

```
hh4 primer: 5'-GGTGCCAGGGGGAAGACCGATGG-3'              (SEQ ID NO: 6)

341H primer: 5'-atatgtcgacGCTGAATTCTGGCTGACCAGGGCAG-3' (SEQ ID NO: 7)

2105Hsal: atatgtcgacTCCCAGGTGTTTCCATTCAGTGATCAG        (SEQ ID NO: 8)

110Hsal: atatgtcgacTTCCATTCGGTGATCAGCACTGAACAC         (SEQ ID NO: 9)

281Hsal: atatgtcgacTTTGAGAGTCCTGGACCTCCTGTG            (SEQ ID NO: 10)

4D11Sal: atatgtcgacGAGTCATGGATCTCATGTGCAAG             (SEQ ID NO: 11)

643Hsal: atatgtcgacCCAGGGCAGTCACCAGAGCTCCAGAC          (SEQ ID NO: 12)

H11-9 5': -ACC GTG TCG ACT ACG CGG GAG TGA CT          (SEQ ID NO: 13)

F2-103 H: accgtgtcgacgctgatcaggactgcaca               (SEQ ID NO: 14)

F5-77 H: accgtgtcgacggtgatcaggactgaacag               (SEQ ID NO: 15)
```

In the case of 341-1-19, 110, 115, KM643-4-11, KM281-1-10, 4D11 and 2105, cDNA was amplified from the 1st Strand cDNA using the light chain specific primer and hk6 primer. The sequence was then determined from both directions using the amplified product as a template. For F4-465, F2-103 and F5-77, subcloning to PCR-Script (Stratagene, Lajolla, Calif.) or PCR-Blunt (Invitrogen, Carlsbad, Calif.) was performed to determine the sequence.

```
hk2 primer: 5'-GTT GAA GCT CTT TGT GAC GGG CGA GC-3'    (SEQ ID NO: 16)

hL2 primer: 5'-TCT TCT CCA CGG TGC TCC CTT CAT-3'       (SEQ ID NO: 17)

341K primer: 5'-atatagatctGAACTGCTCAGTTAGGACCCAGAGG-3' (SEQ ID NO: 18)

2053KBgl: atatagatctCGCGGGGAAGGAGACTGCTCAGTT            (SEQ ID NO: 19)

110KBgl: atatagatctAGTCAGACCCAGTCAGGACACAGC             (SEQ ID NO: 20)

281KBgl: atatagatctGAGCTGCTCAGTTAGGACCCAGAGGG           (SEQ ID NO: 21)

4D11KBgl: atatagatctTAAGCAAGTGTAACAACTCAGAGTAC          (SEQ ID NO: 22)

643KBgl: atatagatctGAGGAACTGCTCAGTTAGGACCCAGAGG         (SEQ ID NO: 23)

Lamda 5': -AACTCCAGATCTGCCTCAGGAAGCAGCATC              (SEQ ID NO: 24)

F2-103 K: aactccagatctagggcaagcagtggtaac               (SEQ ID NO: 25)

hk6 primer: 5'-TGGCGGGAAGATGAAGACAGATGGTG-3'            (SEQ ID NO: 26)
```

DNAs of 341-1-19 encoding the full-length H-chain and L-chain variable regions and the amino acid sequences of H-chain and L-chain are respectively shown below.

The translation initiation point of the H-chain DNA is an ATG codon that begins from the 50th adenine (A) from the 5' end of SEQ ID NO: 27, and the termination codon is TGA beginning from the 1472nd thymine (T). The boundary of the antibody variable region and the constant region is located between the 493rd adenine (A) and the 494th guanine (G) from the 5'end. In the amino acid sequence, the H-chain variable region ranges from the N-terminus to the 148th serine (S) residue of SEQ ID NO: 28, and the constant region is of the 149th alanine (A) and the following residues. It was predicted by a gene sequence prediction software (Signal P ver.2) that the H-chain signal sequence ranges from the N-terminus to the 20th serine (S) of SEQ ID NO: 28. It is thought that the N-terminus of the mature protein is the 21st glutamine (Q) of SEQ ID NO: 28.

The translation initiation point of the L-chain DNA is an ATG codon that begins from the 29th A from the 5' end of SEQ ID NO: 29, and the variable region ranges from the 5' end to the 400th adenine (A). In the amino acid sequence, the variable region ranges from the N-terminus to the 124th lysine (K) of SEQ ID NO: 30. Analysis of the N-terminus of the purified L-chain protein revealed that the L-chain signal sequence ranges from the N-terminus to the 20th glycine (G) of SEQ ID NO: 30, and the N-terminus of the mature protein is the 21st glutamic acid (E) of SEQ ID NO: 30.

```
341-1-19 H-chain:

GTCGACGCTGAATTCTGGCTGACCAGGGCAGCCACCAGAGCTCCAGACAA        (SEQ ID NO: 27)

TGTCTGTCTCCTTCCTCATCTTCCTGCCCGTGCTGGGCCTCCCATGGGTGT

CCTGTCACAGGTCCAACTGCAGCAGTCAGGTCCAGGACTGGTGAAGCCCT

CGCAGACCCTCTCACTCACCTGTGCCATCTCCGGGGACAGTGTCTCTAGCA

ACAGTGCTACTTGGAACTGGATCAGGCAGTCCCCATCGAGAGACCTTGAGT

GGCTGGGAAGGACATACTACAGGTCCAAGTGGTATCGTGATTATGTAGGAT

CTGTGAAAAGTCGAATAATCATCAACCCAGACACATCCAACAACCAGTTCT

CCCTGCAGCTGAACTCTGTGACTCCCGAGGACACGGCTATATATTACTGTAC

AAGAGCACAGTGGCTGGGAGGGGATTACCCCTACTACTACAGTATGGACGT

CTGGGGCCAAGGGACCACGGTCACCGTCTCTTCAGCCTCCACCAAGGGCC

CATCGGTCTTCCCCCTGGCGCCCTGCTCCAGGAGCACCTCCGAGAGCACAG

CGGCCCTGGGCTGCCTGGTCAAGGACTACTTCCCCGAACCGGTGACGGTG

TCGTGGAACTCAGGCGCTCTGACCAGCGGCGTGCACACCTTCCCAGCTGT

CCTACAGTCCTCAGGACTCTACTCCCTCAGCAGCGTGGTGACCGTGCCCTC

CAGCAACTTCGGCACCCAGACCTACACCTGCAACGTAGATCACAAGCCCA

GCAACACCAAGGTGGACAAGACAGTTGAGCGCAAATGTTGTGTCGAGTGC

CCACCGTGCCCAGCACCACCTGTGGCAGGACCGTCAGTCTTCCTCTTCCCC

CCAAAACCCAAGGACACCCTCATGATCTCCCGGACCCCTGAGGTCACGTG

CGTGGTGGTGGACGTGAGCCACGAAGACCCCGAGGTCCAGTTCAACTGGT

ACGTGGACGGCGTGGAGGTGCATAATGCCAAGACAAAGCCACGGGAGGA

GCAGTTCAACAGCACGTTCCGTGTGGTCAGCGTCCTCACCGTTGTGCACCA

GGACTGGCTGAACGGCAAGGAGTACAAGTGCAAGGTCTCCAACAAAGGC

CTCCCAGCCCCCATCGAGAAAACCATCTCCAAAACCAAAGGGCAGCCCCG

AGAACCACAGGTGTACACCCTGCCCCCATCCCGGGAGGAGATGACCAAGA

ACCAGGTCAGCCTGACCTGCCTGGTCAAAGGCTTCTACCCCAGCGACATCG

CCGTGGAGTGGGAGAGCAATGGGCAGCCGGAGAACAACTACAAGACCAC

ACCTCCCATGCTGGACTCAGACGGCTCCTTCTTCCTCTACAGCAAGCTCAC

CGTGGACAAGAGCAGGTGGCAGCAGGGGAACGTCTTCTCATGCTCCGTGA

TGCATGAGGCTCTGCACAACCACTACACGCAGAAGAGCCTCTCCCTGTCTC

CGGGTAAATGAGGATCC
```

341-1-19 H-chain amino acid sequence

MSVSFLIFLPVLGLPWGVLSQVQLQQSGPGLVKPSQTLSLTCAISGDSVSSNSA (SEQ ID NO: 28)

TWNWIRQSPSRDLEWLGRTYYRSKWYRDYVGSVKSRIIINPDTSNNQFSLQL

NSVTPEDTAIYYCTRAQWLGGDYPYYYSMDVWGQGTTVTVSSASTKGPSVF

PLAPCSRSTSESTAALGCLVKDYFPEPVTVSWNSGALTSGVHTFPAVLQSSGLY

SLSSVVTVPSSNFGTQTYTCNVDHKPSNTKVDKTVERKCCVECPPCPAPPVAG

PSVFLFPPKPKDTLMISRTPEVTCVVVDVSHEDPEVQFNWYVDGVEVHNAKT

KPREEQFNSTFRVVSVLTVVHQDWLNGKEYKCKVSNKGLPAPIEKTISKTKG

QPREPQVYTLPPSREEMTKNQVSLTCLVKGFYPSDIAVEWESNGQPENNYKTT

PPMLDSDGSFFLYSKLTVDKSRWQQGNVFSCSVMHEALHNHYTQKSLSLSPG

K 341-1-19 L-chain:

ACTGCTCAGTTAGGACCCAGAGGGAACCATGGAAGCCCCAGCTCAGCTTC (SEQ ID NO: 29)

TCTTCCTCCTGCTACTCTGGCTCCCAGATACCACCGGAGAAATTGTGTTGAC

ACAGTCTCCAGCCACCCTGTCTTTGTCTCCAGGGGAAAGAGCCACCCTCTC

CTGCAGGGCCAGTCAGAGTGTTAGCAGCTACTTAGCCTGGTACCAACAGA

AACCTGGCCAGGCTCCCAGGCTCCTCATCTATGATGCATCCAACAGGGCCA

CTGGCATCCCAGCCAGGTTCAGTGGCAGTGGGTCTGGGACAGACTTCACT

CTCACCATCAGCAGCCTAGAGCCTGAAGATTTTGCAGTTTATTACTGTCAGC

AGCGTAGCAACACTTTCGGCCCTGGGACCAAAGTGGATATCAAACGTACG 341-1-19 L-chain amino acid sequence

MEAPAQLLFLLLLWLPDTTGEIVLTQSPATLSLSPGERATLSCRASQSVSSYLA (SEQ ID NO: 30)

WYQQKPGQAPRLLIYDASNRATGIPARFSGSGSGTDFTLTISSLEPEDFAVYYC

QQRSNTFGPGTKVDIKRT

DNAs of 2105 encoding the H-chain variable region and L-chain variable region and the amino acid sequences of the H-chain and L-chain are shown below.

The translation initiation point of the H-chain DNA is an ATG codon that begins from the 70th adenine (A) from the 5' end of SEQ ID NO: 31. The boundary of the antibody variable region and the constant region is located between the 495th adenine (A) and the 496th guanine (G) from the 5' end. In the amino acid sequence, the H-chain variable region ranges from the N-terminus to the 142nd serine (S) residue of SEQ ID NO: 32, and the constant region is of the 149th alanine (A) and the following residues. It was predicted by a gene sequence prediction software (Signal P ver.2) that the H-chain signal sequence ranges from the N-terminus to the 19th cystein (C) of SEQ ID NO: 32. It is thought that the N-terminus of the mature protein is the 20th glutamic acid (E) of SEQ ID NO: 32.

The translation initiation point of the L-chain DNA is an ATG codon that begins from the 28th A from the 5' end of SEQ ID NO: 33, and the variable region ranges from the 5' end to the 405th adenine (A). In the amino acid sequence, the variable region ranges from the N-terminus to the 126th lysine (K) of SEQ ID NO: 34. It was predicted by gene sequence prediction software (Signal P ver.2) that the L-chain signal sequence ranges from the N-terminus to the 20th glycine (G) of SEQ ID NO: 34. It is thought that the N-terminus of the mature protein is the 21st glutamic acid (E) of SEQ ID NO: 34.

2105 H-chain

CTGAACACAGACCCGTCGACTCCCAGGTGTTTCCATTCAGTGATCAGCACT (SEQ ID NO: 31)

GAACACAGAGGACTCACCATGGAGTTGGGACTGAGCTGGATTTTCCTTTTG

GCTATTTTAAAAGGTGTCCAGTGTGAAGTGCAGCTGGTGGAGTCTGGGGG

AGGCTTGGTACAGCCTGGCAGGTCCCTGAGACTCTCCTGTGCAGCCTCTGG

-continued

```
ATTCACCTTTGATGATTATGCCATGCACTGGGTCCGGCAAGCTCCAGGGAA

GGGCCTGGAGTGGGTCTCAGGTATTAGTTGGAATAGTGGTAGCTTGGTGCA

TGCGGACTCTGTGAAGGGCCGATTCACCATCTCCAGAGACAACGCCAAGA

ACTCCCTGTATCTGCAAATGAACAGTCTGAGAGCTGAGGACACGGCCTTGT

ATTACTGTGCAAGAGATAGGCTATTTCGGGGAGTTAGGTACTACGGTATGGA

CGTCTGGGGCCAAGGGACCACGGTCACCGTCTCCTCAGCTAGCACCAAGG
```

2105 H-chain amino acid sequence

MELGLSWIFLLAILKGVQCEVQLVESGGGLVQPGRSLRLSCAASGFTFDDYA    (SEQ ID NO: 32)

MHWVRQAPGKGLEWVSGISWNSGSLVHADSVKGRFTISRDNAKNSLYLQMN

SLRAEDTALYYCARDRLFRGVRYYGMDVWGQGTTVTVSSASTK

2105 L-chain

```
CTGCTCAGTTAGGACCCAGAGGGAACCATGGAAGCCCCAGCTCAGCTTCT    (SEQ ID NO: 33)

CTTCCTCCTGCTACTCTGGCTCCCAGATACCACCGGAGAAATTGTGTTGAC

ACAGTCTCCAGCCACCCTGTCTTTGTCTCCAGGGGAAAGAGCCACCCTCTC

CTGCAGGGCCAGTCAGAGTGTTAGCAGCTACTTAGCCTGGTACCAACAGA

AACCTGGCCAGGCTCCCAGGCTCCTCATCTATGATGCATCCAACAGGGCCA

CTGGCATCCCAGCCAGGTTCAGTGGCAGTGGGTCTGGGACAGACTTCACT

CTCACCATCAGCAGCCTAGAGCCTGAAGATTTTGCAGTTTATTACTGTCAGC

AGCGTAGCCACTGGCTCACTTTCGGCGGGGGGACCAAGGTGGAGATCAAA

CGTACGGTG
```

2105 L-chain amino acid sequence

MEAPAQLLFLLLLWLPDTTGEIVLTQSPATLSLSPGERATLSCRASQSVSSYLA    (SEQ ID NO: 34)

WYQQKPGQAPRLLIYDASNRATGIPARFSGSGSGTDFTLTISSLEPEDFAVYYC

QQRSHWLTFGGGTKVEIKRTV

DNAs of 110 encoding the H-chain variable region and L-chain variable region and the amino acid sequences of the H-chain and L-chain are respectively shown below.

The translation initiation point of the H-chain DNA is an ATG codon that begins from the 60th adenine (A) from the 5' end of SEQ ID NO: 35. The boundary of the antibody variable region and the constant region is located between the 479th adenine (A) and the 480th guanine (G) from the 5'end. In the amino acid sequence, the H-chain variable region ranges from the N-terminus of SEQ ID NO: 36 to the 140th serine (S) residue, and the constant region is of the 141st alanine (A) and the following residues. It was predicted by gene sequence prediction software (Signal P ver.2) that the H-chain signal sequence ranges from the N-terminus to the 19th cystein (C) of SEQ ID NO: 36. It is thought that the N-terminus of the mature protein is the 20th glutamine (Q) of SEQ ID NO: 36.

The translation initiation point of the L-chain DNA is an ATG codon that begins from the 35th A from the 5' end of SEQ ID NO: 37, and the variable region ranges from the 5' end to the 421st adenine (A). In the amino acid sequence, the variable region ranges from the N-terminus to the 129th lysine (K) of SEQ ID NO: 38. It was predicted by gene sequence prediction software (Signal P ver.2) that the L-chain signal sequence ranges from the N-terminus to the 22nd cystein (C) of SEQ ID NO: 38. It is thought that the N-terminus of the mature protein is the 23rd valine (V) of SEQ ID NO: 38.

110 H-chain

```
CTGAACACAGACCCGTCGACTTCCATTCGGTGATCAGCACTGAACACAGA    (SEQ ID NO: 35)

GGACTCACCATGGAGTTTGGGCTGAGCTGGGTTTTCCTCGTTGCTCTTTTA

AGAGGTGTCCAGTGTCAGGTGCAGCTGGTGGAGTCTGGGGGAGGCGTGGT

CCAGCCTGGGAGGTCCCTGAGACTCTCCTGTGCAGCGTCTGGATTCACCTT
```

-continued

```
CAGTAGCTATGGCATGCACTGGGTCCGCCAGGCTCCAGGCAAGGGGCTGG

AGTGGGTGGCAGTTATATGGTATGATGGAAGTATTAAATACTATGCAGACTC

CGTGAAGGGCCGATTCACCATCTCCAGAGACAATTCCAAGAACACGCTGTA

TCTGCAAATGAACAGCCTGAGAGCCGAGGACACGGCTGTGTATTACTGTGC

GAGAGAGGGCTACAATATTTTGACTGGTTATTTTGGCTACTGGGGCCAGGG

AACCCTGGTCACCGTCTCCTCAGCTAGCACCAAGGG

110 H-chain amino acid sequence

MEFGLSWVFLVALLRGVQCQVQLVESGGGVVQPGRSLRLSCAASGFTFSSYG      (SEQ ID NO: 36)

MHWVRQAPGKGLEWVAVIWYDGSIKYYADSVKGRFTISRDNSKNTLYLQMN

SLRAEDTAVYYCAREGYNILTGYFGYWGQGTLVTVSSASTK

110 L-chain

TCACAGATCTAGTCAGACCCAGTCAGGACACAGCATGGACATGAGGGTCC      (SEQ ID NO: 37)

CCGCTCAGCTCCTGGGGCTCCTGCTGCTCTGGCTCCCAGGTGCCAGATGTG

TCATCTGGATGACCCAGTCTCCATCCTTACTCTCTGCATCTACAGGAGACAG

AGTCACCATCAGTTGTCGGATGAGTCAGGGCATTAGCAGTGATTTAGCCTG

GTATCAGCAAAAACCAGGGAAAGCCCCTGAGCTCCTGATCTCTGCTGCATC

CACTTTGCAAAGTGGGGTCCCATCAAGGTTCAGTGGCAGTGGATCTGGGA

CAGATTTCACTCTCACCATCAGCTGCCTGCAGTCTGAAGATTTTGCAACTTA

TTACTGTCAACAGTATTATAGTTTTCCGTGGACGTTCGGCCAAGGGACCAA

GGTGGAAATCAAACGTACG

110 L-chain amino acid sequence

MDMRVPAQLLGLLLLWLPGARCVIWMTQSPSLLSASTGDRVTISCRMSQGISS     (SEQ ID NO: 38)

DLAWYQQKPGKAPELLISAASTLQSGVPSRFSGSGSGTDFTLTISCLQSEDFAT

YYCQQYYSFPWTFGQGTKVEIKRT
```

DNAs of 115 encoding the H-chain variable region and L-chain variable region and the amino acid sequences of the H-chain and L-chain are respectively shown below.

The translation initiation point of the H-chain DNA is an ATG codon that begins from the 60th adenine (A) from the 5' end of SEQ ID NO: 39. The boundary of the antibody variable region and the constant region is located between the 479th adenine (A) and the 480th guanine (G) from the 5'end. In the amino acid sequence, the H-chain variable region ranges from the N-terminus of SEQ ID NO: 40 to the 140th serine (S) residue, and the constant region is of the 141st alanine (A) and the following residues. It was predicted by gene sequence prediction software (Signal P ver.2) that the H-chain signal sequence ranges from the N-terminus to the 19th cystein (C) of SEQ ID NO: 40. It is thought that the N-terminus of the mature protein is the 20th glutamine (Q) of SEQ ID NO: 40.

The translation initiation point of the L-chain DNA is an ATG codon that begins from the 35th A from the 5' end of SEQ ID NO: 41, and the variable region ranges from the 5' end to the 421st adenine (A). In the amino acid sequence, the variable region ranges from the N-terminus to the 129th lysine (K) of SEQ ID NO: 42. It was predicted by gene sequence prediction software (Signal P ver.2) that the L-chain signal sequence ranges from the N-terminus to the 22nd cystein (C) of SEQ ID NO: 42. It is thought that the N-terminus of the mature protein is the 23rd valine (V) of SEQ ID NO: 42.

```
115 H-chain

CTGAACACAGACCCGTCGACTTCCATTCGGTGATCAGCACTGAACACAGA      (SEQ ID NO: 39)

GGACTCACCATGGAGTTTGGGCTGAGCTGGGTTTTCCTCGTTGCTCTTTTA

AGAGGTGTCCAGTGTCAGGTGCAGCTGGTGGAGTCTGGGGGAGGCGTGGT

CCAGCCTGGGAGGTCCCTGAGACTCTCCTGTGCAGCGTCTGGATTCACCTT
```

```
CAGTAGCTATGGCATGCACTGGGTCCGCCAGGCTCCAGGCAAGGGGCTGG

AGTGGGTGGCAGTTATATGGAATGATGGAAGTATTAAATACTATGCAGACTC

CGTGAAGGGCCGATTCACCATCTCCAGAGACAATTCCAAGAACACGCTGTA

TCTGCAAATGAACAGCCTGAGAGCCGAGGACACGGCTGTGTATTACTGTGC

GAGAGAGGGCTACAATATTTTGACTGGTTATTTTGGCTACTGGGGCCAGGG

AACCCTGGTCACCGTCTCCTCAGCTAGCACCAAGG

115 H-chain amino acid sequence

MEFGLSWVFLVALLRGVQCQVQLVESGGGVVQPGRSLRLSCAASGFTFSSYG    (SEQ ID NO: 40)

MHWVRQAPGKGLEWVAVIWNDGSIKYYADSVKGRFTISRDNSKNTLYLQMN

SLRAEDTAVYYCAREGYNILTGYFGYWGQGTLVTVSSASTK

115 L-chain

TCACAGATCTAGTCAGACCCAGTCAGGACACAGCATGGACATGAGGGTCC    (SEQ ID NO: 41)

CCGCTCAGCTCCTGGGGCTCCTGCTGCTCTGGCTCCCAGGTGCCAGATGTG

TCATCTGGATGACCCAGTCTCCATCCTTACTCTCTGCATCTACAGGAGACAG

AGTCACCATCAGTTGTCGGATGAGTCAGGGCATTAGCAGTGATTTAGCCTG

GTATCAGCAAAAACCAGGGAAAGCCCCTGAGCTCCTGATCTCTGCTGCATC

CACTTTGCAAAGTGGGGTCCCATCAAGGTTCAGTGGCAGTGGATCTGGGA

CAGATTTCACTCTCACCATCAGCTGCCTGCAGTCTGAAGATTTTGCAACTTA

TTACTGTCAACAGTATTATAGTTTTCCGTGGACGTTCGGCCAAGGGACCAA

GGTGGAAATCAAACGTACG

115 L-chain amino acid sequence

MDMRVPAQLLGLLLLWLPGARCVIWMTQSPSLLSASTGDRVTISCRMSQGISS    (SEQ ID NO: 42)

DLAWYQQKPGKAPELLISAASTLQSGVPSRFSGSGSGTDFTLTISCLQSEDFAT

YYCQQYYSFPWTFGQGTKVEIKRT
```

DNAs of 281-1-10 encoding the H-chain variable region and L-chain variable region and the amino acid sequences of the H-chain and L-chain are respectively shown below.

The translation initiation point of the H-chain DNA is an ATG codon that begins from the 52nd adenine (A) from the 5' end of SEQ ID NO: 43. The boundary of the antibody variable region and the constant region is located between the 468th adenine (A) and the 469th guanine (G) from the 5'end. In the amino acid sequence, the H-chain variable region ranges from the N-terminus of SEQ ID NO: 44 to the 139th serine (S) residue, and the constant region is of the 140th alanine (A) and the following residues. It was predicted by gene sequence prediction software (Signal P ver.2) that the H-chain signal sequence ranges from the N-terminus to the 19th serine (S) of SEQ ID NO: 44. It is thought that the N-terminus of the mature protein is the 20th glutamine (Q) of SEQ ID NO: 44.

The translation initiation point of the L-chain DNA is an ATG codon that begins from the 41st A from the 5' end of SEQ ID NO: 45, and the variable region ranges from the 5' end to the 424th adenine (A). In the amino acid sequence, the variable region ranges from the N-terminus to the 128th lysine (K) of SEQ ID NO: 46. It was predicted by gene sequence prediction software (Signal P ver.2) that the L-chain signal sequence ranges from the N-terminus to the 20th glycine (G) of SEQ ID NO: 46. It is thought that the N-terminus of the mature protein is the 21st glutamic acid (E) of SEQ ID NO: 46.

```
281-1-10 H-chain

CTGAACACAGACCCGTCGACTTTGAGAGTCCTGGACCTCCTGTGCAAGAA    (SEQ ID NO: 43)

CATGAAACATCTGTGGTTCTTCCTTCTCCTGGTGGCAGCTCCCAGATGGGT

CCTGTCCCAGGTGCAGCTGCAGGAGTCGGGCCCAGGACTGGTGAAGCCTT

CGGAGACCCTGTCCCTCACCTGCACTGTCTCTGGTGGCTCCATCAGTGGTT
```

ACTACTGGAGCTGGATCCGGCAGCCCCAGGGAAGGGACTGGAGTGGATT

GGGTATATCTATTACAGTGGGAGCACCAACTACAATCCCTCCCTCAAGAGTC

GAGTCACCATATCAGTAGACACGTCCAAGAACCAGTTCTCCCTGAAGCTGA

ATTCTGTGACCGCTGCGGACACGGCCGTGTATTACTGTGCGAGAGCCCCCT

TGCACGGTGACTACAAATGGTTCCACCCCTGGGGCCAGGGAACCCTGGTC

ACCGTCTCCTCAGCTAGCACCAAGG 281-1-10 H-chain amino acid sequence

MKHLWFFLLLVAAPRWVLSQVQLQESGPGLVKPSETLSLTCTVSGGSISGYY     (SEQ ID NO: 44)

WSWIRQPPGKGLEWIGYIYYSGSTNYNPSLKSRVTISVDTSKNQFSLKLNSVT

AADTAVYYCARAPLHGDYKWFHPWGQGTLVTVSSASTK 281-1-10 L-chain

TCACAGATCTGAGCTGCTCAGTTAGGACCCAGAGGGAACCATGGAAACCC     (SEQ ID NO: 45)

CAGCGCAGCTTCTCTTCCTCCTGCTACTCTGGCTCCCAGATACCACCGGAG

AAATTGTGTTGACGCAGTCTCCAGGCACCCTGTCTTTGTCTCCAGGGGAAA

GAGCCACCCTCTCCTGCAGGGCCAGTCAGAGTGTTAGCAGCAGCTACTTAG

CCTGGTACCAGCAGAAACCTGGCCAGGCTCCCAGGCTCCTCATCTATGGTG

CATCCAGCAGGGCCACTGGCATCCCAGACAGGTTCAGTGGCAGTGGGTCT

GGGACAGACTTCACTCTCACCATCAGCAGACTGGAGCCTGAAGATTTTGCA

GTGTATTACTGTCAGCAGTATGGTAGCTCACCGATCACCTTCGGCCAAGGG

ACACGACTGGAGATCAAACGTACG 281-1-10 L-chain amino acid sequence

METPAQLLFLLLLWLPDTTGEIVLTQSPGTLSLSPGERATLSCRASQSVSSSYL     (SEQ ID NO: 46)

AWYQQKPGQAPRLLIYGASSRATGIPDRFSGSGSGTDFTLTISRLEPEDFAVYY

CQQYGSSPITFGQGTRLEIKRT

DNAs of 4D11 encoding the H-chain variable region and L-chain variable region and the amino acid sequences of the H-chain and L-chain are respectively shown below.

The translation initiation point of the H-chain DNA is an ATG codon that begins from the 16th adenine (A) from the 5' end of SEQ ID NO: 47. The boundary of the antibody variable region and the constant region is located between the 456th adenine (A) and the 457th guanine (G) from the 5'end. In the amino acid sequence, the H-chain variable region ranges from the N-terminus of SEQ ID NO: 48 to the 147th serine (S) residue, and the constant region is of the 148th alanine (A) and the following residues. It was predicted by gene sequence prediction software (Signal P ver.2) that the H-chain signal sequence ranges from the N-terminus to the 26th serine (S) of SEQ ID NO: 48. It is thought that the N-terminus of the mature protein is the 27th glutamine (Q) of SEQ ID NO: 48.

The translation initiation point of the L-chain DNA is an ATG codon that begins from the 59th A from the 5' end of SEQ ID NO: 49, and the variable region ranges from the 5' end to the 442nd adenine (A). In the amino acid sequence, the variable region ranges from the N-terminus to the 128th lysine (K) of SEQ ID NO: 50. It was predicted by gene sequence prediction software (Signal P ver.2) that the L-chain signal sequence ranges from the N-terminus to the 22nd cystein (C) of SEQ ID NO: 50. It is thought that the N-terminus of the mature protein is the 21st alanine (A) of SEQ ID NO: 50.

4D11 H-chain

ATATGTCGACGAGTCATGGATCTCATGTGCAAGAAAATGAAGCACCTGTGG     (SEQ ID NO: 47)

TTCTTCCTCCTGCTGGTGGCGGCTCCCAGATGGGTCCTGTCCCAGCTGCAG

CTGCAGGAGTCGGGCCCAGGACTACTGAAGCCTTCGGAGACCCTGTCCCT

CACCTGCACTGTCTCTGGCGGCTCCATCAGCAGTCCTGGTTACTACGGGGG

```
CTGGATCCGCCAGCCCCCAGGGAAGGGGCTGGAGTGGATTGGGAGTATCTA

TAAAAGTGGGAGCACCTACCACAACCCGTCCCTCAAGAGTCGAGTCACCA

TATCCGTAGACACGTCCAAGAACCAGTTCTCCCTGAAGCTGAGCTCTGTGA

CCGCCGCAGACACGGCTGTGTATTACTGTACGAGACCTGTAGTACGATATTT

TGGGTGGTTCGACCCCTGGGGCCAGGGAACCCTGGTCACCGTCTCCTCAG

CTAGC

4D11 H-chain amino acid sequence

MDLMCKKMKHLWFFLLLVAAPRWVLSQLQLQESGPGLLKPSETLSLTCTVSG    (SEQ ID NO: 48)

GSISSPGYYGGWIRQPPGKGLEWIGSIYKSGSTYHNPSLKSRVTISVDTSKNQF

SLKLSSVTAADTAVYYCTRPVVRYFGWFDPWGQGTLVTVSSAS

4D11 L-chain

AGATCTTAAGCAAGTGTAACAACTCAGAGTACGCGGGGAGACCCACTCAG     (SEQ ID NO: 49)

GACACAGCATGGACATGAGGGTCCCCGCTCAGCTCCTGGGGCTTCTGCTGC

TCTGGCTCCCAGGTGCCAGATGTGCCATCCAGTTGACCCAGTCTCCATCCT

CCCTGTCTGCATCTGTAGGAGACAGAGTCACCATCACTTGCCGGGCAAGTC

AGGGCATTAGCAGTGCTTTAGCCTGGTATCAGCAGAAACCAGGGAAAGCT

CCTAAGCTCCTGATCTATGATGCCTCCAATTTGGAAAGTGGGGTCCCATCAA

GGTTCAGCGGCAGTGGATCTGGGACAGATTTCACTCTCACCATCAGCAGCC

TGCAGCCTGAAGATTTTGCAACTTATTACTGTCAACAGTTTAATAGTTACCC

GACGTTCGGCCAAGGGACCAAGGTGGAAATCAAACGTACG

4D11 L-chain amino acid sequence

MDMRVPAQLLGLLLLWLPGARCAIQLTQSPSSLSASVGDRVTITCRASQGISS   (SEQ ID NO: 50)

ALAWYQQKPGKAPKLLIYDASNLESGVPSRFSGSGSGTDFTLTISSLQPEDFAT

YYCQQFNSYPTFGQGTKVEIKRT
```

DNAs of KM643-4-11 encoding the H-chain variable region and L-chain variable region and the amino acid sequences of the H-chain and L-chain are respectively shown below.

The translation initiation point of the H-chain DNA is an ATG codon that begins from the 1st adenine (A) from the 5' end of SEQ ID NO: 51. The boundary of the antibody variable region and the constant region is located between the 447th adenine (A) and the 448th guanine (G) from the 5'end. In the amino acid sequence, the H-chain variable region ranges from the N-terminus of SEQ ID NO: 52 to the 149th serine (S) residue, and the constant region is of the 150th alanine (A) and the following residues. It was predicted by gene sequence prediction software (Signal P ver.2) that the H-chain signal sequence ranges from the N-terminus to the 20th serine (S) of SEQ ID NO: 52. It is thought that the N-terminus of the mature protein is the 21st glutamine (Q) of SEQ ID NO: 52.

The translation initiation point of the L-chain DNA is an ATG codon that begins from the 38th A from the 5' end of SEQ ID NO: 53, and the variable region ranges from the 5' end to the 409th adenine (A). In the amino acid sequence, the variable region ranges from the N-terminus to the 124th lysine (K) of SEQ ID NO: 54. It was predicted by gene sequence prediction software (Signal P ver.2) that the L-chain signal sequence ranges from the N-terminus to the 20th glycine (G) of SEQ ID NO: 54. It is thought that the N-terminus of the mature protein is the 21st Glutamic acid (E) of SEQ ID NO: 54.

```
KM643-4-11 H-chain

ATGTCTGTCTCCTTCCTCATCTTCCTGCCCGTGCTGGGCCTCCCATGGGGTG   (SEQ ID NO: 51)

TCCTGTCACAGGTACAGCTGCAGCAGTCAGGTCCAGGACTGGTGAAGCCC

TCGCAGACCCTCTCATTCACCTGTGCCATCTCCGGGGACAGTGTCTCTAGC
```

-continued
```
AACAGTGCTGCTTGGAACTGGATCAGGCAGTCCCCATCGAGAGGCCTTGA

GTGGCTGGGAAGGACATACTACAGGTCCAAGTGGTATAAAGATTATGCAGT

ATCTGTGAAAAGTCGAATAACCATCAACCCAGACACATCCAAGAACCAGTT

CTCCCTGCAGCTGAACTCTGTGACCCCCGAGGACACGGCTGTGTATTACTG

TGCAAGAGGGTATTACTATGGTTCGGGGAGCTATCCCTACTACTACCAAATG

GACGTCTGGGGCCAAGGGACCACGGTCACCGTCTCCTCAGCTAGC

KM643-4-11 H-chain amino acid sequence

MSVSFLIFLPVLGLPWGVLSQVQLQQSGPGLVKPSQTLSFTCAISGDSVSSNSA    (SEQ ID NO: 52)

AWNWIRQSPSRGLEWLGRTYYRSKWYKDYAVSVKSRITINPDTSKNQFSLQL

NSVTPEDTAVYYCARGYYYGSGSYPYYYQMDVWGQGTTVTVSSAS

KM643-4-11 L-chain

AATTGAGGAACTGCTCAGTTAGGACCCAGAGGGAACCATGGAAGCCCCAG         (SEQ ID NO: 53)

CTCAGCTTCTCTTCCTCCTGCTACTCTGGCTCCCAGATACCACCGGAGAAAT

TGTGTTGACACAGTCTCCAGCCACCCTGTCTTTGTCTCCAGGGGAAAGTGC

CACCCTCTCCTGCAGGGCCAGTCAGAGTGTTAGCAGCTACTTAGCCTGGTA

CCAACAGAAACCTGGCCAGGCTCCCAGGCTCCTCATCTATGATGCATCCAA

CAGGGCCACTGGCATCCCAGCCAGGTTCAGTGGCAGTGGGTCTGGGACAG

ACTTCACTCTCACCATCAGCAGCCTAGAGCCTGAAGATTTTGCAGTTTATTA

CTGTCAGCAGCGTAGCAACACTTTCGGCGGAGGGACCAAGGTGGAGATCA

AACGAAC

KM643-4-11 L-chain amino acid sequence

MEAPAQLLFLLLLWLPDTTGEIVLTQSPATLSLSPGESATLSCRASQSVSSYLA    (SEQ ID NO: 54)

WYQQKPGQAPRLLIYDASNRATGIPARFSGSGSGTDFTLTISSLEPEDFAVYYC

QQRSNTFGGGTKVEIKR
```

DNAs of F4-465 encoding the H-chain variable region and L-chain variable region and the amino acid sequences of the H-chain and L-chain are respectively shown below.

The translation initiation point of the H-chain DNA is an ATG codon that begins from the 47th adenine (A) from the 5' end of SEQ ID NO: 55. The boundary of the antibody variable region and the constant region is located between the 484th adenine (A) and the 445th guanine (G) from the 5'end. In the amino acid sequence, the H-chain variable region ranges from the N-terminus of SEQ ID NO: 56 to the 146th serine (S) residue, and the constant region is of the 147th alanine (A) and the following residues. It was predicted by gene sequence prediction software (Signal P ver.2) that the H-chain signal sequence ranges from the N-terminus to the 19th serine (S) of SEQ ID NO: 56. It is thought that the N-terminus of the mature protein is the 20th glutamine (Q) of SEQ ID NO: 56.

The translation initiation point of the L-chain DNA is an ATG codon that begins from the 81st A from the 5' end of SEQ ID NO: 57, and the variable region ranges from the 5' end to the 440th (C). In the amino acid sequence, the variable region ranges from the N-terminus to the 120th Threonine (T) of SEQ ID NO: 58. It was predicted by gene sequence prediction software (Signal P ver.2) that the L-chain signal sequence ranges from the N-terminus to the 19th alanine (G) of SEQ ID NO: 58. It is thought that the N-terminus of the mature protein is the 20th serine (S) of SEQ ID NO: 58.

```
                    F4-465 H-chain

CTGAACACAGACCCGTCGACTACGCGGGAGACCACAGCTCCACACCATGG      (SEQ ID NO: 55)

ACTGGACCTGGAGGATCCTATTCTTGGTGGCAGCAGCAACAGGTGCCCACT

CCCAGGTGCAGCTGGTGCAATCTGGGTCTGAGTTGAAGAAGCCTGGGGCC

TCAGTGAAGGTCCCCTGCAAGGCTTCTGGATACACCTTCACTAGCTATGCTA
```

```
TGAATTGGGTGCGACAGGCCCCTGGACAAGGGCTTGAGTGGATGGGATGG

ATCAACACCAACACTGGGAACCCAACGTATGCCCAGGGCTTCACAGGACG

GTTTGTCTTCTCCTTGGACACCTCTGTCAGCACGGCATATCTGCAGATCAGC

AGCCTAAAGGCTGAGGACACTGCCGTGTATTACTGTGCGAGAGAGGTAGTA

CCAGTTGCTATGAGGGTAACTCACTACTACTACGGTATGGACGTCTGGGGC

CAAGGGACCACGGTCACCGTCTCCTCAGCTAGCACCAA

F4-465 H-chain amino acid sequence

MDWTWRILFLVAAATGAHSQVQLVQSGSELKKPGASVKVPCKASGYTFTSYA    (SEQ ID NO: 56)

MNWVRQAPGQGLEWMGWINTNTGNPTYAQGFTGRFVFSLDTSVSTAYLQIS

SLKAEDTAVYYCAREVVPVAMRVTHYYYGMDVWGQGTTVTVSSAST

F4-465 L-chain

CTGGGTACGGTAACCGTCAGATCGCCTGGAGACGCCATCACAGATCTGCCT    (SEQ ID NO: 57)

CAGGAAGCAGCATCGGAGGTGCCTCAGCCATGGCATGGATCCCTCTCTTCC

TCGGCGTCCTTGTTTACTGCACAGGATCCGTGGCCTCCTATGAGCTGACTC

AGCCACCCTCAGTGTCCGTGGCCCCAGGACAGACAGCCAGCATCACCTGT

TCTGGAGATAAATTGGGGGATAATTTTACTTGCTGGTATCAGCAGAAGCCA

GGCCAGTCCCCTGTGCTGGTCATCTTTCAGGATTGGAAGCGGCGCCCAGGG

ATCCCTGCGCGATTCTCTGGCTCCAAGTCTGGGAACACAGCCACTCTGACC

ATCAGCGGGACCCAGGCTATGGATGAGGCTGACTATTACTGTCAGGCGTGG

GACATCAGCACTGTGGTATTCGGCGGAGGGACCAAGCTGACCGTCCTAGGT

CAGCCCAAGGCTGCCCCCTCGGTCACTCTGTTCCCGCCCTCCTCTGAGGAG

CTTCAAGCCAACAAGGCCACACTGGTGTGTCTCATAAGTGACTTCTACCCG

GGAGCCGTGACAGTGGCCTGGAAGGCAGATAGCAGCCCCGTCAAGGCGGG

AGTGGAGACCACCACACCCTCCAAACAAAGCAACAACAAGTACGCGGCC

AGCAGCTACCTGAGCCTGACGCCTGAGCAGTGGAAGTCCCACAGAAGCTA

CAGCTGCCAGGTCACGCATGAAGGGAGCACCGTGGAGAAGACAGTGGCCC

CTACAGAATGTTCATGAATTCAGATCCGTTAACGGTTACCAACTACCTAGAC

TGGATTCGTGACCAACATA

F4-465 L-chain amino acid sequence

MAWIPLFLGVLVYCTGSVASYELTQPPSVSVAPGQTASITCSGDKLGDNFTCW    (SEQ ID NO: 58)

YQQKPGQSPVLVIFQDWKRRPGIPARFSGSKSGNTATLTISGTQAMDEADYYC

QAWDISTVVFGGGTKLTVLGQPKAAPSVTLFPPSSEELQANKATLVCLISDFYP

GAVTVAWKADSSPVKAGVETTTPSKQSNNKYAASSYLSLTPEQWKSHRSYSC

QVTHEGSTVEKTVAPTECS
```

DNAs of F2-103 encoding the H-chain variable region and L-chain variable region and the amino acid sequences of the H-chain and L-chain are respectively shown below.

The translation initiation point of the H-chain DNA is an ATG codon that begins from the 32nd adenine (A) from the 5' end of SEQ ID NO: 59. The boundary of the antibody variable region and the constant region is located between the 463rd adenine (A) and the 464th Guanine (G) from the 5'end. In the amino acid sequence, the H-chain variable region ranges from the N-terminus of SEQ ID NO: 60 to the 144th Serine (S) residue, and the constant region is of the 145th Alanine (A) and the following residues. It was predicted by gene sequence prediction software (Signal P ver.2) that the H-chain signal sequence ranges from the N-terminus to the 19th Cystein (C) of SEQ ID NO: 60. It is thought that the N-terminus of the mature protein is the 20th Glutamic acid (E) of SEQ ID NO: 60.

The translation initiation point of the L-chain DNA is an ATG codon that begins from the 29th A from the 5' end of SEQ ID NO: 61, and the variable region ranges from the 5' end to the 415th adenine (A). In the amino acid sequence, the variable region ranges from the N-terminus to the 129th Lysine (K) of SEQ ID NO: 62. It was predicted by gene sequence prediction software (Signal P ver.2) that the L-chain signal sequence ranges from the N-terminus to the 22nd Cystein (C) of SEQ ID NO: 62. It is thought that the N-terminus of the mature protein is the 23rd Asp (D) of SEQ ID NO: 62.

```
F2-103 H-chain

GCTGATCAGGACTGCACACAGAGAACTCACCATGGAGTTTGGGCTGAGCT       (SEQ ID NO: 59)

GGGTTTTCCTTGTTGCTATTTTAAAAGGTGTCCAGTGTGAGGTGCAGCTGG

TGGAGTCCGGGGGAGGCTTAGTTCAGCCTGGGGGGTCCCTGAGACTCTCC

TGTGCAGTCTCTGGATTCACCTTCAGTACCTACTGGATGCACTGGGTCCGC

CAAGCTCCAGGGAAGGGGCTGGTGTGGGTCTCACGTATTAATAGTGATGGG

AGTAGCACAACCTACGCGGACTCCGTGAAGGGCCGATTCACCATCTCCAGA

GACAACGCCAAGAACACGCTGTATCTGCAAATGAACAGTCTGAGAGCCGA

GGACACGGCTGTGTATTACTGTGCAAGAGATAGAGTACTATGGATCGGGGA

GTTATCCTACTACGGTATGGACGTCTGGGGCCAAGGGACCACGGTCACCGT

CTCCTCAGCTAGCACCAAGGGCCCATCGGTCTTCCCCCTGGCACCCTCCTC

CAAGAGCACCTCT

F2-103 H-chain amino acid sequence

MEFGLSWVFLVAILKGVQCEVQLVESGGGLVQPGGSLRLSCAVSGFTFSTYW     (SEQ ID NO: 60)

MHWVRQAPGKGLVWVSRINSDGSSTTYADSVKGRFTISRDNAKNTLYLQMN

SLRAEDTAVYYCARDRVLWIGELSYYGMDVWGQGTTVTVSSASTKGPSVFPL

APSSKSTS

F2-103 L-chain

GGGGAGTCAGACCCAGTCAGGACACAGCATGGACATGAGGGTCCCCGCTC      (SEQ ID NO: 61)

AGCTCCTGGGGCTCCTGCTGCTCTGGCTCCCAGGTGCCAAATGTGACATCC

AGATGACCCAGTCTCCTTCCACCCTGTCTGCATCTGTAGGAGACAGAGTCA

CCATCACTTGCCGGGCCAGTCAGAGTATTAGTAACTGGTTGGCCTGGTATC

AGCAGAAACCAGGGAAAGCCCCTAAGCTCCTGCTCTATAAGGCATCTGGTT

TAGAAAGTGGGGTCCCATCAAGGTTCAGCGGCAGTGGATCTGGGACAGAA

TTCACTCTCACCATCAACAGCCTGCAGCCTGATGATTTTGCAACTTATTACT

GCCAACAGTCTAATAGTTATTCGTGGACGTTCGGCCACGGGACCAAGGTGG

AAATCAAACGTACGGTGGCTGCACCATCTGTCTTCATCTTCCCGCCATCTGA

TGAGCAGTTGAAATCTGGAACTGCCTCTGTTGTGTGCCTGCTGAATAACTT

CTATCCCAGAGAGGCCAAAGTACAGTGGAAGGTGGATAACGCCCTCCAATC

GGGTAACTCCCAGGAGAGTGTCACAGAGCAGGACAGCAAGGACAGCACCT

ACAGCCTCAGCAGCACCCTGACGCTGAGCAAAGCAGACTACGAGAAACAC

AAAGTCTACGCCTGCGAAGTCACCCATCAGGGCCTGA

F2-103 L-chain amino acid sequence

MDMRVPAQLLGLLLLWLPGAKCDIQMTQSPSTLSASVGDRVTITCRASQSISN    (SEQ ID NO: 62)

WLAWYQQKPGKAPKLLLYKASGLESGVPSRFSGSGSGTEFTLTINSLQPDDFA
```

-continued
TYYCQQSNSYSWTFGHGTKVEIKRTVAAPSVFIFPPSDEQLKSGTASVVCLLN

NFYPREAKVQWKVDNALQSGNSQESVTEQDSKDSTYSLSSTLTLSKADYEKH

KVYACEVTHQGL

DNAs of F5-77 encoding the H-chain variable region and L-chain variable region and the amino acid sequences of the H-chain and L-chain are respectively shown below.

The translation initiation point of the H-chain DNA is an ATG codon that begins from the 100th adenine (A) from the 5' end of SEQ ID NO: 63. The boundary of the antibody variable region and the constant region is located between the 528th adenine (A) and the 529th Guanine (G) from the 5'end. In the amino acid sequence, the H-chain variable region ranges from the N-terminus of SEQ ID NO: 64 to the 143rd Serine (S) residue, and the constant region is of the 144th Alanine (A) and the following residues. It was predicted by gene sequence prediction software (Signal P ver.2) that the H-chain signal sequence ranges from the N-terminus to the 19th Cystein (C) of SEQ ID NO: 64. It is thought that the N-terminus of the mature protein is the 20th Glutamic acid (E) of SEQ ID NO: 64.

The translation initiation point of the L-chain DNA is an ATG codon that begins from the 59th A from the 5' end of SEQ ID NO: 65, and the variable region ranges from the 5' end to the 445th adenine (A). In the amino acid sequence, the variable region ranges from the N-terminus to the 129th Lysine (K) of SEQ ID NO: 66. It was predicted by gene sequence prediction software (Signal P ver.2) that the L-chain signal sequence ranges from the N-terminus to the 22nd Cystein (C) of SEQ ID NO: 66. It is thought that the N-terminus of the mature protein is the 23rd Asp (D) of SEQ ID NO: 66.

```
F5-77 H-chain

GGTCTATATAAGCAGAGCTGGGTACGTCCTCACATTCAGTGATCAGCACTG     (SEQ ID NO: 63)

AACACAGACCCGTCGACGGTGATCAGGACTGAACAGAGAGAACTCACCAT

GGAGTTTGGGCTGAGCTGGCTTTTTCTTGTGGCTATTTTAAAAGGTGTCCA

GTGTGAGGTGCAGCTGTTGGAGTCTGGGGGAGGCTTGGTACAGCCTGGGG

GGTCCCTGAGACTCTCCTGTGCAGCCTCTGGATTCACCTTTAGCAGCTATGC

CATGAGCTGGGTCCGCCAGGCTCCAGGGAAGGGGCTGGAGTGGGTCTCAG

CTATTAGTGGTAGTGGTGGTAGCACATACTACGCAGACTCCGTGAAGGGCC

GGTTCACCATCTCCAGAGACAATTCCAAGAACACGCTGTATCTGCAAATGA

ACAGCCTGAGAGCCGAGGACACGGCCGTATATTACTGTGCGAAAGATGGG

GGGTACTATGGTTCGGGGAGTTATGGGTACTTTGACTACTGGGGCCAGGGA

ACCCTGGTCACCGTCTCCTCAGCTAGCACCAAGGGCCCATCGGTCTTCCCC

CTGGCACCCTCCTCCAAGAGCACCTCTGGGGGCACAGCGGCCCTGGGCTG

CCTGGTCAAGGACTACTTCCCC

F5-77 H-chain amino acid sequence

MEFGLSWLFLVAILKGVQCEVQLLESGGGLVQPGGSLRLSCAASGFTFSSYAM    (SEQ ID NO: 64)

SWVRQAPGKGLEWVSAISGSGGSTYYADSVKGRFTISRDNSKNTLYLQMNSL

RAEDTAVYYCAKDGGYYGSGSYGYFDYWGQGTLVTVSSASTKGPSVFPLAP

SSKSTSGGTAALGCLVKDYFP

F5-77 L-chain

CAAGCAGTGGTAACAACGCAGAGTACGCGGGGGGAGTCAGACCCAGTCA      (SEQ ID NO: 65)

GGACACAGCATGGACATGAGGGTCCCCGCTCAGCTCCTGGGGCTCCTGCT

GCTCTGGTTCCCAGGTTCCAGATGCGACATCCAGATGACCCAGTCTCCATC

TTCCGTGTCTGGATCTGTAGGAGACAGAGTCACCATCACTTGTCGGGCGAG

TCAGGGTATTAGCAGCTGGTTAGCCTGGTATCAGCAGAAACCAGGGAAAG

CCCCTAAGCTCCTGATCTATGCTGGATCCAGTTTGCAAAGTGGGGTCCCATC
```

-continued
```
AAGGTTCAGCGGCAGTGGATTTGGGACAGATTTCACTCTCACCATCAGCAG

CCTGCAGCCTGAAGATTTTGCAACTTACTATTGTCAACAGGCTAGCAGTTT

CCCTCGGACATTCGGCCAAGGGACCAAGGTGGAGATCAAACGTACGGTGG

CTGCACCATCTGTCTTCATCTTCCCGCCATCTGATGAGCAGTTGAAATCTGG

AACTGCCTCTGTTGTGTGCCTGCTGAATAACTTCTATCCCAGAGAGGCCAA

AGTACAGTGGAAGGTGGATAACGCCCTCCAATCGGGTAACTCCCAGGAGA

GTGTCACAGAGCAGGACAGCAAGGACAGCACCTACAGCCTCAGCAGCACC

CTGACGCTGAGCAAAGCAGACTACGAGAAACACAAAGTCTACGCCTGCGA

AGTCACCCATCAGGGCCTGA

F5-77 L-chain amino acid sequence

MDMRVPAQLLGLLLLWFPGSRCDIQMTQSPSSVSGSVGDRVTITCRASQGISS    (SEQ ID NO: 66)

WLAWYQQKPGKAPKLLIYAGSSLQSGVPSRFSGSGFGTDFTLTISSLQPEDFAT

YYCQQASSFPRTFGQGTKVEIKRTVAAPSVFIFPPSDEQLKSGTASVVCLLNNF

YPREAKVQWKVDNALQSGNSQESVTEQDSKDSTYSLSSTLTLSKADYEKHK

VYACEVTHQGL
```

EXAMPLE 18

Expression of Antibody Protein in Animal Cell

The above obtained DNA fragment containing the variable region of the antibody was incorporated into an appropriate vector such as N5KG1 (IDEC Pharmaceuticals, U.S. Pat. No. 6,001,358), thereby preparing an antibody expression vector. As a host cell for expression, for example, CHO-Ras (Katakura Y., et al., Cytotechnology, 31: 103–109, 1999) is appropriately used. The vector can be introduced into the host cell by, for example, electroporation. Approximately 2 µg of the antibody expression vector was linearized with a restriction enzyme. The gene was introduced into $4 \times 10^7$ CHO-Ras cells under conditions of 350V and 500 µF using a Bio-Rad electrophoreter, and then inoculated to a 96-well culture plate. A drug corresponding to the selection marker of the expression vector was added, and culturing was continued. When colonies were observed, antibody-expressing lines were selected by the method described in Example 4. Antibodies can be purified from the selected cells according to Example 5.

EXAMPLE 19

Figure 18:
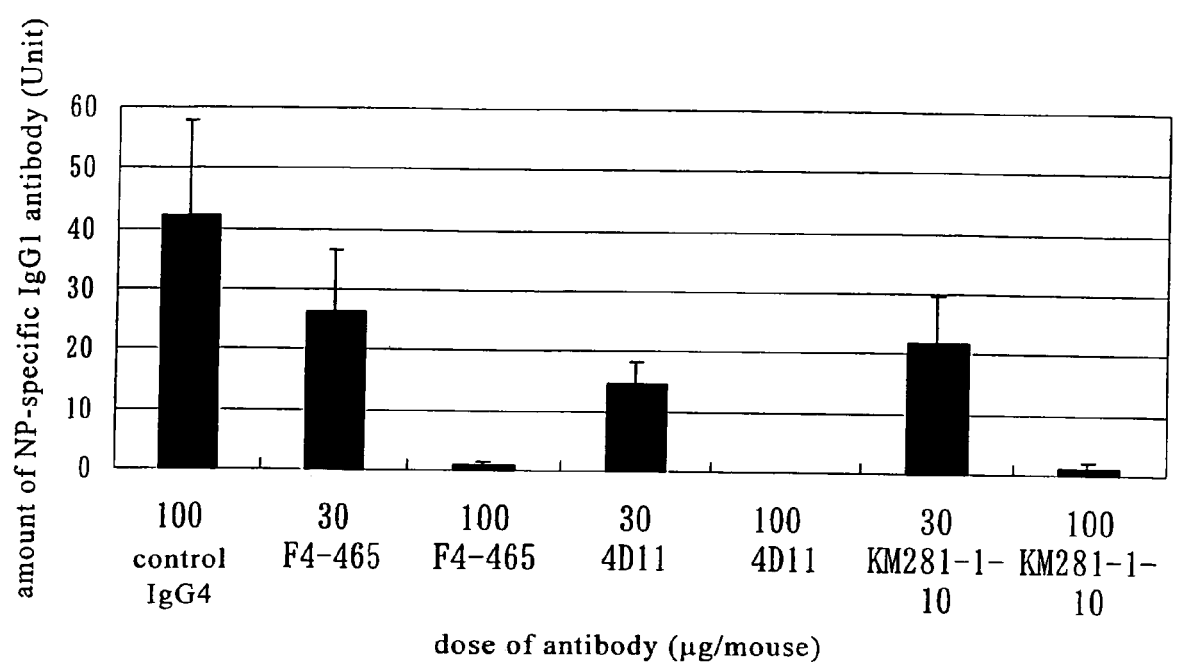
FIG. 18 shows that F4-465, 4D11 and KM281-1-10 suppressed antigen-specific IgG production.
Figure 19:
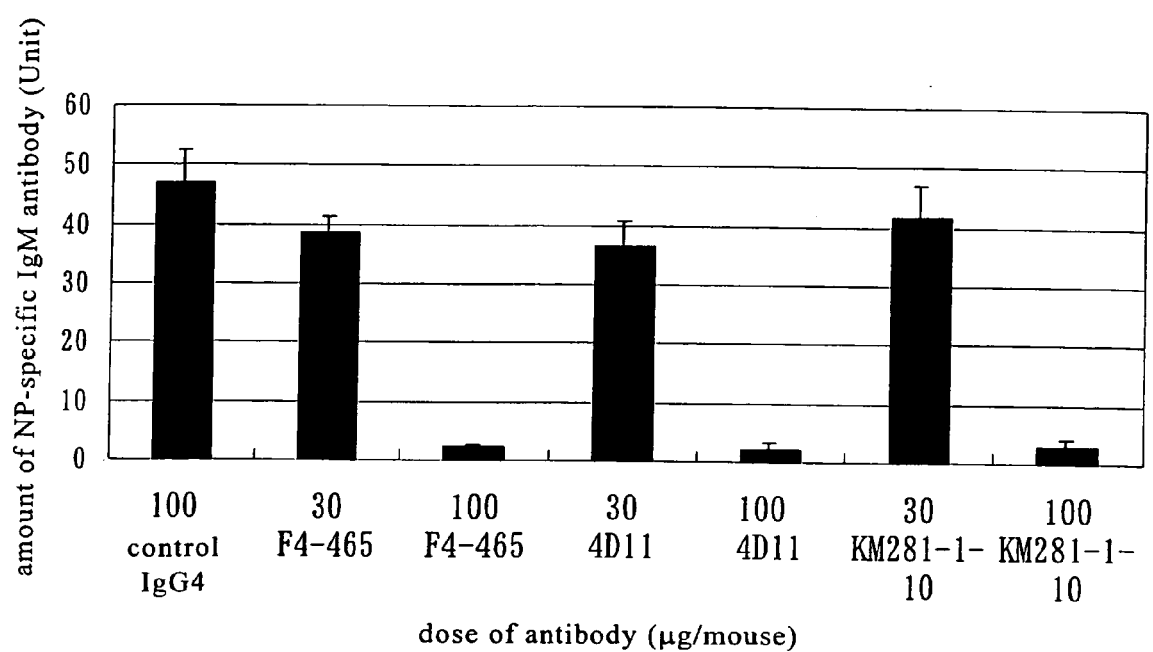
FIG. 19 shows that F4-465, 4D11 and KM281-1-10 suppressed antigen-specific IgM production.

Antigen-Specific Antibody Production Suppressive Action of CD40 Antagonistic Antibody Mice having a genetic background whereby they were homozygotes for mouse endogenous disrupted CD40 and harboring a transgene of a human CD40 gene (Yasui. et al. Int. Immunol. 2002 Vol 14: 319) were sensitized by intraperitoneally injecting 100 pg (in an amount of NP-CGG) of a complex of 4-hydroxy-3-nitrophenylacetyl-chicken γ-globulin conjugates (NP-CGG: distributed by Hitoshi KIKUTANI, Professor, Research Institute for Microbial Diseases, Osaka University) and ARAM (ARAM: Antigen Recognition Activation Motif). 30 or 100 µg of each monoclonal antibody was administered via caudate vein immediately before antigen sensitization. 100 µg of anti-human albumin human IgG4 antibody was administered as a negative control. 7 days after sensitization, blood was collected from the orbital venous plexus, and then the amounts of NP specific IgG1 and IgM antibodies in sera were measured by the ELISA method. The ELISA method was performed by adding NP-bound bovine serum albumin (NP-BSA: 2.5 µg/ml) (50 µl/well) to each well of a 96-well micro plate for ELISA (Maxisorp, Nunc), incubating at 4° C. and then absorbing NP-BSA. Next, the supernatant was discarded, a blocking reagent (Super Block, Pierce) was added to each well, and then incubation was performed at room temperature for blocking. Each well was then washed 3 times with a 0.1% Tween20-containing phosphate buffer (PBS-T). Subsequently, each serum diluted with 10% BlockAce-containing PBS-T was added (50 µl/well) to each well, followed by incubation at 37° C. for 2 hours for reaction. The microplate was washed 3 times with PBS-T. A solution prepared by diluting 1,000-fold alkaline phosphatase-labeled goat anti-mouse IgG1 or IgM antibody (COSMO BIO, 1070-04 or 1020-04) with 10% BlockAce-containing PBS-T was added (50 µl/well) to each well, followed by 2 hours of incubation at 37° C. Next, the microplate was washed 3 times with PBS-T, a chromogenic substrate solution (50 µl/well, Sigma104, phosphatase substrate) was added to each well, and then absorbance at a wavelength of 405 nm was measured with a microplate reader. FIGS. 18 and 19 show the results. In the figures, longitudinal axes indicate values obtained by conversion using as a unit the serum diluted 10,000-fold in the case of IgG1 antibody, and the serum diluted 100-fold in the case of IgM antibody. Here, the serum was prepared by injecting NP-CGG twice into C57BL/6 mice, collecting blood from the mice, and pooling the serum. Administration of 100 µg each of F4-465, 4D11 and KM281-1-10 antibodies strongly suppressed NP-specific IgG1 and IgM antibody production.

EXAMPLE 20

Proliferation Suppression of Tonsillar B cells by CD40 Antagonistic Antibody Human tonsils were obtained from Children's Hospital (San Diego, Calif., U.S.A.). Tonsils were cut into small pieces, minced, and then passed through a 70-micrometer nylon mesh cell strainer, thereby preparing a cell suspension. The cell suspension was washed several times with PBS, the cell number was counted, and then the suspension was cryopreserved with 90% human serum (ICN) and 10% DMSO. After thawing, the cells were re-suspended in a standard RPMI medium supplemented with 10% human serum and 2.5 μg/ml amphotericin (fangizon, Gibco/BRL), and then used.

$1 \times 10^5$ cells were added to a 96-well plate, and then anti-human CD40 antibodies were added at concentrations of 0.01, 0.1, 1.0 and 10 μg/ml. The test was conducted in triplicate at each concentration. 1 μg/ml flag-labeled CD40L (Alexis) and 1 μg/ml CD40L enhancer antibodies (Alexis) were added to each well, followed by 3 days of culturing. Then, 1 μCi [$^3$H] thymidine was added to each well. 12 to 15 hours later, the cells were collected, and then the proliferation of tonsillar B cells was measured using a liquid scintillation counter. The count obtained when B cells had proliferated due to the stimulation of CD40L and no antibody had been added was determined as 100, and the count obtained when no CD40L had been added and B cells had not been not stimulated was determined as 0. For example, when the relative count measured was 30, this was expressed in this experiment as that 70% proliferation inhibition had occurred.

Figure 20:
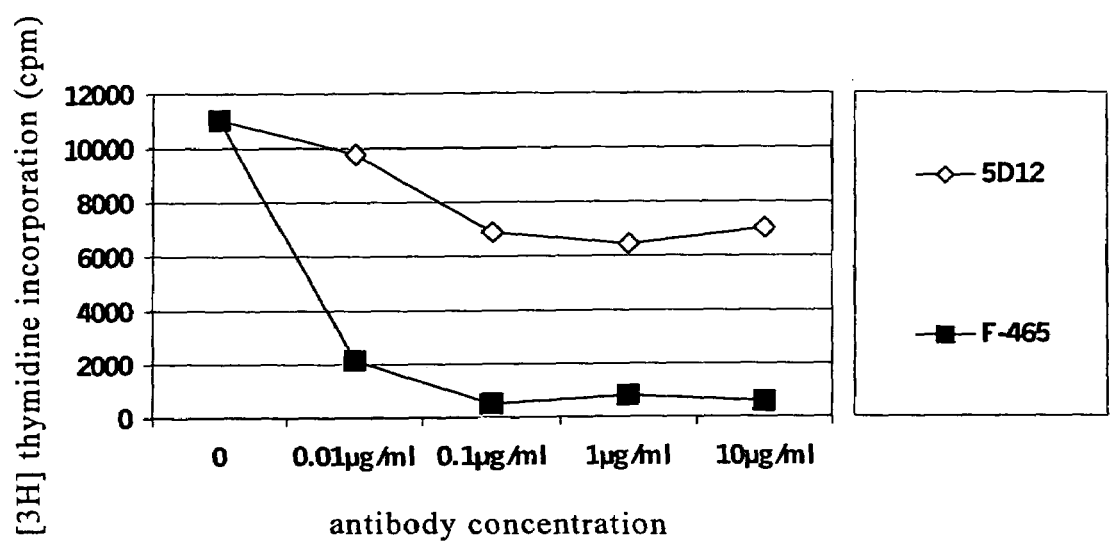
FIG. 20 shows that F4-465 suppressed the proliferation of tonsillar B cells.

5D12, which is the known antagonistic antibody, did not show more than 50% proliferation inhibition even with the antibody concentration of 100 μg/ml. F4-465 showed approximately 80% proliferation suppression even with the antibody concentration as low as 0.01 μg/ml, and showed approximately 95% proliferation suppression with an antibody concentration of 0.1 to 10 μg/ml (FIG. 20).

All publications, patents and patent applications cited herein are incorporated herein by reference in their entirety.

INDUSTRIAL APPLICABILITY

The present invention provides an antibody against CD40. The antibody of the present invention includes both an antibody that acts agonistically on CD40 and an antibody that acts antagonistically on CD40. Thus, these antibodies are useful as, for example, an immunopotentiating agent and immunosuppressive agent, respectively.

Sequence Listing Free Text

SEQ ID NO: 1: Synthetic DNA
SEQ ID NO: 2: Synthetic DNA
SEQ ID NO: 3: Synthetic DNA
SEQ ID NO: 4: Synthetic DNA
SEQ ID NO: 5: Synthetic DNA
SEQ ID NO: 6: Synthetic DNA
SEQ ID NO: 7: Synthetic DNA
SEQ ID NO: 8: Synthetic DNA
SEQ ID NO: 9: Synthetic DNA
SEQ ID NO: 10: Synthetic DNA
SEQ ID NO: 11: Synthetic DNA
SEQ ID NO: 12: Synthetic DNA
SEQ ID NO: 13: Synthetic DNA
SEQ ID NO: 14: Synthetic DNA
SEQ ID NO: 15: Synthetic DNA
SEQ ID NO: 16: Synthetic DNA
SEQ ID NO: 17: Synthetic DNA
SEQ ID NO: 18: Synthetic DNA
SEQ ID NO: 19: Synthetic DNA
SEQ ID NO: 20: Synthetic DNA
SEQ ID NO: 21: Synthetic DNA
SEQ ID NO: 22: Synthetic DNA
SEQ ID NO: 23: Synthetic DNA
SEQ ID NO: 24: Synthetic DNA
SEQ ID NO: 25: Synthetic DNA
SEQ ID NO: 26: Synthetic DNA

The invention claimed is:

1. An isolated antibody or a functional fragment thereof which binds to human CD40, wherein the antibody or the functional fragment thereof has amino acid sequences of a heavy chain variable region and a light chain variable region of the antibody produced by the hybridoma 4D11 (Accession No: FERM BP-7758).

2. An isolated antibody or a functional fragment thereof which binds to human CD40, wherein the antibody or the functional fragment thereof has amino acid sequences of the mature portions of a heavy chain variable region and a light chain variable region of the antibody produced by the hybridoma 4D11 (Accession No: FERM BP-7758), which are respectively represented by SEQ ID NO:48 and SEQ ID NO:50, respectively.

3. An isolated antibody or a functional fragment thereof which binds to human CD40, wherein the antibody or the functional fragment thereof has amino acid sequences of the mature portions of a heavy chain variable region and a light chain variable region of the antibody, which are represented by SEQ ID NO:48 and SEQ ID NO:50, respectively.

4. An isolated antibody or a functional fragment thereof which binds to human CD40, wherein the antibody or the functional fragment thereof has amino acid sequences, which respectively range from the 27th Q residue to the 147th S residue of SEQ ID NO:48 and the 23rd A residue to the 128th K residue of SEQ ID NO:50.

5. An isolated antibody or a functional fragment thereof which binds to an epitope of human CD40 that the antibody produced by the hybridoma 4D11 (Accession No: FERM BP-7758) binds to.

6. The isolated antibody or the functional fragment thereof which binds to human CD40 of any one of claims 1 to 5, which is a human antibody.

7. A pharmaceutical composition, containing as an active ingredient the isolated antibody or the functional fragment thereof which binds to human CD40 of any one of claims 1 to 6.

8. A hybridoma 4D11 (Accession No: FERM BP-7758).

9. An isolated antibody produced by the hybridoma 4D11 (Accession No: FERM BP-7758).

10. An isolated nucleic acid encoding a heavy chain variable region of an antibody isolated from the hybridoma 4D11 (Accession No: FERM BP-7758).

11. The isolated nucleic acid of claim 10, which is RNA or cDNA.

12. An isolated nucleic acid encoding a light chain variable region of an antibody isolated from the hybridoma 4D11 (Accession No: FERM BP-7758).

13. The isolated nucleic acid of claim 12, which is RNA or cDNA.

14. A vector containing the isolated nucleic acid of claims 10 or 12.

15. A host cell containing the vector of claim 14.

16. A method of producing an antibody or a functional fragment thereof which binds to human CD40, comprising culturing the host cell of claim 15 under conditions allowing expression of heavy or light chain variable regions thereby producing the antibody or the functional fragment thereof which binds to human CD40.

17. An isolated antibody or a functional fragment thereof which binds to human CD40, wherein the antibody or the functional fragment thereof has amino acid sequences of the mature portions of a heavy chain variable region and a light chain variable region that are encoded by nucleic acid sequences, which are respectively represented by SEQ ID NO:47 and SEQ ID NO:49.

18. An isolated antibody or a functional fragment thereof which binds to human CD40, wherein the antibody or the functional fragment thereof has amino acid sequences encoded by nucleic acid sequences which respectively range from the $94^{th}$ C to the $456^{th}$ A of SEQ ID NO:47 and from the $125^{th}$ G to the $442^{nd}$ A of SEQ ID NO:49.

19. A method of producing an antibody or a functional fragment thereof which binds to human CD40, comprising culturing a host cell containing nucleic acid that encodes a heavy chain variable region or a light chain variable region of the antibody isolated from the hybridoma 4D11 (Accession No: FERM BP-7758) under conditions allowing expression of heavy or light chain variable region thereby producing the antibody or the functional fragment thereof which binds to human CD40.

20. The isolated antibody or the functional fragment thereof according to claim 1, wherein the functional fragment comprises a heavy chain variable region or a light chain variable region of the antibody produced by the hybridoma 4D11 (Accession No: FERM BP-7758).

21. The isolated antibody or the functional fragment thereof according to claim 2, wherein the functional fragment comprises a mature portion of a heavy chain variable region or a mature portion of a light chain variable region of the antibody, which are respectively represented by SEQ ID NO:48 and SEQ ID NO:50.

* * * * *

SEQUENCE LISTING

```
<160> NUMBER OF SEQ ID NOS: 66

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence:
                        Synthetic DNA

<400> SEQUENCE: 1
cccagatctg tccatccaga accacccact gcatgcagag                           40

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence:
                        Synthetic DNA

<400> SEQUENCE: 2
```

```
acaagatctg ggctctacgt atctcagccg atcctgggga c                    41
```

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 3

```
ggtccgggag atcatgaggg tgtcctt                                    27
```

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 4

```
gtgcacgccg ctggtcaggg cgcctg                                     26
```

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 5

```
gctggagggc acggtcacca cgctg                                      25
```

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 6

```
ggtgccaggg ggaagaccga tgg                                        23
```

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 7

```
atatgtcgac gctgaattct ggctgaccag ggcag                           35
```

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 8

```
atatgtcgac tcccaggtgt ttccattcag tgatcag                         37
```

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 9
atatgtcgac ttccattcgg tgatcagcac tgaacac                          37

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 10
atatgtcgac tttgagagtc ctggacctcc tgtg                             34

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 11
atatgtcgac gagtcatgga tctcatgtgc aag                              33

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 12
atatgtcgac ccagggcagt caccagagct ccagac                           36

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 13
accgtgtcga ctacgcggga gtgact                                      26

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 14
accgtgtcga cgctgatcag gactgcaca                                   29

```
<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 15
accgtgtcga cggtgatcag gactgaacag                                    30

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 16
gttgaagctc tttgtgacgg gcgagc                                        26

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 17
tcttctccac ggtgctccct tcat                                          24

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 18
atatagatct gaactgctca gttaggaccc agagg                              35

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 19
atatagatct cgcggggaag gagactgctc agtt                               34

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 20
atatagatct agtcagaccc agtcaggaca cagc                               34
```

```
<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 21
atatagatct gagctgctca gttaggaccc agaggg                              36

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 22
atatagatct taagcaagtg taacaactca gagtac                              36

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 23
atatagatct gaggaactgc tcagttagga cccagagg                            38

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 24
aactccagat ctgcctcagg aagcagcatc                                     30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 25
aactccagat ctagggcaag cagtggtaac                                     30

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 26
tggcgggaag atgaagacag atggtg                                         26

<210> SEQ ID NO 27
```

<211> LENGTH: 1480
<212> TYPE: DNA
<213> ORGANISM: Homo sapiens

<400> SEQUENCE: 27

```
gtcgacgctg aattctggct gaccagggca gccaccagag ctccagacaa tgtctgtctc      60
cttcctcatc ttcctgcccg tgctgggcct cccatggggt gtcctgtcac aggtccaact     120
gcagcagtca ggtccaggac tggtgaagcc ctcgcagacc ctctcactca cctgtgccat     180
ctccggggac agtgtctcta gcaacagtgc tacttggaac tggatcaggc agtccccatc     240
gagagacctt gagtggctgg aaggacata ctacaggtcc aagtggtatc gtgattatgt      300
aggatctgtg aaaagtcgaa taatcatcaa cccagacaca tccaacaacc agttctccct     360
gcagctgaac tctgtgactc ccgaggacac ggctatatat tactgtacaa gagcacagtg     420
gctgggaggg gattacccct actactacag tatggacgtc tggggccaag ggaccacggt     480
caccgtctct tcagcctcca ccaagggccc atcggtcttc ccctggcgc cctgctccag      540
gagcacctcc gagagcacag cggccctggg ctgcctggtc aaggactact ccccgaacc      600
ggtgacggtg tcgtggaact caggcgctct gaccagcggc gtgcacacct cccagctgt      660
cctacagtcc tcaggactct actccctcag cagcgtggtg accgtgccct ccagcaactt     720
cggcacccag acctacacct gcaacgtaga tcacaagccc agcaacacca aggtggacaa     780
gacagttgag cgcaaatgtt gtgtcgagtg cccaccgtgc ccagcaccac ctgtggcagg     840
accgtcagtc ttcctcttcc ccccaaaacc caaggacacc ctcatgatct cccggacccc     900
tgaggtcacg tgcgtggtgg tggacgtgag ccacgaagac cccgaggtcc agttcaactg     960
gtacgtggac ggcgtggagg tgcataatgc caagacaaag ccacgggagg agcagttcaa    1020
cagcacgttc cgtgtggtca gcgtcctcac cgttgtgcac caggactggc tgaacggcaa    1080
ggagtacaag tgcaaggtct ccaacaaagg cctcccagcc cccatcgaga aaaccatctc    1140
caaaaccaaa gggcagcccc gagaaccaca ggtgtacacc ctgcccccat cccgggagga    1200
gatgaccaag aaccaggtca gcctgacctg cctggtcaaa ggcttctacc ccagcgacat    1260
cgccgtggag tgggagagca atgggcagcc ggagaacaac tacaagacca cctcccat     1320
gctggactca gacggctcct tcttcctcta cagcaagctc accgtggaca gagcaggtg     1380
gcagcagggg aacgtcttct catgctccgt gatgcatgag gctctgcaca accactacac    1440
gcagaagagc ctctccctgt ctccgggtaa atgaggatcc                          1480
```

<210> SEQ ID NO 28
<211> LENGTH: 474
<212> TYPE: PRT
<213> ORGANISM: Homo sapiens

<400> SEQUENCE: 28

```
Met Ser Val Ser Phe Leu Ile Phe Leu Pro Val Leu Gly Leu Pro Trp
  1               5                  10                  15
Gly Val Leu Ser Gln Val Gln Leu Gln Gln Ser Gly Pro Gly Leu Val
                 20                  25                  30
Lys Pro Ser Gln Thr Leu Ser Leu Thr Cys Ala Ile Ser Gly Asp Ser
             35                  40                  45
Val Ser Ser Asn Ser Ala Thr Trp Asn Trp Ile Arg Gln Ser Pro Ser
         50                  55                  60
Arg Asp Leu Glu Trp Leu Gly Arg Thr Tyr Tyr Arg Ser Lys Trp Tyr
 65                  70                  75                  80
```

```
Arg Asp Tyr Val Gly Ser Val Lys Ser Arg Ile Ile Asn Pro Asp
                85                  90                  95

Thr Ser Asn Asn Gln Phe Ser Leu Gln Leu Asn Ser Val Thr Pro Glu
            100                 105                 110

Asp Thr Ala Ile Tyr Tyr Cys Thr Arg Ala Gln Trp Leu Gly Gly Asp
            115                 120                 125

Tyr Pro Tyr Tyr Tyr Ser Met Asp Val Trp Gly Gln Gly Thr Thr Val
            130                 135                 140

Thr Val Ser Ser Ala Ser Thr Lys Gly Pro Ser Val Phe Pro Leu Ala
145                 150                 155                 160

Pro Cys Ser Arg Ser Thr Ser Glu Ser Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
            195                 200                 205

Gly Leu Tyr Ser Leu Ser Ser Val Val Thr Val Pro Ser Ser Asn Phe
            210                 215                 220

Gly Thr Gln Thr Tyr Thr Cys Asn Val Asp His Lys Pro Ser Asn Thr
225                 230                 235                 240

Lys Val Asp Lys Thr Val Glu Arg Lys Cys Cys Val Glu Cys Pro Pro
                245                 250                 255

Cys Pro Ala Pro Pro Val Ala Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Gln Phe Asn Trp
            290                 295                 300

Tyr Val Asp Gly Val Glu Val His Asn Ala Lys Thr Lys Pro Arg Glu
305                 310                 315                 320

Glu Gln Phe Asn Ser Thr Phe Arg Val Val Ser Val Leu Thr Val Val
                325                 330                 335

His Gln Asp Trp Leu Asn Gly Lys Glu Tyr Lys Cys Lys Val Ser Asn
            340                 345                 350

Lys Gly Leu Pro Ala Pro Ile Glu Lys Thr Ile Ser Lys Thr Lys Gly
            355                 360                 365

Gln Pro Arg Glu Pro Gln Val Tyr Thr Leu Pro Pro Ser Arg Glu Glu
            370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Met Leu Asp Ser Asp Gly Ser Phe Phe
            420                 425                 430

Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 29
<211> LENGTH: 406
<212> TYPE: DNA
```

<213> ORGANISM: Homo sapiens

<400> SEQUENCE: 29

```
actgctcagt taggacccag agggaaccat ggaagcccca gctcagcttc tcttcctcct    60
gctactctgg ctcccagata ccaccggaga aattgtgttg acacagtctc cagccaccct   120
gtctttgtct ccaggggaaa gagccaccct ctcctgcagg gccagtcaga gtgttagcag   180
ctacttagcc tggtaccaac agaaacctgg ccaggctccc aggctcctca tctatgatgc   240
atccaacagg gccactggca tcccagccag gttcagtggc agtgggtctg ggacagactt   300
cactctcacc atcagcagcc tagagcctga agattttgca gtttattact gtcagcagcg   360
tagcaacact ttcggccctg ggaccaaagt ggatatcaaa cgtacg                  406
```

<210> SEQ ID NO 30
<211> LENGTH: 126
<212> TYPE: PRT
<213> ORGANISM: Homo sapiens

<400> SEQUENCE: 30

```
Met Glu Ala Pro Ala Gln Leu Leu Phe Leu Leu Leu Leu Trp Leu Pro
  1               5                  10                  15
Asp Thr Thr Gly Glu Ile Val Leu Thr Gln Ser Pro Ala Thr Leu Ser
             20                  25                  30
Leu Ser Pro Gly Glu Arg Ala Thr Leu Ser Cys Arg Ala Ser Gln Ser
         35                  40                  45
Val Ser Ser Tyr Leu Ala Trp Tyr Gln Gln Lys Pro Gly Gln Ala Pro
     50                  55                  60
Arg Leu Leu Ile Tyr Asp Ala Ser Asn Arg Ala Thr Gly Ile Pro Ala
 65                  70                  75                  80
Arg Phe Ser Gly Ser Gly Ser Gly Thr Asp Phe Thr Leu Thr Ile Ser
                 85                  90                  95
Ser Leu Glu Pro Glu Asp Phe Ala Val Tyr Tyr Cys Gln Gln Arg Ser
            100                 105                 110
Asn Thr Phe Gly Pro Gly Thr Lys Val Asp Ile Lys Arg Thr
        115                 120                 125
```

<210> SEQ ID NO 31
<211> LENGTH: 508
<212> TYPE: DNA
<213> ORGANISM: Homo sapiens

<400> SEQUENCE: 31

```
ctgaacacag acccgtcgac tcccaggtgt ttccattcag tgatcagcac tgaacacaga    60
ggactcacca tggagtttgg gactgagctg gattttcctt tggctatttt aaaaggtgtc   120
cagtgtgaag tgcagctggt ggagtctggg ggaggcttgg tacagcctgg caggtccctg   180
agactctcct gtgcagcctc tggattcacc tttgatgatt atgccatgca ctgggtccgg   240
caagctccag ggaagggcct ggagtgggtc tcaggtatta gttggaatag tggtagcttg   300
gtgcatgcga ctctgtgaa gggccgattc accatctcca gagacaacgc caagaactcc   360
ctgtatctgc aaatgaacag tctgagagct gaggacacgg ccttgtatta ctgtgcaaga   420
gataggctat tcggggagt taggtactac ggtatggacg tctggggcca agggaccacg   480
gtcaccgtct cctcagctag caccaagg                                     508
```

<210> SEQ ID NO 32
<211> LENGTH: 146

<212> TYPE: PRT
<213> ORGANISM: Homo sapiens

<400> SEQUENCE: 32

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Gly Ile Ser Trp Asn Ser Gly Ser Leu Val His Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Arg Asp Arg Leu Phe Arg Gly Val Arg Tyr Tyr Gly
        115                 120                 125

Met Asp Val Trp Gly Gln Gly Thr Thr Val Thr Val Ser Ser Ala Ser
    130                 135                 140

Thr Lys
145

<210> SEQ ID NO 33
<211> LENGTH: 414
<212> TYPE: DNA
<213> ORGANISM: Homo sapiens

<400> SEQUENCE: 33
ctgctcagtt aggacccaga gggaaccatg gaagcccag ctcagcttct cttcctcctg      60
ctactctggc tcccagatac caccggagaa attgtgttga cagtctcc agccaccctg     120 tctttgtctc caggggaaag agccaccctc tcctgcaggg ccagtcagag tgttagcagc     180
tacttagcct ggtaccaaca gaaacctggc caggctccca ggctcctcat ctatgatgca     240
tccaacaggg ccactggcat cccagccagg ttcagtggca gtgggtctgg gacagacttc     300
actctcacca tcagcagcct agagcctgaa gattttgcag tttattactg tcagcagcgt     360
agccactggc tcactttcgg cggggggacc aaggtggaga tcaaacgtac ggtg          414

<210> SEQ ID NO 34
<211> LENGTH: 129
<212> TYPE: PRT
<213> ORGANISM: Homo sapiens

<400> SEQUENCE: 34

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

```
Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

His Trp Leu Thr Phe Gly Gly Gly Thr Lys Val Glu Ile Lys Arg Thr
        115                 120                 125

Val
```

<210> SEQ ID NO 35
<211> LENGTH: 493
<212> TYPE: DNA
<213> ORGANISM: Homo sapiens

<400> SEQUENCE: 35

```
ctgaacacag acccgtcgac ttccattcgg tgatcagcac tgaacacaga ggactcacca      60
tggagtttgg gctgagctgg gttttcctcg ttgctctttt aagaggtgtc cagtgtcagg     120
tgcagctggt ggagtctggg ggaggcgtgg tccagcctgg gaggtccctg agactctcct     180
gtgcagcgtc tggattcacc ttcagtagct atggcatgca ctgggtccgc caggctccag     240
gcaaggggct ggagtgggtg gcagttatat ggtatgatgg aagtattaaa tactatgcag     300
actccgtgaa gggccgattc accatctcca gagacaattc caagaacacg ctgtatctgc     360
aaatgaacag cctgagagcc gaggacacgg ctgtgtatta ctgtgcgaga gagggctaca     420
atattttgac tggttatttt ggctactggg gccagggaac cctggtcacc gtctcctcag     480
ctagcaccaa ggg                                                       493
```

<210> SEQ ID NO 36
<211> LENGTH: 144
<212> TYPE: PRT
<213> ORGANISM: Homo sapiens

<400> SEQUENCE: 36

```
Met Glu Phe Gly Leu Ser Trp Val Phe Leu Val Ala Leu Leu Arg Gly
  1               5                  10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Asp Gly Ser Ile Lys Tyr Tyr Ala
 65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Glu Gly Tyr Asn Ile Leu Thr Gly Tyr Phe Gly
        115                 120                 125

Tyr Trp Gly Gln Gly Thr Leu Val Thr Val Ser Ser Ala Ser Thr Lys
    130                 135                 140
```

<210> SEQ ID NO 37
<211> LENGTH: 427
<212> TYPE: DNA
<213> ORGANISM: Homo sapiens -continued

```
<400> SEQUENCE: 37
tcacagatct agtcagaccc agtcaggaca cagcatggac atgagggtcc ccgctcagct        60
cctggggctc ctgctgctct ggctcccagg tgccagatgt gtcatctgga tgacccagtc       120
tccatcctta ctctctgcat ctacaggaga cagagtcacc atcagttgtc ggatgagtca       180
gggcattagc agtgatttag cctggtatca gcaaaaacca gggaaagccc ctgagctcct       240
gatctctgct gcatccactt tgcaaagtgg ggtcccatca aggttcagtg gcagtggatc       300
tgggacagat ttcactctca ccatcagctg cctgcagtct gaagattttg caacttatta       360
ctgtcaacag tattatagtt ttccgtggac gttcggccaa gggaccaagg tggaaatcaa       420
acgtacg                                                                 427

<210> SEQ ID NO 38
<211> LENGTH: 131
<212> TYPE: PRT
<213> ORGANISM: Homo sapiens

<400> SEQUENCE: 38

Met Asp Met Arg Val Pro Ala Gln Leu Leu Gly Leu Leu Leu Leu Trp
 1               5                  10                  15

Leu Pro Gly Ala Arg Cys Val Ile Trp Met Thr Gln Ser Pro Ser Leu
             20                  25                  30

Leu Ser Ala Ser Thr Gly Asp Arg Val Thr Ile Ser Cys Arg Met Ser
         35                  40                  45

Gln Gly Ile Ser Ser Asp Leu Ala Trp Tyr Gln Lys Pro Gly Lys
     50                  55                  60

Ala Pro Glu Leu Leu Ile Ser Ala Ala Ser Thr Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Cys Leu Gln Ser Glu Asp Phe Ala Thr Tyr Tyr Cys Gln Gln
            100                 105                 110

Tyr Tyr Ser Phe Pro Trp Thr Phe Gly Gln Gly Thr Lys Val Glu Ile
        115                 120                 125

Lys Arg Thr
    130

<210> SEQ ID NO 39
<211> LENGTH: 492
<212> TYPE: DNA
<213> ORGANISM: Homo sapiens

<400> SEQUENCE: 39
ctgaacacag acccgtcgac ttccattcgg tgatcagcac tgaacacaga ggactcacca        60
tggagtttgg gctgagctgg gttttcctcg ttgctctttt aagaggtgtc cagtgtcagg       120
tgcagctggt ggagtctggg ggaggcgtgg tccagcctgg gaggtccctg agactctcct       180
gtgcagcgtc tggattcacc ttcagtagct atggcatgca ctgggtccgc caggctccag       240
gcaaggggct ggagtgggtg gcagttatat ggaatgatgg aagtattaaa tactatgcag       300
actccgtgaa gggccgattc accatctcca gagacaattc caagaacacg ctgtatctgc       360
aaatgaacag cctgagagcc gaggacacgg ctgtgtatta ctgtgcgaga gagggctaca       420
atattttgac tggttatttt ggctactggg gccagggaac cctggtcacc gtctcctcag       480
ctagcaccaa gg                                                           492
```

<210> SEQ ID NO 40
<211> LENGTH: 144
<212> TYPE: PRT
<213> ORGANISM: Homo sapiens

<400> SEQUENCE: 40

```
Met Glu Phe Gly Leu Ser Trp Val Phe Leu Val Ala Leu Leu Arg Gly
  1               5                  10                  15

Val Gln Cys Gln Val Gln Leu Val Glu Ser Gly Gly Val Val Gln
             20                  25                  30

Pro Gly Arg Ser Leu Arg Leu Ser Cys Ala Ala Ser Gly Phe Thr Phe
             35                  40                  45

Ser Ser Tyr Gly Met His Trp Val Arg Gln Ala Pro Gly Lys Gly Leu
     50                  55                  60

Glu Trp Val Ala Val Ile Trp Asn Asp Gly Ser Ile Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Glu Gly Tyr Asn Ile Leu Thr Gly Tyr Phe Gly
            115                 120                 125

Tyr Trp Gly Gln Gly Thr Leu Val Thr Val Ser Ser Ala Ser Thr Lys
        130                 135                 140
```

<210> SEQ ID NO 41
<211> LENGTH: 427
<212> TYPE: DNA
<213> ORGANISM: Homo sapiens

<400> SEQUENCE: 41

```
tcacagatct agtcagaccc agtcaggaca cagcatggac atgagggtcc ccgctcagct    60
cctggggctc ctgctgctct ggctcccagg tgccagatgt gtcatctgga tgacccagtc   120
tccatcctta ctctctgcat ctacaggaga cagagtcacc atcagttgtc ggatgagtca   180
gggcattagc agtgatttag cctggtatca gcaaaaacca gggaaagccc tgagctcct    240 gatctctgct gcatccactt tgcaaagtgg ggtcccatca aggttcagtg cagtggatc    300 tgggacagat ttcactctca ccatcagctg cctgcagtct gaagattttg caacttatta   360
ctgtcaacag tattatagtt ttccgtggac gttcggccaa gggaccaagg tggaaatcaa   420
acgtacg                                                            427
```

<210> SEQ ID NO 42
<211> LENGTH: 131
<212> TYPE: PRT
<213> ORGANISM: Homo sapiens

<400> SEQUENCE: 42

```
Met Asp Met Arg Val Pro Ala Gln Leu Leu Gly Leu Leu Leu Leu Trp
  1               5                  10                  15

Leu Pro Gly Ala Arg Cys Val Ile Trp Met Thr Gln Ser Pro Ser Leu
             20                  25                  30

Leu Ser Ala Ser Thr Gly Asp Arg Val Thr Ile Ser Cys Arg Met Ser
         35                  40                  45

Gln Gly Ile Ser Ser Asp Leu Ala Trp Tyr Gln Gln Lys Pro Gly Lys
     50                  55                  60
```

Ala Pro Glu Leu Leu Ile Ser Ala Ala Ser Thr Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Cys Leu Gln Ser Glu Asp Phe Ala Thr Tyr Tyr Cys Gln Gln
            100                 105                 110

Tyr Tyr Ser Phe Pro Trp Thr Phe Gly Gln Gly Thr Lys Val Glu Ile
        115                 120                 125

Lys Arg Thr
    130

<210> SEQ ID NO 43
<211> LENGTH: 481
<212> TYPE: DNA
<213> ORGANISM: Homo sapiens

<400> SEQUENCE: 43
ctgaacacag acccgtcgac tttgagagtc ctggacctcc tgtgcaagaa catgaaacat      60
ctgtggttct tccttctcct ggtggcagct cccagatggg tcctgtccca ggtgcagctg     120
caggagtcgg gcccaggact ggtgaagcct tcggagaccc tgtccctcac ctgcactgtc     180
tctggtggct ccatcagtgg ttactactgg agctggatcc ggcagccccc agggaaggga     240
ctggagtgga ttgggtatat ctattacagt gggagcacca actacaatcc ctccctcaag     300
agtcgagtca ccatatcagt agacacgtcc aagaaccagt tctccctgaa gctgaattct     360
gtgaccgctg cggacacggc cgtgtattac tgtgcgagag ccccttgca cggtgactac      420
aaatggttcc accctgggg ccagggaacc ctggtcaccg tctcctcagc tagcaccaag      480
g                                                                    481

<210> SEQ ID NO 44
<211> LENGTH: 143
<212> TYPE: PRT
<213> ORGANISM: Homo sapiens

<400> SEQUENCE: 44

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Gly Tyr Tyr Trp Ser Trp Ile Arg Gln Pro Pro Gly Lys Gly Leu
    50                  55                  60

Glu Trp Ile Gly Tyr Ile Tyr Tyr Ser Gly Ser Thr Asn Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Asn Ser Val Thr Ala Ala Asp Thr Ala Val Tyr
            100                 105                 110

Tyr Cys Ala Arg Ala Pro Leu His Gly Asp Tyr Lys Trp Phe His Pro
        115                 120                 125

Trp Gly Gln Gly Thr Leu Val Thr Val Ser Ser Ala Ser Thr Lys
    130                 135                 140

<210> SEQ ID NO 45
<211> LENGTH: 430

-continued

```
<212> TYPE: DNA
<213> ORGANISM: Homo sapiens

<400> SEQUENCE: 45
tcacagatct gagctgctca gttaggaccc agagggaacc atggaaaccc cagcgcagct      60
tctcttcctc ctgctactct ggctcccaga taccaccgga gaaattgtgt tgacgcagtc     120
tccaggcacc ctgtctttgt ctccagggga agagccacc ctctcctgca gggccagtca     180
gagtgttagc agcagctact tagcctggta ccagcagaaa cctggccagg ctcccaggct     240
cctcatctat ggtgcatcca gcagggccac tggcatccca gacaggttca gtggcagtgg     300
gtctgggaca gacttcactc tcaccatcag cagactggag cctgaagatt ttgcagtgta     360
ttactgtcag cagtatggta gctcaccgat caccttcggc caagggacac gactggagat     420
caaacgtacg                                                             430

<210> SEQ ID NO 46
<211> LENGTH: 130
<212> TYPE: PRT
<213> ORGANISM: Homo sapiens

<400> SEQUENCE: 46

Met Glu Thr Pro Ala Gln Leu Leu Phe Leu Leu Leu Trp Leu Pro
  1               5                  10                  15

Asp Thr Thr Gly Glu Ile Val Leu Thr Gln Ser Pro Gly Thr Leu Ser
                 20                  25                  30

Leu Ser Pro Gly Glu Arg Ala Thr Leu Ser Cys Arg Ala Ser Gln Ser
            35                  40                  45

Val Ser Ser Ser Tyr Leu Ala Trp Tyr Gln Gln Lys Pro Gly Gln Ala
        50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                     85                  90                  95

Ser Arg Leu Glu Pro Glu Asp Phe Ala Val Tyr Tyr Cys Gln Gln Tyr
                100                 105                 110

Gly Ser Ser Pro Ile Thr Phe Gly Gln Gly Thr Arg Leu Glu Ile Lys
            115                 120                 125

Arg Thr
    130

<210> SEQ ID NO 47
<211> LENGTH: 462
<212> TYPE: DNA
<213> ORGANISM: Homo sapiens

<400> SEQUENCE: 47
atatgtcgac gagtcatgga tctcatgtgc aagaaaatga agcacctgtg gttcttcctc      60
ctgctggtgg cggctcccag atgggtcctg tcccagctgc agctgcagga gtcgggccca     120
ggactactga agccttcgga gaccctgtcc ctcacctgca ctgtctctgg cggctccatc     180
agcagtcctg gttactacgg gggctggatc cgccagcccc cagggaaggg gctggagtgg     240
attgggagta tctataaaag tgggagcacc taccacaacc cgtccctcaa gagtcgagtc     300
accatatccg tagacacgtc caagaaccag ttctccctga agctgagctc tgtgaccgcc     360
gcagacacgg ctgtgtatta ctgtacgaga cctgtagtac gatattttgg gtggttcgac     420
ccctggggcc agggaaccct ggtcaccgtc tcctcagcta gc                        462
```

<210> SEQ ID NO 48
<211> LENGTH: 149
<212> TYPE: PRT
<213> ORGANISM: Homo sapiens

<400> SEQUENCE: 48

Met Asp Leu Met Cys Lys Lys Met Lys His Leu Trp Phe Phe Leu Leu
1               5                   10                  15

Leu Val Ala Ala Pro Arg Trp Val Leu Ser Gln Leu Gln Leu Gln Glu
                20                  25                  30

Ser Gly Pro Gly Leu Leu Lys Pro Ser Glu Thr Leu Ser Leu Thr Cys
            35                  40                  45

Thr Val Ser Gly Gly Ser Ile Ser Ser Pro Gly Tyr Tyr Gly Gly Trp
        50                  55                  60

Ile Arg Gln Pro Pro Gly Lys Gly Leu Glu Trp Ile Gly Ser Ile Tyr
65                  70                  75                  80

Lys Ser Gly Ser Thr Tyr His Asn Pro Ser Leu Lys Ser Arg Val Thr
                85                  90                  95

Ile Ser Val Asp Thr Ser Lys Asn Gln Phe Ser Leu Lys Leu Ser Ser
                100                 105                 110

Val Thr Ala Ala Asp Thr Ala Val Tyr Tyr Cys Thr Arg Pro Val Val
            115                 120                 125

Arg Tyr Phe Gly Trp Phe Asp Pro Trp Gly Gln Gly Thr Leu Val Thr
        130                 135                 140

Val Ser Ser Ala Ser
145

<210> SEQ ID NO 49
<211> LENGTH: 448
<212> TYPE: DNA
<213> ORGANISM: Homo sapiens

<400> SEQUENCE: 49
agatcttaag caagtgtaac aactcagagt acgcggggag acccactcag gacacagcat        60
ggacatgagg gtccccgctc agctcctggg gcttctgctg ctctggctcc caggtgccag       120
atgtgccatc cagttgaccc agtctccatc ctccctgtct gcatctgtag gagacagagt       180
caccatcact tgccgggcaa gtcagggcat tagcagtgct ttagcctggt atcagcagaa       240
accagggaaa gctcctaagc tcctgatcta tgatgcctcc aatttggaaa gtggggtccc       300
atcaaggttc agcggcagtg gatctgggac agatttcact ctcaccatca gcagcctgca       360
gcctgaagat tttgcaactt attactgtca acagtttaat agttacccga cgttcggcca       420
agggaccaag gtggaaatca aacgtacg                                         448

<210> SEQ ID NO 50
<211> LENGTH: 130
<212> TYPE: PRT
<213> ORGANISM: Homo sapiens

<400> SEQUENCE: 50

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
                20                  25                  30

Leu Ser Ala Ser Val Gly Asp Arg Val Thr Ile Thr Cys Arg Ala Ser
            35                  40                  45

```
Gln Gly Ile Ser Ser Ala Leu Ala Trp Tyr Gln Gln Lys Pro Gly Lys
        50                  55                  60

Ala Pro Lys Leu Leu Ile Tyr Asp Ala Ser Asn Leu Glu Ser Gly Val
 65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Thr Phe Gly Gln Gly Thr Lys Val Glu Ile Lys
        115                 120                 125

Arg Thr
    130

<210> SEQ ID NO 51
<211> LENGTH: 453
<212> TYPE: DNA
<213> ORGANISM: Homo sapiens

<400> SEQUENCE: 51
atgtctgtct ccttcctcat cttcctgccc gtgctgggcc tcccatgggg tgtcctgtca      60
caggtacagc tgcagcagtc aggtccagga ctggtgaagc cctcgcagac cctctcattc     120
acctgtgcca tctccgggga cagtgtctct agcaacagtg ctgcttggaa ctggatcagg     180
cagtccccat cgagaggcct tgagtggctg ggaaggacat actacaggtc aagtggtat     240 aaagattatg cagtatctgt gaaaagtcga ataaccatca cccagacac atccaagaac     300 cagttctccc tgcagctgaa ctctgtgacc cccgaggaca cggctgtgta ttactgtgca     360
agagggtatt actatggttc ggggagctat ccctactact accaaatgga cgtctggggc     420
caagggacca cggtcaccgt ctcctcagct agc                                  453

<210> SEQ ID NO 52
<211> LENGTH: 151
<212> TYPE: PRT
<213> ORGANISM: Homo sapiens

<400> SEQUENCE: 52

Met Ser Val Ser Phe Leu Ile Phe Leu Pro Val Leu Gly Leu Pro Trp
  1               5                  10                  15

Gly Val Leu Ser Gln Val Gln Leu Gln Gln Ser Gly Pro Gly Leu Val
                20                  25                  30

Lys Pro Ser Gln Thr Leu Ser Phe Thr Cys Ala Ile Ser Gly Asp Ser
            35                  40                  45

Val Ser Ser Asn Ser Ala Ala Trp Asn Trp Ile Arg Gln Ser Pro Ser
 50                  55                  60

Arg Gly Leu Glu Trp Leu Gly Arg Thr Tyr Tyr Arg Ser Lys Trp Tyr
 65                  70                  75                  80

Lys Asp Tyr Ala Val Ser Val Lys Ser Arg Ile Thr Ile Asn Pro Asp
                85                  90                  95

Thr Ser Lys Asn Gln Phe Ser Leu Gln Leu Asn Ser Val Thr Pro Glu
            100                 105                 110

Asp Thr Ala Val Tyr Tyr Cys Ala Arg Gly Tyr Tyr Tyr Gly Ser Gly
        115                 120                 125

Ser Tyr Pro Tyr Tyr Tyr Gln Met Asp Val Trp Gly Gln Gly Thr Thr
    130                 135                 140

Val Thr Val Ser Ser Ala Ser
```

-continued

```
145                 150

<210> SEQ ID NO 53
<211> LENGTH: 414
<212> TYPE: DNA
<213> ORGANISM: Homo sapiens

<400> SEQUENCE: 53
aattgaggaa ctgctcagtt aggacccaga gggaaccatg gaagcccag ctcagcttct      60 cttcctcctg ctactctggc tcccagatac caccggagaa attgtgttga cacagtctcc    120
agccaccctg tctttgtctc aggggaaag tgccaccctc tcctgcaggg ccagtcagag     180
tgttagcagc tacttagcct ggtaccaaca gaaacctggc caggctccca ggctcctcat    240
ctatgatgca tccaacaggg ccactggcat cccagccagg ttcagtggca gtgggtctgg    300
gacagacttc actctcacca tcagcagcct agagcctgaa gattttgcag tttattactg    360
tcagcagcgt agcaacactt tcggcggagg gaccaaggtg gagatcaaac gaac          414

<210> SEQ ID NO 54
<211> LENGTH: 125
<212> TYPE: PRT
<213> ORGANISM: Homo sapiens

<400> SEQUENCE: 54

Met Glu Ala Pro Ala Gln Leu Leu Phe Leu Leu Leu Leu Trp Leu Pro
 1               5                  10                  15

Asp Thr Thr Gly Glu Ile Val Leu Thr Gln Ser Pro Ala Thr Leu Ser
            20                  25                  30

Leu Ser Pro Gly Glu Ser Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Thr Phe Gly Gly Gly Thr Lys Val Glu Ile Lys Arg
        115                 120                 125

<210> SEQ ID NO 55
<211> LENGTH: 495
<212> TYPE: DNA
<213> ORGANISM: Homo sapiens

<400> SEQUENCE: 55
ctgaacacag acccgtcgac tacgcgggag accacagctc cacaccatgg actggacctg     60
gaggatccta ttcttggtgg cagcagcaac aggtgcccac tcccaggtgc agctggtgca    120
atctgggtct gagttgaaga agcctggggc ctcagtgaag gtcccctgca aggcttctgg    180
atacaccttc actagctatg ctatgaattg ggtgcgacag gcccctggac aagggcttga    240
gtggatggga tggatcaaca ccaacactgg gaacccaacg tatgcccagg gcttcacagg    300
acggtttgtc ttctccttgg acacctctgt cagcacggca tatctgcaga tcagcagcct    360
aaaggctgag gacactgccg tgtattactg tgcgagagag gtagtaccag ttgctatgag    420
ggtaactcac tactactacg gtatggacgt ctggggccaa gggaccacgg tcaccgtctc    480
```
ctcagctagc accaa                                                        495

<210> SEQ ID NO 56
<211> LENGTH: 149
<212> TYPE: PRT
<213> ORGANISM: Homo sapiens

<400> SEQUENCE: 56

Met Asp Trp Thr Trp Arg Ile Leu Phe Leu Val Ala Ala Ala Thr Gly
 1               5                  10                  15

Ala His Ser Gln Val Gln Leu Val Gln Ser Gly Ser Glu Leu Lys Lys
            20                  25                  30

Pro Gly Ala Ser Val Lys Val Pro Cys Lys Ala Ser Gly Tyr Thr Phe
        35                  40                  45

Thr Ser Tyr Ala Met Asn Trp Val Arg Gln Ala Pro Gly Gln Gly Leu
    50                  55                  60

Glu Trp Met Gly Trp Ile Asn Thr Asn Thr Gly Asn Pro Thr Tyr Ala
 65                  70                  75                  80

Gln Gly Phe Thr Gly Arg Phe Val Phe Ser Leu Asp Thr Ser Val Ser
                85                  90                  95

Thr Ala Tyr Leu Gln Ile Ser Ser Leu Lys Ala Glu Asp Thr Ala Val
            100                 105                 110

Tyr Tyr Cys Ala Arg Glu Val Val Pro Val Ala Met Arg Val Thr His
        115                 120                 125

Tyr Tyr Tyr Gly Met Asp Val Trp Gly Gln Gly Thr Thr Val Thr Val
    130                 135                 140

Ser Ser Ala Ser Thr
145

<210> SEQ ID NO 57
<211> LENGTH: 830
<212> TYPE: DNA
<213> ORGANISM: Homo sapiens

<400> SEQUENCE: 57
ctgggtacgg taaccgtcag atcgcctgga gacgccatca cagatctgcc tcaggaagca      60
gcatcggagg tgcctcagcc atggcatgga tccctctctt cctcggcgtc cttgtttact    120
gcacaggatc cgtggcctcc tatgagctga ctcagccacc ctcagtgtcc gtggccccag    180
gacagacagc cagcatcacc tgttctggag ataaattggg ggataatttt acttgctggt    240
atcagcagaa gccaggccag tcccctgtgc tggtcatctt tcaggattgg aagcggcgcc    300
cagggatccc tgcgcgattc tctggctcca gtctgggaa cacagccact ctgaccatca    360
gcgggaccca ggctatggat gaggctgact attactgtca ggcgtgggac atcagcactg    420
tggtattcgg cggagggacc aagctgaccg tcctaggtca gcccaaggct gccccctcgg    480
tcactctgtt cccgccctcc tctgaggagc ttcaagccaa caaggccaca ctggtgtgtc    540
tcataagtga cttctacccg ggagccgtga cagtggcctg gaaggcagat agcagccccg    600
tcaaggcggg agtggagacc accacaccct ccaaacaaag caacaacaag tacgcggcca    660
gcagctacct gagcctgacg cctgagcagt ggaagtccca cagaagctac agctgccagg    720
tcacgcatga agggagcacc gtggagaaga cagtggcccc tacagaatgt tcatgaattc    780
agatccgtta acggttacca actacctaga ctggattcgt gaccaacata                830

<210> SEQ ID NO 58

<211> LENGTH: 231
<212> TYPE: PRT
<213> ORGANISM: Homo sapiens

<400> SEQUENCE: 58

```
Met Ala Trp Ile Pro Leu Phe Leu Gly Val Leu Val Tyr Cys Thr Gly
  1               5                  10                  15

Ser Val Ala Ser Tyr Glu Leu Thr Gln Pro Pro Ser Val Ser Val Ala
             20                  25                  30

Pro Gly Gln Thr Ala Ser Ile Thr Cys Ser Gly Asp Lys Leu Gly Asp
         35                  40                  45

Asn Phe Thr Cys Trp Tyr Gln Gln Lys Pro Gly Gln Ser Pro Val Leu
 50                  55                  60

Val Ile Phe Gln Asp Trp Lys Arg Arg Pro Gly Ile Pro Ala Arg Phe
 65                  70                  75                  80

Ser Gly Ser Lys Ser Gly Asn Thr Ala Thr Leu Thr Ile Ser Gly Thr
                 85                  90                  95

Gln Ala Met Asp Glu Ala Asp Tyr Tyr Cys Gln Ala Trp Asp Ile Ser
            100                 105                 110

Thr Val Val Phe Gly Gly Gly Thr Lys Leu Thr Val Leu Gly Gln Pro
            115                 120                 125

Lys Ala Ala Pro Ser Val Thr Leu Phe Pro Pro Ser Ser Glu Glu Leu
130                 135                 140

Gln Ala Asn Lys Ala Thr Leu Val Cys Leu Ile Ser Asp Phe Tyr Pro
145                 150                 155                 160

Gly Ala Val Thr Val Ala Trp Lys Ala Asp Ser Ser Pro Val Lys Ala
                165                 170                 175

Gly Val Glu Thr Thr Pro Ser Lys Gln Ser Asn Asn Lys Tyr Ala
            180                 185                 190

Ala Ser Ser Tyr Leu Ser Leu Thr Pro Glu Gln Trp Lys Ser His Arg
        195                 200                 205

Ser Tyr Ser Cys Gln Val Thr His Glu Gly Ser Thr Val Glu Lys Thr
210                 215                 220

Val Ala Pro Thr Glu Cys Ser
225                 230
```

<210> SEQ ID NO 59
<211> LENGTH: 520
<212> TYPE: DNA
<213> ORGANISM: Homo sapiens

<400> SEQUENCE: 59

```
gctgatcagg actgcacaca gagaactcac catggagttt gggctgagct gggttttcct    60
tgttgctatt ttaaaaggtg tccagtgtga ggtgcagctg gtggagtccg ggggaggctt   120
agttcagcct ggggggtccc tgagactctc ctgtgcagtc tctggattca ccttcagtac   180
ctactggatg cactgggtcc gccaagctcc agggaagggg ctggtgtggg tctcacgtat   240
taatagtgat gggagtagca caacctacgc ggactccgtg aagggccgat tcaccatctc   300
cagagacaac gccaagaaca cgctgtatct gcaaatgaac agtctgagag ccgaggacac   360
ggctgtgtat tactgtgcaa agatagagt actatggatc ggggagttat cctactacgg   420
tatggacgtc tggggccaag gaccacggt caccgtctcc tcagctagca ccaagggccc   480
atcggtcttc cccctggcac cctcctccaa gagcacctct                         520
```

<210> SEQ ID NO 60

<211> LENGTH: 163
<212> TYPE: PRT
<213> ORGANISM: Homo sapiens

<400> SEQUENCE: 60

```
Met Glu Phe Gly Leu Ser Trp Val Phe Leu Val Ala Ile Leu Lys Gly
  1               5                  10                  15
Val Gln Cys Glu Val Gln Leu Val Glu Ser Gly Gly Gly Leu Val Gln
             20                  25                  30
Pro Gly Gly Ser Leu Arg Leu Ser Cys Ala Val Ser Gly Phe Thr Phe
         35                  40                  45
Ser Thr Tyr Trp Met His Trp Val Arg Gln Ala Pro Gly Lys Gly Leu
     50                  55                  60
Val Trp Val Ser Arg Ile Asn Ser Asp Gly Ser Ser Thr Thr Tyr Ala
 65                  70                  75                  80
Asp Ser Val Lys Gly Arg Phe Thr Ile Ser Arg Asp Asn Ala Lys Asn
                 85                  90                  95
Thr Leu Tyr Leu Gln Met Asn Ser Leu Arg Ala Glu Asp Thr Ala Val
            100                 105                 110
Tyr Tyr Cys Ala Arg Asp Arg Val Leu Trp Ile Gly Glu Leu Ser Tyr
        115                 120                 125
Tyr Gly Met Asp Val Trp Gly Gln Gly Thr Thr Val Thr Val Ser Ser
    130                 135                 140
Ala Ser Thr Lys Gly Pro Ser Val Phe Pro Leu Ala Pro Ser Ser Lys
145                 150                 155                 160
Ser Thr Ser
```

<210> SEQ ID NO 61
<211> LENGTH: 698
<212> TYPE: DNA
<213> ORGANISM: Homo sapiens

<400> SEQUENCE: 61

```
gggagtcag acccagtcag gacacagcat ggacatgagg gtccccgctc agctcctggg    60
gctcctgctg ctctggctcc caggtgccaa atgtgacatc cagatgaccc agtctccttc   120
caccctgtct gcatctgtag gagacagagt caccatcact tgccgggcca gtcagagtat   180
tagtaactgg ttggcctggt atcagcagaa accagggaaa gcccctaagc tcctgctcta   240
taaggcatct ggtttagaaa gtggggtccc atcaaggttc agcggcagtg gatctgggac   300
agaattcact ctcaccatca acagcctgca gcctgatgat tttgcaactt attactgcca   360
acagtctaat agttattcgt ggacgttcgg ccacgggacc aaggtggaaa tcaaacgtac   420
ggtggctgca ccatctgtct tcatcttccc gccatctgat gagcagttga aatctggaac   480
tgcctctgtt gtgtgcctgc tgaataactt ctatcccaga gaggccaaag tacagtggaa   540
ggtggataac gccctccaat cgggtaactc ccaggagagt gtcacagagc aggacagcaa   600
ggacagcacc tacagcctca gcagcaccct gacgctgagc aaagcagact acgagaaaca   660
caaagtctac gcctgcgaag tcacccatca gggcctga                          698
```

<210> SEQ ID NO 62
<211> LENGTH: 223
<212> TYPE: PRT
<213> ORGANISM: Homo sapiens

<400> SEQUENCE: 62

Met Asp Met Arg Val Pro Ala Gln Leu Leu Gly Leu Leu Leu Leu Trp

|   1 |   |   |   |   5 |   |   |   |   | 10  |   |   |   |   | 15  |   |
|---|---|---|---|---|---|---|---|---|---|---|---|---|---|---|---|
| Leu | Pro | Gly | Ala | Lys | Cys | Asp | Ile | Gln | Met | Thr | Gln | Ser | Pro | Ser | Thr |
|   |   |   | 20 |   |   |   |   | 25 |   |   |   |   | 30 |   |   |
| Leu | Ser | Ala | Ser | Val | Gly | Asp | Arg | Val | Thr | Ile | Thr | Cys | Arg | Ala | Ser |
|   |   | 35 |   |   |   |   | 40 |   |   |   |   | 45 |   |   |   |
| Gln | Ser | Ile | Ser | Asn | Trp | Leu | Ala | Trp | Tyr | Gln | Gln | Lys | Pro | Gly | Lys |
|   | 50 |   |   |   |   | 55 |   |   |   |   | 60 |   |   |   |   |
| Ala | Pro | Lys | Leu | Leu | Leu | Tyr | Lys | Ala | Ser | Gly | Leu | Glu | Ser | Gly | Val |
| 65 |   |   |   |   | 70 |   |   |   |   | 75 |   |   |   |   | 80 |
| Pro | Ser | Arg | Phe | Ser | Gly | Ser | Gly | Ser | Gly | Thr | Glu | Phe | Thr | Leu | Thr |
|   |   |   |   | 85 |   |   |   |   | 90 |   |   |   |   | 95 |   |
| Ile | Asn | Ser | Leu | Gln | Pro | Asp | Asp | Phe | Ala | Thr | Tyr | Tyr | Cys | Gln | Gln |
|   |   |   | 100 |   |   |   |   | 105 |   |   |   |   | 110 |   |   |
| Ser | Asn | Ser | Tyr | Ser | Trp | Thr | Phe | Gly | His | Gly | Thr | Lys | Val | Glu | Ile |
|   |   | 115 |   |   |   |   | 120 |   |   |   |   | 125 |   |   |   |
| Lys | Arg | Thr | Val | Ala | Ala | Pro | Ser | Val | Phe | Ile | Phe | Pro | Pro | Ser | Asp |
|   | 130 |   |   |   |   | 135 |   |   |   |   | 140 |   |   |   |   |
| Glu | Gln | Leu | Lys | Ser | Gly | Thr | Ala | Ser | Val | Val | Cys | Leu | Leu | Asn | Asn |
| 145 |   |   |   |   | 150 |   |   |   |   | 155 |   |   |   |   | 160 |
| Phe | Tyr | Pro | Arg | Glu | Ala | Lys | Val | Gln | Trp | Lys | Val | Asp | Asn | Ala | Leu |
|   |   |   |   | 165 |   |   |   |   | 170 |   |   |   |   | 175 |   |
| Gln | Ser | Gly | Asn | Ser | Gln | Glu | Ser | Val | Thr | Glu | Gln | Asp | Ser | Lys | Asp |
|   |   |   | 180 |   |   |   |   | 185 |   |   |   |   | 190 |   |   |
| Ser | Thr | Tyr | Ser | Leu | Ser | Ser | Thr | Leu | Thr | Leu | Ser | Lys | Ala | Asp | Tyr |
|   |   | 195 |   |   |   |   | 200 |   |   |   |   | 205 |   |   |   |
| Glu | Lys | His | Lys | Val | Tyr | Ala | Cys | Glu | Val | Thr | His | Gln | Gly | Leu |   |
|   | 210 |   |   |   |   | 215 |   |   |   |   | 220 |   |   |   |   |

<210> SEQ ID NO 63
<211> LENGTH: 630
<212> TYPE: DNA
<213> ORGANISM: Homo sapiens

<400> SEQUENCE: 63

```
ggtctatata agcagagctg ggtacgtcct cacattcagt gatcagcact gaacacagac     60
ccgtcgacgg tgatcaggac tgaacagaga gaactcacca tggagtttgg gctgagctgg    120
cttttttctg tggctatttt aaaaggtgtc cagtgtgagg tgcagctgtt ggagtctggg    180
ggaggcttgg tacagcctgg ggggtccctg agactctcct gtgcagcctc tggattcacc    240
tttagcagct atgccatgag ctgggtccgc caggctccag ggaaggggct ggagtgggtc    300
tcagctatta gtggtagtgg tggtagcaca tactacgcag actccgtgaa gggccggttc    360
accatctcca gagacaattc caagaacacg ctgtatctgc aaatgaacag cctgagagcc    420
gaggacacgg ccgtatatta ctgtgcgaaa gatgggggt actatggttc ggggagttat    480
ggtactttg actactgggg ccagggaacc ctggtcaccg tctcctcagc tagcaccaag    540
ggcccatcgg tcttccccct ggcaccctcc tccaagagca cctctggggg cacagcggcc    600
ctgggctgcc tggtcaagga ctacttcccc                                     630
```

<210> SEQ ID NO 64
<211> LENGTH: 177
<212> TYPE: PRT
<213> ORGANISM: Homo sapiens

<400> SEQUENCE: 64

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Asp Gly Gly Tyr Tyr Gly Ser Gly Ser Tyr Gly
        115                 120                 125

Tyr Phe Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro

<210> SEQ ID NO 65
<211> LENGTH: 728
<212> TYPE: DNA
<213> ORGANISM: Homo sapiens

<400> SEQUENCE: 65
caagcagtgg taacaacgca gagtacgcgg ggggagtcag acccagtcag gacacagcat    60
ggacatgagg gtccccgctc agctcctggg gctcctgctg ctctggttcc caggttccag   120
atgcgacatc cagatgaccc agtctccatc ttccgtgtct ggatctgtag agacagagt    180
caccatcact tgtcgggcga gtcagggtat tagcagctgg ttagcctggt atcagcagaa   240
accaggaaa gcccctaagc tcctgatcta tgctggatcc agtttgcaaa gtggggtccc   300
atcaaggttc agcggcagtg gatttgggac agatttcact ctcaccatca gcagcctgca   360
gcctgaagat tttgcaactt actattgtca acaggctagc agtttccctc ggacattcgg   420
ccaagggacc aaggtggaga tcaaacgtac ggtggctgca ccatctgtct tcatcttccc   480
gccatctgat gagcagttga aatctggaac tgcctctgtt gtgtgcctgc tgaataactt   540
ctatcccaga gaggccaaag tacagtggaa ggtggataac gccctccaat cgggtaactc   600
ccaggagagt gtcacagagc aggacagcaa ggacagcacc tacagcctca gcagcaccct   660
gacgctgagc aaagcagact acgagaaaca caaagtctac gcctgcgaag tcacccatca   720
gggcctga                                                           728

<210> SEQ ID NO 66
<211> LENGTH: 223
<212> TYPE: PRT
<213> ORGANISM: Homo sapiens

<400> SEQUENCE: 66

Met Asp Met Arg Val Pro Ala Gln Leu Leu Gly Leu Leu Leu Leu Trp
1               5                   10                  15

-continued

```
Phe Pro Gly Ser Arg Cys Asp Ile Gln Met Thr Gln Ser Pro Ser Ser
            20                  25                  30

Val Ser Gly Ser Val Gly Asp Arg Val Thr Ile Thr Cys Arg Ala Ser
            35                  40                  45

Gln Gly Ile Ser Ser Trp Leu Ala Trp Tyr Gln Gln Lys Pro Gly Lys
        50              55                  60

Ala Pro Lys Leu Leu Ile Tyr Ala Gly Ser Ser Leu Gln Ser Gly Val
65                      70              75                  80

Pro Ser Arg Phe Ser Gly Ser Gly Phe Gly Thr Asp Phe Thr Leu Thr
                85                  90                  95

Ile Ser Ser Leu Gln Pro Glu Asp Phe Ala Thr Tyr Tyr Cys Gln Gln
                100                 105                 110

Ala Ser Ser Phe Pro Arg Thr Phe Gly Gln Gly Thr Lys Val Glu Ile
            115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu
    210                 215                 220
```